US012751652B2

(12) United States Patent
Bullington et al.

(10) Patent No.: US 12,751,652 B2
(45) Date of Patent: *Oct. 6, 2026

(54) FLUID CONTROL DEVICES AND METHODS OF USING THE SAME

(71) Applicant: Magnolia Medical Technologies, Inc., Seattle, WA (US)

(72) Inventors: Gregory J. Bullington, Seattle, WA (US); Jay M. Miazga, Langley, WA (US); Timothy F. Ramsey, Seattle, WA (US); Abigail Patterson, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 175 days.

This patent is subject to a terminal disclaimer.

(21) Appl. No.: 18/242,900

(22) Filed: Sep. 6, 2023

(65) Prior Publication Data

US 2024/0065590 A1 Feb. 29, 2024

Related U.S. Application Data

(63) Continuation of application No. 16/815,526, filed on Mar. 11, 2020, now Pat. No. 11,857,321.

(Continued)

(51) Int. Cl.

*A61B 5/15* (2006.01)
*B01L 3/00* (2006.01)

(52) U.S. Cl.

CPC .... *A61B 5/150343* (2013.01); *A61B 5/15003* (2013.01); *A61B 5/150099* (2013.01);

(Continued)

(58) Field of Classification Search

None

See application file for complete search history.

(56) References Cited

U.S. PATENT DOCUMENTS 2,674,265 A 4/1954 Lee
2,697,435 A 12/1954 Benjamin (Continued)

FOREIGN PATENT DOCUMENTS

AT 310345 B 9/1973
AT E219383 T1 7/2002

(Continued)

OTHER PUBLICATIONS

Arenas et al., "Asynchronous Testing of 2 Specimen-Diversion Devices to reduce Blood Culture Contamination: A Single-Site Product Supply Quality Improvement Project," J. Emergency Nursing, vol. 47, No. 2, pp. 256-264.e6 (Mar. 2021), 15 pages.

(Continued)

*Primary Examiner* — Lore R Jarrett

(74) *Attorney, Agent, or Firm* — COOLEY LLP

(57) ABSTRACT

An apparatus for procuring bodily fluid samples with reduced contamination includes a housing having a sequestration chamber, an inlet, and an outlet. A flow controller defines a portion of the sequestration chamber and can transition—in response to a suction force exerted by a fluid collection device fluidically coupled to the outlet—from a first state in which the sequestration chamber has a first volume to a second state in which the sequestration chamber has a second volume greater than the first volume, to draw an initial volume of bodily fluid into the sequestration chamber. An actuator is coupled to the housing and is in fluid communication with the inlet and the sequestration chamber in a first configuration, and is transitioned to a second configuration to sequester the sequestration chamber from the inlet, and allow a subsequent volume of bodily fluid to flow from the inlet to the outlet.

30 Claims, 17 Drawing Sheets

Related U.S. Application Data

(60) Provisional application No. 62/816,477, filed on Mar. 11, 2019.

(52) U.S. Cl.
CPC .. *A61B 5/150145* (2013.01); *A61B 5/150755* (2013.01); *A61B 5/150992* (2013.01); *B01L 3/502* (2013.01); *B01L 2200/026* (2013.01); *B01L 2200/141* (2013.01); *B01L 2300/0672* (2013.01); *B01L 2400/082* (2013.01)

(56) References Cited

U.S. PATENT DOCUMENTS

| | | | |
|---|---|---|---|
| 2,707,953 | A | 5/1955 | Ryan |
| 2,876,769 | A | 3/1959 | Cordova |
| 2,952,258 | A | 9/1960 | Chandler |
| 2,992,974 | A | 7/1961 | Belcove et al. |
| 3,013,557 | A | 12/1961 | Pallotta |
| 3,098,016 | A | 7/1963 | Sam et al. |
| 3,382,865 | A | 5/1968 | Worrall, Jr. |
| 3,405,706 | A | 10/1968 | Paul |
| 3,467,021 | A | 9/1969 | Green, Jr. |
| 3,467,095 | A | 9/1969 | Ross |
| 3,494,351 | A | 2/1970 | Horn |
| 3,494,352 | A | 2/1970 | Russo et al. |
| 3,577,980 | A | 5/1971 | Cohen |
| 3,596,652 | A | 8/1971 | Winkelman |
| 3,604,410 | A | 9/1971 | Whitacre |
| 3,635,798 | A | 1/1972 | Kirkham et al. |
| 3,640,267 | A | 2/1972 | Hurtig et al. |
| 3,648,684 | A | 3/1972 | Barnwell et al. |
| 3,650,093 | A | 3/1972 | Rosenberg |
| 3,680,558 | A | 8/1972 | Kapelowitz |
| 3,696,806 | A | 10/1972 | Sausse |
| 3,705,018 | A | 12/1972 | Taylor |
| 3,730,168 | A | 5/1973 | Mcwhorter |
| 3,741,197 | A | 6/1973 | Sanz et al. |
| 3,749,084 | A | 7/1973 | Cucchiara |
| 3,774,604 | A | 11/1973 | Danielsson |
| 3,777,773 | A | 12/1973 | Tolbert |
| 3,779,383 | A | 12/1973 | Ayres |
| 3,803,810 | A | 4/1974 | Rosenberg |
| 3,817,240 | A | 6/1974 | Ayres |
| 3,831,602 | A | 8/1974 | Broadwin |
| 3,834,372 | A | 9/1974 | Turney |
| 3,835,835 | A | 9/1974 | Thompson et al. |
| 3,848,579 | A | 11/1974 | Villa |
| 3,848,581 | A | 11/1974 | Cinqualbre et al. |
| 3,859,998 | A | 1/1975 | Thomas et al. |
| 3,874,367 | A | 4/1975 | Ayres |
| 3,886,930 | A | 6/1975 | Ryan |
| 3,890,203 | A | 6/1975 | Mehl |
| 3,890,968 | A | 6/1975 | Pierce et al. |
| 3,937,211 | A | 2/1976 | Merten |
| 3,943,917 | A | 3/1976 | Johansen |
| 3,945,380 | A | 3/1976 | Dabney et al. |
| 3,960,139 | A | 6/1976 | Bailey |
| 3,978,846 | A | 9/1976 | Bailey |
| 3,996,923 | A | 12/1976 | Guerra |
| 4,056,101 | A | 11/1977 | Geissler et al. |
| 4,057,050 | A | 11/1977 | Sarstedt |
| 4,062,360 | A | 12/1977 | Bentley |
| 4,063,460 | A | 12/1977 | Svensson |
| 4,077,395 | A | 3/1978 | Woolner |
| 4,106,491 | A | 8/1978 | Guerra |
| 4,106,497 | A | 8/1978 | Percarpio |
| 4,133,304 | A | 1/1979 | Bailey |
| 4,133,863 | A | 1/1979 | Koenig |
| 4,150,089 | A | 4/1979 | Linet |
| 4,154,229 | A | 5/1979 | Nugent |
| 4,166,450 | A | 9/1979 | Abramson |
| 4,190,426 | A | 2/1980 | Ruschke |
| 4,193,400 | A | 3/1980 | Loveless et al. |
| 4,202,764 | A | 5/1980 | Afflerbaugh et al. |
| 4,206,282 | A | 6/1980 | Hochstein |
| 4,207,870 | A | 6/1980 | Eldridge |
| 4,210,173 | A | 7/1980 | Choksi et al. |
| 4,212,308 | A | 7/1980 | Percarpio |
| 4,226,236 | A | 10/1980 | Genese |
| 4,238,207 | A | 12/1980 | Ruschke |
| 4,257,416 | A | 3/1981 | Prager |
| 4,275,730 | A | 6/1981 | Hussein |
| 4,298,358 | A | 11/1981 | Ruschke |
| 4,312,362 | A | 1/1982 | Kaufman |
| 4,317,456 | A | 3/1982 | Percarpio |
| 4,327,746 | A | 5/1982 | Feaster |
| 4,340,067 | A | 7/1982 | Rattenborg |
| 4,340,068 | A | 7/1982 | Kaufman |
| 4,349,035 | A | 9/1982 | Thomas et al. |
| 4,354,507 | A | 10/1982 | Raitto |
| 4,370,987 | A | 2/1983 | Bazell et al. |
| 4,373,535 | A | 2/1983 | Martell |
| 4,398,544 | A | 8/1983 | Nugent et al. |
| 4,411,275 | A | 10/1983 | Raitto |
| 4,412,548 | A | 11/1983 | Hoch |
| 4,416,290 | A | 11/1983 | Lutkowski |
| 4,416,291 | A | 11/1983 | Kaufman |
| 4,425,235 | A | 1/1984 | Cornell et al. |
| 4,436,098 | A | 3/1984 | Kaufman |
| 4,444,203 | A | 4/1984 | Engelman |
| 4,459,997 | A | 7/1984 | Sarstedt |
| 4,496,458 | A | 1/1985 | Lee |
| 4,509,534 | A | 4/1985 | Tassin, Jr. |
| 4,551,131 | A | 11/1985 | Miles et al. |
| 4,581,014 | A | 4/1986 | Millerd et al. |
| 4,608,996 | A | 9/1986 | Brown |
| 4,626,248 | A | 12/1986 | Scheller |
| 4,654,027 | A | 3/1987 | Dragan et al. |
| 4,657,027 | A | 4/1987 | Paulsen |
| 4,657,160 | A | 4/1987 | Woods et al. |
| 4,673,386 | A | 6/1987 | Gordon |
| 4,676,256 | A | 6/1987 | Golden |
| 4,679,571 | A | 7/1987 | Frankel et al. |
| 4,690,154 | A | 9/1987 | Woodford et al. |
| 4,699,612 | A | 10/1987 | Hamacher |
| 4,703,763 | A | 11/1987 | McAlister et al. |
| 4,705,497 | A | 11/1987 | Shitaokoshi et al. |
| 4,714,461 | A | 12/1987 | Gabel |
| 4,715,854 | A | 12/1987 | Vaillancourt |
| 4,772,273 | A | 9/1988 | Alchas |
| 4,820,287 | A | 4/1989 | Leonard |
| 4,838,855 | A | 6/1989 | Lynn |
| 4,865,583 | A | 9/1989 | Tu |
| 4,879,098 | A | 11/1989 | Oberhardt et al. |
| 4,886,072 | A | 12/1989 | Percarpio et al. |
| 4,890,627 | A | 1/1990 | Haber et al. |
| 4,904,240 | A | 2/1990 | Hoover |
| 4,936,315 | A | 6/1990 | Lineback |
| 4,980,297 | A | 12/1990 | Haynes et al. |
| 4,988,339 | A | 1/1991 | Vadher |
| 5,009,847 | A | 4/1991 | Solomons |
| 5,027,827 | A | 7/1991 | Cody et al. |
| 5,032,116 | A | 7/1991 | Peterson et al. |
| 5,032,288 | A | 7/1991 | Columbus et al. |
| 5,035,688 | A | 7/1991 | Inui |
| 5,045,185 | A | 9/1991 | Ohnaka et al. |
| 5,052,403 | A | 10/1991 | Haber et al. |
| 5,054,498 | A | 10/1991 | Melet |
| 5,066,284 | A | 11/1991 | Mersch et al. |
| 5,084,034 | A | 1/1992 | Zanotti |
| 5,097,842 | A | 3/1992 | Bonn |
| 5,100,394 | A | 3/1992 | Dudar et al. |
| 5,108,927 | A | 4/1992 | Dorn |
| 5,116,323 | A | 5/1992 | Kreuzer et al. |
| 5,122,129 | A | 6/1992 | Olson et al. |
| 5,126,054 | A | 6/1992 | Matkovich |
| 5,135,489 | A | 8/1992 | Jepson et al. |
| 5,147,329 | A | 9/1992 | Brannon |
| 5,208,160 | A | 5/1993 | Kikyotani et al. |
| 5,222,502 | A | 6/1993 | Kurose |
| 5,269,317 | A | 12/1993 | Bennett |
| 5,286,279 | A | 2/1994 | Wu |
| 5,330,464 | A | 7/1994 | Mathias et al. |

(56) References Cited

U.S. PATENT DOCUMENTS

| | | | |
|---|---|---|---|
| 5,334,162 | A | 8/1994 | Harris |
| 5,354,537 | A | 10/1994 | Moreno |
| 5,360,011 | A | 11/1994 | McCallister |
| 5,372,143 | A | 12/1994 | Bernes et al. |
| 5,395,339 | A | 3/1995 | Talonn et al. |
| 5,417,673 | A | 5/1995 | Gordon |
| 5,429,610 | A | 7/1995 | Vaillancourt |
| 5,431,811 | A | 7/1995 | Tusini et al. |
| 5,439,022 | A | 8/1995 | Summers et al. |
| 5,439,450 | A | 8/1995 | Haedt |
| 5,450,856 | A | 9/1995 | Norris |
| 5,451,321 | A | 9/1995 | Matkovich |
| 5,454,786 | A | 10/1995 | Harris |
| 5,466,228 | A | 11/1995 | Evans |
| 5,472,605 | A | 12/1995 | Zuk, Jr. |
| 5,485,854 | A | 1/1996 | Hollister |
| 5,507,299 | A | 4/1996 | Roland |
| 5,520,193 | A | 5/1996 | Suzuki et al. |
| 5,522,804 | A | 6/1996 | Lynn |
| 5,573,510 | A | 11/1996 | Isaacson |
| 5,573,951 | A | 11/1996 | Gombrich et al. |
| 5,575,777 | A | 11/1996 | Cover et al. |
| 5,577,513 | A | 11/1996 | Van Vlasselaer |
| 5,603,700 | A | 2/1997 | Daneshvar |
| 5,632,906 | A | 5/1997 | Ishida et al. |
| 5,634,893 | A | 6/1997 | Rishton |
| 5,649,912 | A | 7/1997 | Peterson |
| 5,658,271 | A | 8/1997 | Loubser |
| 5,685,846 | A | 11/1997 | Michaels, Jr. |
| 5,691,486 | A | 11/1997 | Behringer et al. |
| 5,749,857 | A | 5/1998 | Cuppy |
| 5,759,160 | A | 6/1998 | Neese et al. |
| 5,762,633 | A | 6/1998 | Whisson |
| 5,772,608 | A | 6/1998 | Dhas |
| 5,785,682 | A | 7/1998 | Grabenkort |
| 5,811,658 | A | 9/1998 | Van Driel et al. |
| 5,824,001 | A | 10/1998 | Erskine |
| 5,857,983 | A | 1/1999 | Douglas et al. |
| 5,865,803 | A | 2/1999 | Major |
| 5,865,812 | A | 2/1999 | Correia |
| 5,871,699 | A | 2/1999 | Ruggeri |
| 5,873,841 | A | 2/1999 | Brannon |
| 5,876,926 | A | 3/1999 | Beecham |
| 5,882,318 | A | 3/1999 | Boyde |
| D410,081 | S | 5/1999 | Sweeney et al. |
| 5,911,705 | A | 6/1999 | Howell |
| 5,922,551 | A | 7/1999 | Durbin et al. |
| RE36,273 | E | 8/1999 | Brannon |
| 5,947,932 | A | 9/1999 | Desecki et al. |
| 5,961,472 | A | 10/1999 | Swendson et al. |
| 5,971,956 | A | 10/1999 | Epstein |
| 5,980,830 | A | 11/1999 | Savage et al. |
| 6,001,307 | A | 12/1999 | Naka et al. |
| 6,010,633 | A | 1/2000 | Zuk, Jr. et al. |
| 6,013,037 | A | 1/2000 | Brannon |
| 6,016,712 | A | 1/2000 | Warden et al. |
| 6,050,957 | A | 4/2000 | Desch |
| 6,103,271 | A | 8/2000 | Morrison et al. |
| 6,106,509 | A | 8/2000 | Loubser |
| 6,126,643 | A | 10/2000 | Vaillancourt |
| 6,159,164 | A | 12/2000 | Neese et al. |
| 6,171,493 | B1 | 1/2001 | Zia et al. |
| 6,190,855 | B1 | 2/2001 | Herman et al. |
| 6,210,909 | B1 | 4/2001 | Guirguis |
| 6,224,561 | B1 | 5/2001 | Swendson et al. |
| 6,254,581 | B1 | 7/2001 | Scott |
| 6,296,020 | B1 | 10/2001 | McNeely et al. |
| 6,299,131 | B1 | 10/2001 | Ryan |
| 6,306,614 | B1 | 10/2001 | Romaschin et al. |
| 6,325,975 | B1 | 12/2001 | Naka et al. |
| 6,328,726 | B1 | 12/2001 | Ishida et al. |
| 6,355,023 | B1 | 3/2002 | Roth et al. |
| 6,364,847 | B1 | 4/2002 | Shulze et al. |
| 6,364,890 | B1 | 4/2002 | Lum et al. |
| 6,368,306 | B1 | 4/2002 | Koska |
| 6,387,086 | B2 | 5/2002 | Mathias et al. |
| 6,398,743 | B1 | 6/2002 | Halseth et al. |
| 6,403,381 | B1 | 6/2002 | Mann et al. |
| 6,416,496 | B1 | 7/2002 | Rogers et al. |
| 6,440,725 | B1 | 8/2002 | Pourahmadi et al. |
| 6,478,775 | B1 | 11/2002 | Galt et al. |
| 6,506,182 | B2 | 1/2003 | Estabrook et al. |
| 6,511,439 | B1 | 1/2003 | Tabata et al. |
| 6,520,948 | B1 | 2/2003 | Mathias et al. |
| 6,569,117 | B1 | 5/2003 | Ziv et al. |
| 6,592,555 | B1 | 7/2003 | Wen-Pi et al. |
| 6,592,613 | B1 | 7/2003 | Ishida et al. |
| 6,626,884 | B1 | 9/2003 | Dillon et al. |
| 6,629,959 | B2 | 10/2003 | Kuracina et al. |
| 6,638,252 | B2 | 10/2003 | Moulton et al. |
| 6,638,263 | B1 | 10/2003 | Theeuwes et al. |
| 6,648,835 | B1 | 11/2003 | Shemesh |
| 6,692,479 | B2 | 2/2004 | Kraus et al. |
| 6,695,004 | B1 | 2/2004 | Raybuck |
| 6,712,963 | B2 | 3/2004 | Schick |
| 6,716,187 | B1 | 4/2004 | Jorgensen et al. |
| 6,716,396 | B1 | 4/2004 | Anderson et al. |
| 6,733,433 | B1 | 5/2004 | Fell |
| 6,736,783 | B2 | 5/2004 | Blake et al. |
| 6,746,420 | B1 | 6/2004 | Prestidge et al. |
| 6,772,513 | B1 | 8/2004 | Frye-Mason et al. |
| 6,843,775 | B2 | 1/2005 | Hyun |
| 6,860,871 | B2 | 3/2005 | Kuracina et al. |
| 6,905,483 | B2 | 6/2005 | Newby et al. |
| 6,913,580 | B2 | 7/2005 | Stone |
| 6,945,948 | B2 | 9/2005 | Bainbridge et al. |
| 6,979,323 | B2 | 12/2005 | Rogers et al. |
| 7,044,941 | B2 | 5/2006 | Mathias et al. |
| 7,052,603 | B2 | 5/2006 | Schick |
| 7,055,401 | B2 | 6/2006 | Prybella et al. |
| 7,087,047 | B2 | 8/2006 | Kraus et al. |
| 7,141,097 | B2 | 11/2006 | Leahey |
| 7,241,281 | B2 | 7/2007 | Coelho et al. |
| 7,264,608 | B2 | 9/2007 | Bischof et al. |
| 7,306,736 | B2 | 12/2007 | Collins et al. |
| 7,314,452 | B2 | 1/2008 | Madonia |
| 7,316,662 | B2 | 1/2008 | Delnevo et al. |
| 7,335,188 | B2 | 2/2008 | Graf |
| 7,351,228 | B2 | 4/2008 | Keane et al. |
| 7,384,416 | B2 | 6/2008 | Goudaliez et al. |
| 7,435,231 | B2 | 10/2008 | Mathias et al. |
| 7,461,671 | B2 | 12/2008 | Ehwald et al. |
| 7,479,131 | B2 | 1/2009 | Mathias et al. |
| 7,544,324 | B2 | 6/2009 | Tung et al. |
| 7,614,857 | B2 | 11/2009 | Fuechslin et al. |
| 7,615,033 | B2 | 11/2009 | Leong |
| 7,618,407 | B2 | 11/2009 | Demay et al. |
| 7,648,491 | B2 | 1/2010 | Rogers |
| 7,666,166 | B1 | 2/2010 | Emmert et al. |
| 7,744,573 | B2 | 6/2010 | Gordon et al. |
| 7,766,879 | B2 | 8/2010 | Tan et al. |
| 7,780,794 | B2 | 8/2010 | Rogers et al. |
| 7,896,817 | B2 | 3/2011 | Garrison |
| 7,914,508 | B2 | 3/2011 | Engstrom |
| 7,923,053 | B2 | 4/2011 | Kitching et al. |
| 7,963,950 | B2 | 6/2011 | Madonia |
| 7,985,302 | B2 | 7/2011 | Rogers et al. |
| 8,070,725 | B2 | 12/2011 | Christensen |
| 8,109,157 | B2 | 2/2012 | Kanayama et al. |
| RE43,283 | E | 3/2012 | Ishida et al. |
| 8,197,420 | B2 | 6/2012 | Patton |
| 8,206,318 | B2 | 6/2012 | Uchiyama et al. |
| 8,206,514 | B2 | 6/2012 | Rogers et al. |
| 8,231,546 | B2 | 7/2012 | Patton |
| 8,282,605 | B2 | 10/2012 | Tan et al. |
| 8,287,499 | B2 | 10/2012 | Miyasaka |
| 8,337,418 | B2 | 12/2012 | Patton |
| 8,349,254 | B2 | 1/2013 | Hoshino et al. |
| 8,356,644 | B2 | 1/2013 | Chong et al. |
| 8,377,040 | B2 | 2/2013 | Burkholz et al. |
| 8,382,712 | B2 | 2/2013 | Kim |
| 8,383,044 | B2 | 2/2013 | Davis et al. |
| 8,412,300 | B2 | 4/2013 | Sonderegger |
| 8,523,826 | B2 | 9/2013 | Layton, Jr. |

(56) References Cited

U.S. PATENT DOCUMENTS

| | | | |
|---|---|---|---|
| 8,535,241 | B2 | 9/2013 | Bullington et al. |
| 8,540,663 | B2 | 9/2013 | Davey et al. |
| 8,568,371 | B2 | 10/2013 | Siopes et al. |
| 8,574,203 | B2 | 11/2013 | Stout et al. |
| 8,603,009 | B2 | 12/2013 | Tan et al. |
| 8,647,286 | B2 | 2/2014 | Patton |
| 8,679,063 | B2 | 3/2014 | Stout et al. |
| 8,747,779 | B2 | 6/2014 | Sprague et al. |
| 8,772,046 | B2 | 7/2014 | Fraden et al. |
| 8,795,198 | B2 | 8/2014 | Tan et al. |
| 8,808,202 | B2 | 8/2014 | Brancazio |
| 8,827,958 | B2 | 9/2014 | Bierman et al. |
| 8,832,894 | B2 | 9/2014 | Rogers et al. |
| 8,834,650 | B2 | 9/2014 | Rogers et al. |
| 8,864,684 | B2 | 10/2014 | Bullington et al. |
| 8,876,734 | B2 | 11/2014 | Patton |
| 8,992,505 | B2 | 3/2015 | Thorne, Jr. et al. |
| 8,999,073 | B2 | 4/2015 | Rogers et al. |
| 9,022,950 | B2 | 5/2015 | Bullington et al. |
| 9,022,951 | B2 | 5/2015 | Bullington et al. |
| 9,060,724 | B2 | 6/2015 | Bullington et al. |
| 9,060,725 | B2 | 6/2015 | Bullington et al. |
| 9,138,572 | B2 | 9/2015 | Zeytoonian et al. |
| 9,149,576 | B2 | 10/2015 | Bullington et al. |
| 9,155,495 | B2 | 10/2015 | Bullington et al. |
| 9,204,864 | B2 | 12/2015 | Bullington et al. |
| 9,205,198 | B2 | 12/2015 | Py |
| 9,233,208 | B2 | 1/2016 | Tekeste |
| RE45,896 | E | 2/2016 | Stout et al. |
| 9,259,284 | B2 | 2/2016 | Rogers et al. |
| 9,314,201 | B2 | 4/2016 | Burkholz et al. |
| 9,320,459 | B2 | 4/2016 | Chin et al. |
| 9,820,682 | B2 | 11/2017 | Rogers et al. |
| 9,855,001 | B2 | 1/2018 | Patton |
| 9,855,002 | B2 | 1/2018 | Patton |
| 9,855,386 | B2 | 1/2018 | Close et al. |
| 9,861,306 | B2 | 1/2018 | Patton |
| 9,872,645 | B2 | 1/2018 | Patton |
| 9,877,674 | B2 | 1/2018 | Holmes et al. |
| 9,877,675 | B2 | 1/2018 | Baid |
| 9,895,092 | B2 | 2/2018 | Burkholz |
| 9,931,466 | B2 | 4/2018 | Bullington et al. |
| 9,950,084 | B2 | 4/2018 | Bullington et al. |
| 9,962,489 | B2 | 5/2018 | Hopkins |
| 9,999,383 | B2 | 6/2018 | Bullington et al. |
| 10,010,282 | B2 | 7/2018 | Rogers et al. |
| 10,022,079 | B2 | 7/2018 | Hopkins |
| 10,022,530 | B2 | 7/2018 | Tekeste |
| 10,028,687 | B2 | 7/2018 | Patton |
| 10,028,688 | B2 | 7/2018 | Patton |
| 10,028,689 | B2 | 7/2018 | Patton |
| 10,039,483 | B2 | 8/2018 | Bullington et al. |
| 10,045,724 | B2 | 8/2018 | Patton |
| 10,052,053 | B2 | 8/2018 | Patton |
| 10,080,516 | B2 | 9/2018 | Ellis et al. |
| 10,086,142 | B2 | 10/2018 | Tekeste |
| 10,123,783 | B2 | 11/2018 | Bullington et al. |
| 10,143,412 | B2 | 12/2018 | Rogers et al. |
| 10,143,413 | B2 | 12/2018 | Garrett et al. |
| 10,206,613 | B2 | 2/2019 | Bullington et al. |
| 10,220,139 | B2 | 3/2019 | Bullington et al. |
| 10,238,326 | B2 | 3/2019 | Gil et al. |
| 10,251,590 | B2 | 4/2019 | Bullington et al. |
| 10,265,007 | B2 | 4/2019 | Bullington et al. |
| 10,292,633 | B2 | 5/2019 | Bullington et al. |
| 10,299,713 | B2 | 5/2019 | Patton |
| 10,369,285 | B2 | 8/2019 | Hopkins |
| 10,433,779 | B2 | 10/2019 | Bullington et al. |
| 10,463,792 | B2 | 11/2019 | Hopkins |
| 10,596,315 | B2 | 3/2020 | Bullington et al. |
| 10,624,977 | B2 | 4/2020 | Bullington et al. |
| 10,736,554 | B2 | 8/2020 | Bullington et al. |
| 10,772,548 | B2 | 9/2020 | Bullington et al. |
| 10,813,579 | B2 | 10/2020 | Baid |
| 10,827,964 | B2 | 11/2020 | Rogers et al. |
| 10,856,791 | B2 | 12/2020 | McHale et al. |
| 10,881,343 | B2 | 1/2021 | Bullington et al. |
| 10,888,262 | B2 | 1/2021 | Russ et al. |
| 10,912,506 | B2 | 2/2021 | Bullington et al. |
| 11,076,787 | B2 | 8/2021 | Bullington et al. |
| 11,116,904 | B2 | 9/2021 | Hopkins |
| 11,167,085 | B2 | 11/2021 | Hopkins |
| 11,234,626 | B2 | 2/2022 | Bullington et al. |
| 11,253,649 | B2 | 2/2022 | Hopkins |
| 11,259,727 | B2 | 3/2022 | Bullington et al. |
| 11,311,218 | B2 | 4/2022 | Bullington et al. |
| 11,317,838 | B2 | 5/2022 | Bullington et al. |
| 11,318,459 | B2 | 5/2022 | Shi et al. |
| 11,395,611 | B2 | 7/2022 | Bullington et al. |
| 11,395,612 | B2 | 7/2022 | Bullington et al. |
| 11,419,531 | B2 | 8/2022 | Bullington et al. |
| 11,529,081 | B2 | 12/2022 | Bullington et al. |
| 11,589,786 | B2 | 2/2023 | Bullington et al. |
| 11,607,159 | B2 | 3/2023 | Bullington et al. |
| 11,653,863 | B2 | 5/2023 | Bullington et al. |
| 11,660,030 | B2 | 5/2023 | Bullington et al. |
| 11,737,693 | B2 | 8/2023 | Bullington et al. |
| 11,786,155 | B2 | 10/2023 | Bullington et al. |
| 11,789,017 | B2 | 10/2023 | Bullington et al. |
| 11,819,329 | B2 | 11/2023 | Bullington et al. |
| 11,857,321 | B2 | 1/2024 | Bullington et al. |
| 11,890,452 | B2 | 2/2024 | Bullington et al. |
| 11,903,709 | B2 | 2/2024 | Bullington et al. |
| 11,903,710 | B2 | 2/2024 | Bullington et al. |
| 11,998,332 | B2 | 6/2024 | Bullington et al. |
| 12,083,234 | B2 | 9/2024 | Bullington et al. |
| 12,133,968 | B2 | 11/2024 | Bullington et al. |
| 12,138,052 | B1 | 11/2024 | Rogers et al. |
| 12,150,763 | B2 | 11/2024 | Bullington et al. |
| 12,186,080 | B2 | 1/2025 | Bullington et al. |
| 12,193,816 | B2 | 1/2025 | Bullington et al. |
| 12,290,363 | B2 | 5/2025 | Bullington et al. |
| 12,471,815 | B2 | 11/2025 | Bullington et al. |
| 12,471,816 | B2 | 11/2025 | Bullington et al. |
| 12,478,300 | B2 | 11/2025 | Bullington et al. |
| 12,478,301 | B2 | 11/2025 | Bullington et al. |
| 12,502,109 | B2 | 12/2025 | Bullington et al. |
| 12,551,150 | B2 | 2/2026 | Bullington et al. |
| 12,564,341 | B2 | 3/2026 | Bullington et al. |
| 12,575,772 | B2 | 3/2026 | Bullington et al. |
| 12,576,204 | B2 | 3/2026 | Bullington |
| 2001/0031932 | A1 | 10/2001 | Blake et al. |
| 2001/0039058 | A1 | 11/2001 | Iheme et al. |
| 2002/0002349 | A1 | 1/2002 | Flaherty et al. |
| 2002/0004647 | A1 | 1/2002 | Leong |
| 2002/0107469 | A1 | 8/2002 | Bolan et al. |
| 2002/0183651 | A1 | 12/2002 | Hyun |
| 2002/0193751 | A1 | 12/2002 | Theeuwes et al. |
| 2003/0013991 | A1 | 1/2003 | Stone |
| 2003/0055381 | A1 | 3/2003 | Wilkinson |
| 2003/0069543 | A1 | 4/2003 | Carpenter et al. |
| 2003/0105414 | A1 | 6/2003 | Leong |
| 2003/0208151 | A1 | 11/2003 | Kraus et al. |
| 2004/0000309 | A1 | 1/2004 | Alston |
| 2004/0009542 | A1 | 1/2004 | Dumont et al. |
| 2004/0010228 | A1 | 1/2004 | Swenson et al. |
| 2004/0054283 | A1 | 3/2004 | Corey et al. |
| 2004/0054333 | A1 | 3/2004 | Theeuwes et al. |
| 2004/0124389 | A1 | 7/2004 | Phillips |
| 2004/0127816 | A1 | 7/2004 | Galvao |
| 2004/0147855 | A1 | 7/2004 | Marsden |
| 2005/0004524 | A1 | 1/2005 | Newby et al. |
| 2005/0010136 | A1 | 1/2005 | Restelli et al. |
| 2005/0054949 | A1 | 3/2005 | McKinnon et al. |
| 2005/0082218 | A1 | 4/2005 | Verri et al. |
| 2005/0148993 | A1 | 7/2005 | Mathias et al. |
| 2005/0154368 | A1 | 7/2005 | Lim et al. |
| 2005/0161112 | A1 | 7/2005 | Ehwald et al. |
| 2005/0199077 | A1 | 9/2005 | Prybella et al. |
| 2005/0240161 | A1 | 10/2005 | Crawford |
| 2005/0245885 | A1 | 11/2005 | Brown |
| 2005/0273019 | A1 | 12/2005 | Conway et al. |
| 2005/0277848 | A1 | 12/2005 | Graf |
| 2005/0281713 | A1 | 12/2005 | Hampsch et al. |

(56) References Cited

U.S. PATENT DOCUMENTS

2006/0009713 A1 1/2006 Flaherty
2006/0018790 A1 1/2006 Naka et al.
2006/0111667 A1 5/2006 Matsuura et al.
2006/0155212 A1 7/2006 Madonia
2006/0251622 A1 11/2006 Suzuki et al.
2006/0287639 A1 12/2006 Sharp
2007/0083162 A1 4/2007 O'Reagan et al.
2007/0088279 A1 4/2007 Shue et al.
2007/0100250 A1 5/2007 Kline
2007/0119508 A1 5/2007 West et al.
2007/0172389 A1 7/2007 Wilding et al.
2007/0191716 A1 8/2007 Goldberger et al.
2007/0287948 A1 12/2007 Sakiewicz
2008/0086085 A1 4/2008 Brown
2008/0108954 A1 5/2008 Mathias et al.
2008/0114304 A1 5/2008 Nalesso et al.
2008/0145933 A1 6/2008 Patton
2008/0167577 A1 7/2008 Weilbacher et al.
2008/0185056 A1 8/2008 Diodati et al.
2008/0200837 A1 8/2008 Frazier et al.
2008/0254471 A1 10/2008 Bordano
2008/0255523 A1 10/2008 Grinberg
2008/0312576 A1 12/2008 McKinnon et al.
2008/0319346 A1 12/2008 Crawford et al.
2009/0076441 A1 3/2009 Sebban
2009/0173685 A1 7/2009 Imai et al.
2009/0177117 A1 7/2009 Amano et al.
2009/0192447 A1 7/2009 Andersen et al.
2009/0215159 A1 8/2009 Kirby
2009/0227896 A1 9/2009 Alvin Tan et al.
2009/0301317 A1 12/2009 Andrews
2009/0306601 A1 12/2009 Shaw et al.
2010/0010372 A1 1/2010 Brown et al.
2010/0042048 A1 2/2010 Christensen
2010/0057004 A1 3/2010 Christensen et al.
2010/0094171 A1 4/2010 Conway et al.
2010/0152681 A1 6/2010 Mathias
2010/0185134 A1 7/2010 Houwen et al.
2010/0234768 A1 9/2010 Uchiyama et al.
2010/0240964 A1 9/2010 Sterling et al.
2010/0252118 A1 10/2010 Fraden et al.
2010/0255589 A1 10/2010 Saiki et al.
2010/0268118 A1 10/2010 Schweiger
2010/0286513 A1 11/2010 Pollard, Jr. et al.
2010/0298671 A1 11/2010 Asakura et al.
2011/0009717 A1 1/2011 Davis et al.
2011/0046602 A1 2/2011 Grimm et al.
2011/0092856 A1 4/2011 Freeman et al.
2011/0125058 A1 5/2011 Levinson et al.
2011/0178427 A1 7/2011 Tan et al.
2011/0198221 A1 8/2011 Angelescu
2011/0288441 A1 11/2011 Taguchi
2011/0306856 A1 12/2011 Rule et al.
2011/0306899 A1 12/2011 Brown et al.
2011/0313318 A1 12/2011 Rule et al.
2011/0319859 A1 12/2011 Zeytoonian et al.
2012/0004619 A1 1/2012 Stephens et al.
2012/0016266 A1 1/2012 Burkholz
2012/0017999 A1 1/2012 Velschow
2012/0022404 A1 1/2012 Fojtik
2012/0029494 A1 2/2012 Wittenberger et al.
2012/0035540 A1 2/2012 Ferren et al.
2012/0095367 A1 4/2012 Patton
2012/0123297 A1 5/2012 Brancazio
2012/0215131 A1 8/2012 Patton
2012/0226239 A1 9/2012 Green
2012/0245042 A1 9/2012 Liu et al.
2012/0265099 A1 10/2012 Goodnow, II et al.
2012/0265128 A1 10/2012 Kolln
2012/0277697 A1 11/2012 Haghgooie et al.
2012/0323142 A1 12/2012 Allen et al.
2013/0023792 A1 1/2013 Markey et al.
2013/0079604 A1 3/2013 Patton
2013/0085514 A1 4/2013 Lee et al.
2013/0116599 A1 5/2013 Bullington et al.
2013/0158506 A1 6/2013 Harris et al.
2013/0289420 A1 10/2013 Pfeiffer et al.
2013/0295602 A1 11/2013 Fowler et al.
2013/0317391 A1 11/2013 Bullington et al.
2014/0008366 A1 1/2014 Genosar
2014/0039348 A1 2/2014 Bullington et al.
2014/0051062 A1 2/2014 Vanapalli et al.
2014/0066880 A1 3/2014 Prince et al.
2014/0081172 A1 3/2014 Patton
2014/0107564 A1 4/2014 Bullington et al.
2014/0124542 A1 5/2014 Kojima et al.
2014/0128775 A1 5/2014 Andreae et al.
2014/0155781 A1 6/2014 Bullington et al.
2014/0155782 A1 6/2014 Bullington et al.
2014/0163419 A1 6/2014 Bullington et al.
2014/0188002 A1 7/2014 Close et al.
2014/0208978 A1 7/2014 Sunder et al.
2014/0221873 A1 8/2014 Hayakawa et al.
2014/0257249 A1 9/2014 Witt
2014/0276039 A1 9/2014 Cowan et al.
2014/0305196 A1 10/2014 Ellis et al.
2014/0336536 A1 11/2014 Brancazio
2015/0000061 A1 1/2015 Rogers et al.
2015/0011847 A1 1/2015 Hayden
2015/0011910 A1 1/2015 Bullington et al.
2015/0011911 A1 1/2015 Bullington et al.
2015/0018715 A1 1/2015 Walterspiel
2015/0025454 A1 1/2015 Wetzel et al.
2015/0025455 A1 1/2015 Shetty et al.
2015/0025456 A1 1/2015 Shetty et al.
2015/0073304 A1 3/2015 Millerd
2015/0073348 A1 3/2015 Bullington et al.
2015/0094615 A1 4/2015 Patton
2015/0099996 A1 4/2015 Bullington et al.
2015/0151298 A1 6/2015 Hobbs et al.
2015/0257691 A1 9/2015 Bullington et al.
2015/0314105 A1 11/2015 Gasparyan et al.
2015/0342510 A1 12/2015 Bullington et al.
2015/0351678 A1 12/2015 Bullington et al.
2015/0351679 A1 12/2015 Bullington et al.
2015/0359473 A1 12/2015 Garrett et al.
2015/0367069 A1 12/2015 Bullington et al.
2016/0008579 A1 1/2016 Burkholz et al.
2016/0038068 A1 2/2016 Chickering, III et al.
2016/0038684 A1 2/2016 Lum et al.
2016/0081606 A1 3/2016 Russ et al.
2016/0089070 A1 3/2016 Russ et al.
2016/0113560 A1 4/2016 Bullington et al.
2016/0135724 A1 5/2016 Bullington et al.
2016/0174888 A1 6/2016 Berthier et al.
2016/0174948 A1 6/2016 Kato et al.
2016/0213294 A1 7/2016 Patton
2016/0257586 A1 9/2016 Shaamsundarr
2016/0361006 A1 12/2016 Bullington et al.
2016/0367177 A1 12/2016 Edelhauser et al.
2017/0020427 A1 1/2017 Rogers et al.
2017/0020428 A1 1/2017 Rogers et al.
2017/0059552 A1 3/2017 Campton et al.
2017/0065733 A1 3/2017 Bullington et al.
2017/0071519 A1 3/2017 Gelfand et al.
2017/0150913 A1 6/2017 Patton
2017/0153165 A1 6/2017 Nwadigo
2017/0156654 A1 6/2017 Patton
2017/0172482 A1 6/2017 Patton
2017/0181683 A1 6/2017 Patton
2017/0227536 A1 8/2017 Matsuura
2017/0276679 A1 9/2017 Chapman et al.
2017/0327867 A1 11/2017 Dohale et al.
2017/0361019 A1 12/2017 Hopkins
2018/0078186 A1 3/2018 Patton
2018/0085042 A1 3/2018 Patton
2018/0092582 A1 4/2018 Patton
2018/0092583 A1 4/2018 Patton
2018/0092584 A1 4/2018 Bullington et al.
2018/0093077 A1 4/2018 Harding et al.
2018/0098723 A1 4/2018 Patton
2018/0116577 A1 5/2018 Bullington et al.
2018/0140240 A1 5/2018 Bullington et al.
2018/0160958 A1 6/2018 Baid

(56) References Cited

U.S. PATENT DOCUMENTS

| | | | |
|---|---|---|---|
| 2018/0177445 | A1 | 6/2018 | Rogers et al. |
| 2018/0177943 | A1 | 6/2018 | Bullington et al. |
| 2018/0207300 | A1 | 7/2018 | Bullington et al. |
| 2018/0242890 | A1 | 8/2018 | Chickering, III et al. |
| 2018/0271425 | A1 | 9/2018 | Rogers et al. |
| 2018/0289894 | A1 | 10/2018 | Hopkins |
| 2018/0321270 | A1 | 11/2018 | Iwashita et al. |
| 2018/0353117 | A1 | 12/2018 | Bullington et al. |
| 2019/0000367 | A1 | 1/2019 | Lundquist et al. |
| 2019/0030293 | A1 | 1/2019 | Rogers et al. |
| 2019/0049442 | A1 | 2/2019 | Guirguis |
| 2019/0076074 | A1 | 3/2019 | Bullington et al. |
| 2019/0150818 | A1 | 5/2019 | Bullington et al. |
| 2019/0151536 | A1 | 5/2019 | Bullington et al. |
| 2019/0159711 | A1 | 5/2019 | Rogers et al. |
| 2019/0175085 | A1 | 6/2019 | Bullington et al. |
| 2019/0175087 | A1 | 6/2019 | Bullington et al. |
| 2019/0209066 | A1 | 7/2019 | Bullington et al. |
| 2019/0365303 | A1 | 12/2019 | Bullington et al. |
| 2019/0374145 | A1 | 12/2019 | Breindel et al. |
| 2020/0060595 | A1 | 2/2020 | Bullington et al. |
| 2020/0060596 | A1 | 2/2020 | Patton |
| 2020/0197925 | A1 | 6/2020 | Ivosevic et al. |
| 2020/0214611 | A1 | 7/2020 | Ivosevic |
| 2020/0215211 | A1 | 7/2020 | Bullington et al. |
| 2020/0253524 | A1 | 8/2020 | Bullington et al. |
| 2020/0281514 | A1 | 9/2020 | Rogers et al. |
| 2020/0289039 | A1 | 9/2020 | Bullington et al. |
| 2020/0305780 | A1 | 10/2020 | Rogers et al. |
| 2020/0352497 | A1 | 11/2020 | Brewer et al. |
| 2020/0359951 | A1 | 11/2020 | Bullington et al. |
| 2021/0008280 | A1 | 1/2021 | Bullington et al. |
| 2021/0085230 | A1 | 3/2021 | Brewer et al. |
| 2021/0169387 | A1 | 6/2021 | Bullington et al. |
| 2021/0178389 | A1 | 6/2021 | Bullington et al. |
| 2021/0186392 | A1 | 6/2021 | Bullington et al. |
| 2021/0290123 | A1 | 9/2021 | Sawyer |
| 2021/0345919 | A1 | 11/2021 | Brewer et al. |
| 2021/0345920 | A1 | 11/2021 | Brewer et al. |
| 2021/0345921 | A1 | 11/2021 | Brewer et al. |
| 2021/0345922 | A1 | 11/2021 | Brewer et al. |
| 2021/0353193 | A1 | 11/2021 | Bullington et al. |
| 2021/0353194 | A1 | 11/2021 | Bullington et al. |
| 2021/0361206 | A1 | 11/2021 | Bullington et al. |
| 2021/0361207 | A1 | 11/2021 | Rogers et al. |
| 2022/0023539 | A1 | 1/2022 | Hopkins |
| 2022/0071533 | A1 | 3/2022 | Bullington et al. |
| 2022/0079482 | A1 | 3/2022 | Bullington et al. |
| 2022/0151525 | A1 | 5/2022 | Bullington et al. |
| 2022/0151526 | A1 | 5/2022 | Bullington et al. |
| 2022/0151527 | A1 | 5/2022 | Bullington et al. |
| 2022/0175284 | A1 | 6/2022 | Bullington et al. |
| 2022/0183600 | A1 | 6/2022 | Bullington et al. |
| 2022/0218248 | A1 | 7/2022 | Bullington et al. |
| 2022/0218249 | A1 | 7/2022 | Bullington et al. |
| 2022/0218250 | A1 | 7/2022 | Bullington et al. |
| 2022/0287604 | A1 | 9/2022 | Armstrong et al. |
| 2022/0304600 | A1 | 9/2022 | Hammer |
| 2022/0304601 | A1 | 9/2022 | Bullington et al. |
| 2022/0304664 | A1 | 9/2022 | Hammer |
| 2022/0361786 | A1 | 11/2022 | Bullington et al. |
| 2022/0369970 | A1 | 11/2022 | Bullington et al. |
| 2022/0369971 | A1 | 11/2022 | Bullington et al. |
| 2022/0369972 | A1 | 11/2022 | Bullington et al. |
| 2023/0109255 | A1 | 4/2023 | Rogers et al. |
| 2023/0172502 | A1 | 6/2023 | Bullington et al. |
| 2023/0190157 | A1 | 6/2023 | Bullington et al. |
| 2023/0240571 | A1 | 8/2023 | Bullington et al. |
| 2023/0248281 | A1 | 8/2023 | Bullington et al. |
| 2023/0363674 | A1 | 11/2023 | Bullington et al. |
| 2023/0417746 | A1 | 12/2023 | Bullington et al. |
| 2024/0008780 | A1 | 1/2024 | Bullington et al. |
| 2024/0041369 | A1 | 2/2024 | Bullington et al. |
| 2024/0041370 | A1 | 2/2024 | Bullington et al. |
| 2024/0057908 | A1 | 2/2024 | Bullington et al. |
| 2024/0131258 | A1 | 4/2024 | Bullington et al. |
| 2024/0138734 | A1 | 5/2024 | Bullington et al. |
| 2024/0164670 | A1 | 5/2024 | Patton |
| 2024/0306963 | A1 | 9/2024 | Bullington et al. |
| 2024/0306964 | A1 | 9/2024 | Bullington et al. |
| 2024/0315620 | A1 | 9/2024 | Bullington et al. |
| 2024/0315621 | A1 | 9/2024 | Bullington et al. |
| 2024/0315622 | A1 | 9/2024 | Bullington et al. |
| 2024/0315623 | A1 | 9/2024 | Bullington et al. |
| 2024/0315624 | A1 | 9/2024 | Bullington et al. |
| 2025/0082235 | A1 | 3/2025 | Bullington et al. |
| 2025/0120628 | A1 | 4/2025 | Bullington et al. |
| 2025/0235133 | A1 | 7/2025 | Bullington et al. |
| 2025/0235613 | A1 | 7/2025 | Bullington et al. |
| 2025/0275697 | A1 | 9/2025 | Bullington et al. |
| 2026/0033759 | A1 | 2/2026 | Bullington et al. |
| 2026/0115343 | A1 | 4/2026 | Bullington et al. |

FOREIGN PATENT DOCUMENTS

| | | | |
|---|---|---|---|
| AU | 736156 | B2 | 7/2001 |
| AU | 2003244890 | A1 | 1/2004 |
| BR | 112012025546 | A2 | 6/2016 |
| CA | 1264275 | A | 1/1990 |
| CN | 86103696 | A | 1/1987 |
| CN | 2115767 | U | 9/1992 |
| CN | 1713928 | A | 12/2005 |
| CN | 1784186 | A | 6/2006 |
| CN | 1901955 | A | 1/2007 |
| CN | 2907683 | Y | 6/2007 |
| CN | 1325126 | C | 7/2007 |
| CN | 101060871 | A | 10/2007 |
| CN | 101309641 | A | 11/2008 |
| CN | 101352357 | A | 1/2009 |
| CN | 101437450 | A | 5/2009 |
| CN | 101564301 | A | 10/2009 |
| CN | 101631498 | A | 1/2010 |
| CN | 101676001 | A | 3/2010 |
| CN | 101785676 | A | 7/2010 |
| CN | 101801445 | A | 8/2010 |
| CN | 201617841 | U | 11/2010 |
| CN | 102421362 | A | 4/2012 |
| CN | 102548524 | A | 7/2012 |
| CN | 102811754 | A | 12/2012 |
| CN | 102971040 | A | 3/2013 |
| CN | 103027727 | A | 4/2013 |
| CN | 101626803 | B | 8/2013 |
| CN | 103477201 | A | 12/2013 |
| CN | 103619386 | A | 3/2014 |
| CN | 104971390 | A | 10/2015 |
| CN | 105090005 | A | 11/2015 |
| CN | 105612346 | A | 5/2016 |
| CN | 105813669 | A | 7/2016 |
| CN | 107736901 | A | 2/2018 |
| CN | 209916854 | U | 1/2020 |
| DE | 7203008 | U | 5/1972 |
| DE | 2203858 | A1 | 5/1973 |
| DE | 2541494 | A1 | 3/1977 |
| DE | 2203858 | B2 | 10/1977 |
| DE | 2946660 | A1 | 5/1981 |
| DE | 3403957 | A1 | 8/1985 |
| DE | 4026732 | A1 | 2/1992 |
| DE | 29913417 | U1 | 12/2000 |
| DE | 10038026 | A1 | 2/2001 |
| DE | 10134913 | A1 | 2/2003 |
| DE | 10134913 | C2 | 6/2003 |
| DE | 10243129 | A1 | 4/2004 |
| DE | 69632870 | T2 | 7/2005 |
| DE | 102009057792 | B4 | 8/2016 |
| EP | 0181957 | A1 | 5/1986 |
| EP | 0207304 | A1 | 1/1987 |
| EP | 0448795 | A2 | 10/1991 |
| EP | 0208053 | B1 | 12/1991 |
| EP | 0329786 | B1 | 1/1993 |
| EP | 0486059 | B1 | 1/1997 |
| EP | 1144026 | B1 | 7/2004 |
| EP | 1505159 | B1 | 5/2008 |
| EP | 1980204 | A1 | 10/2008 |
| EP | 2254472 | A2 | 12/2010 |

(56) References Cited

FOREIGN PATENT DOCUMENTS

| | | | |
|---|---|---|---|
| EP | 1381438 | B1 | 5/2012 |
| EP | 2254472 | B1 | 5/2016 |
| EP | 1487369 | B1 | 5/2017 |
| EP | 2986218 | B1 | 12/2017 |
| EP | 2178585 | B1 | 4/2021 |
| EP | 3938108 | B1 | 8/2023 |
| EP | 4218575 | A2 | 8/2023 |
| ES | 2564496 | T3 | 3/2016 |
| FR | 2110516 | A5 | 6/1972 |
| FR | 2691364 | B1 | 8/1999 |
| FR | 2833175 | B1 | 5/2004 |
| FR | 2851167 | B1 | 10/2005 |
| GB | 1506449 | A | 4/1978 |
| GB | 1562686 | A | 3/1980 |
| IE | 904353 | A1 | 10/1991 |
| IL | 128709 | A | 9/2004 |
| JP | S4846180 | A | 7/1973 |
| JP | S5397289 | A | 8/1978 |
| JP | S56109643 | A | 8/1981 |
| JP | S5789869 | A | 6/1982 |
| JP | S6458241 | A | 3/1989 |
| JP | H0363570 | A | 3/1991 |
| JP | H05501071 | A | 3/1993 |
| JP | H0551222 | B2 | 8/1993 |
| JP | H06500403 | A | 1/1994 |
| JP | H0716219 | A | 1/1995 |
| JP | H0910302 | A | 1/1997 |
| JP | H0951947 | A | 2/1997 |
| JP | H09229828 | A | 9/1997 |
| JP | H10153531 | A | 6/1998 |
| JP | H10211274 | A | 8/1998 |
| JP | H1156821 | A | 3/1999 |
| JP | H1176397 | A | 3/1999 |
| JP | H11197236 | A | 7/1999 |
| JP | 2001159630 | A | 6/2001 |
| JP | 2001161668 | A | 6/2001 |
| JP | 2001276181 | A | 10/2001 |
| JP | 3231086 | B2 | 11/2001 |
| JP | 2002116201 | A | 4/2002 |
| JP | 2002272710 | A | 9/2002 |
| JP | 2002528159 | A | 9/2002 |
| JP | 2003126068 | A | 5/2003 |
| JP | 2005237617 | A | 9/2005 |
| JP | 2006026327 | A | 2/2006 |
| JP | 3813974 | B2 | 8/2006 |
| JP | 2007175534 | A | 7/2007 |
| JP | 2008149076 | A | 7/2008 |
| JP | 2008206734 | A | 9/2008 |
| JP | 2009525819 | A | 7/2009 |
| JP | 2009536554 | A | 10/2009 |
| JP | 4382322 | B2 | 12/2009 |
| JP | 2010514501 | A | 5/2010 |
| JP | 2010524505 | A | 7/2010 |
| JP | 2010189415 | A | 9/2010 |
| JP | 4573538 | B2 | 11/2010 |
| JP | 2010536014 | A | 11/2010 |
| JP | 2011512987 | A | 4/2011 |
| JP | 4861649 | B2 | 1/2012 |
| JP | 4869910 | B2 | 2/2012 |
| JP | 5344252 | B2 | 11/2013 |
| JP | 5620541 | B2 | 11/2014 |
| JP | 2015014552 | A | 1/2015 |
| JP | 2015519145 | A | 7/2015 |
| JP | 2015215355 | A | 12/2015 |
| JP | 2016500278 | A | 1/2016 |
| JP | 2016504075 | A | 2/2016 |
| JP | 2016520827 | A | 7/2016 |
| JP | 2016523591 | A | 8/2016 |
| JP | 5997760 | B2 | 9/2016 |
| JP | 2016527939 | A | 9/2016 |
| JP | 6194415 | B2 | 9/2017 |
| JP | 2018110967 | A | 7/2018 |
| JP | 2018525191 | A | 9/2018 |
| JP | 2020513906 | A | 5/2020 |
| JP | 7204742 | B2 | 1/2023 |
| KR | 20120030087 | A | 3/2012 |
| KR | 101134279 | B1 | 4/2012 |
| KR | 20160088853 | A | 7/2016 |
| TW | 200528066 | A | 9/2005 |
| WO | WO-1984003213 | A1 | 8/1984 |
| WO | WO-8605568 | A1 | 9/1986 |
| WO | WO-9004351 | A1 | 5/1990 |
| WO | WO-9118632 | A1 | 12/1991 |
| WO | WO-9216144 | A1 | 10/1992 |
| WO | WO-9407415 | A1 | 4/1994 |
| WO | WO-1994012093 | A1 | 6/1994 |
| WO | WO-9415665 | A1 | 7/1994 |
| WO | WO-9511712 | A1 | 5/1995 |
| WO | WO-9516395 | A1 | 6/1995 |
| WO | WO-1995021639 | A1 | 8/1995 |
| WO | WO-9524176 | A1 | 9/1995 |
| WO | WO-9621853 | A1 | 7/1996 |
| WO | WO-9718845 | A1 | 5/1997 |
| WO | WO-1997045714 | A1 | 12/1997 |
| WO | WO-1998034532 | A1 | 8/1998 |
| WO | WO-9846136 | A1 | 10/1998 |
| WO | WO-9913925 | A1 | 3/1999 |
| WO | WO-1999029232 | A1 | 6/1999 |
| WO | WO-9948425 | A1 | 9/1999 |
| WO | WO-9955232 | A1 | 11/1999 |
| WO | WO-2000024313 | A1 | 5/2000 |
| WO | WO-0040291 | A1 | 7/2000 |
| WO | WO-0041624 | A1 | 7/2000 |
| WO | WO-0108546 | A2 | 2/2001 |
| WO | WO-0191829 | A2 | 12/2001 |
| WO | WO-2002028457 | A1 | 4/2002 |
| WO | WO-0245813 | A1 | 6/2002 |
| WO | WO-02051520 | A1 | 7/2002 |
| WO | WO-03008012 | A2 | 1/2003 |
| WO | WO-03041767 | A1 | 5/2003 |
| WO | WO-03047660 | A1 | 6/2003 |
| WO | WO-03078964 | A2 | 9/2003 |
| WO | WO-03085395 | A1 | 10/2003 |
| WO | WO-2003092573 | A2 | 11/2003 |
| WO | WO-2004082467 | A2 | 9/2004 |
| WO | WO-2004103565 | A2 | 12/2004 |
| WO | WO-2005068011 | A1 | 7/2005 |
| WO | WO-2006031500 | A2 | 3/2006 |
| WO | WO-2006124634 | A1 | 11/2006 |
| WO | WO-2007033319 | A1 | 3/2007 |
| WO | WO-2008028165 | A2 | 3/2008 |
| WO | WO-2008047699 | A1 | 4/2008 |
| WO | WO-2008077047 | A2 | 6/2008 |
| WO | WO-2008101025 | A1 | 8/2008 |
| WO | WO-2008157511 | A1 | 12/2008 |
| WO | WO-2009094345 | A1 | 7/2009 |
| WO | WO-2009113999 | A2 | 9/2009 |
| WO | WO-2010087216 | A1 | 8/2010 |
| WO | WO-2011030282 | A1 | 3/2011 |
| WO | WO-2011050110 | A1 | 4/2011 |
| WO | WO-2011069145 | A2 | 6/2011 |
| WO | WO-2011114413 | A1 | 9/2011 |
| WO | WO-2011123685 | A2 | 10/2011 |
| WO | WO-2011162772 | A1 | 12/2011 |
| WO | WO-2012012127 | A2 | 1/2012 |
| WO | WO-2012114105 | A1 | 8/2012 |
| WO | WO-2013181352 | A1 | 12/2013 |
| WO | WO-2014022275 | A1 | 2/2014 |
| WO | WO-2014022750 | A1 | 2/2014 |
| WO | WO-2014058945 | A1 | 4/2014 |
| WO | WO-2014085800 | A1 | 6/2014 |
| WO | WO-2014089186 | A1 | 6/2014 |
| WO | WO-2014099266 | A2 | 6/2014 |
| WO | WO-2015091818 | A1 | 6/2015 |
| WO | WO-2016027782 | A1 | 2/2016 |
| WO | WO-2016054252 | A1 | 4/2016 |
| WO | WO-2016201406 | A1 | 12/2016 |
| WO | WO-2017019552 | A1 | 2/2017 |
| WO | WO-2017041087 | A1 | 3/2017 |
| WO | WO-2017133953 | A1 | 8/2017 |
| WO | WO-2017218840 | A1 | 12/2017 |
| WO | WO-2017218848 | A1 | 12/2017 |
| WO | WO-2018125929 | A1 | 7/2018 |
| WO | WO-2018227191 | A1 | 12/2018 |

(56) References Cited

FOREIGN PATENT DOCUMENTS

| | | | |
|---|---|---|---|
| WO | WO-2019055487 | A1 | 3/2019 |
| WO | WO-2019113505 | A1 | 6/2019 |
| WO | WO-2019232196 | A1 | 12/2019 |
| WO | WO-2020163744 | A1 | 8/2020 |
| WO | WO-2020185914 | A1 | 9/2020 |
| WO | WO-2020227701 | A1 | 11/2020 |
| WO | WO-2021119487 | A1 | 6/2021 |
| WO | WO-2022203747 | A1 | 9/2022 |

OTHER PUBLICATIONS

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.
Barnard, D. R. & Arthur, M. M., "Fibronectin (cold insoluble globulin) in the neonate," Clinical and Laboratory Observations, 102(3): 453-455 (1983).
Bauman et al., "Don't Stick Me Again! Reducing Blood Culture Contamination," INOVA Fairfax Medical Campus, Emergency Department (2019), 1 page.
Baxter, "IV Tubing and Access Devices" authored by and published by Baxter, dated Nov. 6, 2006, 105 pages.
BD Saf-T-Intima Closed IV Catheter System, Becton, Dickinson and Company, 2015 Brochure. Retrieved from the Internet (Sep. 11, 2019) https://www.bd.com/en-us/offerings/capabilities/infusion-therapy/iv-catheters/bd-saf-tintima-closed-iv-catheter-system, 2 pages.
BD Vacutainer Passive Shielding Blood Collection Needle Brochure; Becton Dickinson and Company (2005), 2 pages.
Bell et al., Effectiveness of a Novel Specimen Collection System in Reducing Blood Culture Contamination Rates, J. Emergency Nursing, vol. 44, No. 6, 570 (Nov. 2018), 6 pages.
Blakeney, "Reduction of Blood Culture Contaminations Using Initial Specimen Diversion Device," Beebe Healthcare (Jun. 2018), 1 page.
Brecher, M. E. et al., "Bacterial Contamination of Blood Components," Clinical Microbiology Reviews, 18(1):195-204 (2005).
Brownfield et al., "Emergency Department Observes 83% Reduction in Blood Culture Contamination with Initial Specimen Diversion Technology Adoption," Am. J. Infection Control, vol. 49, S14, ADS 34 (Jun. 2021), 1 page.
Calam, R. R., "Recommended 'Order of Draw' for Collecting Blood Specimens Into Additive-Containing Tubes," Letter to the Editor, Clinical Chemistry, 28(6):1399 (1982), 1 page.
Cartridge and Test Information, Abbott, Art: 714258-010 Rev. Date: Aug. 15, 2016, 6 pages.
Case 1: 19-cv-00097-CFC-CJB, *Magnolia Medical Technologies, Inc.*, Plaintiff v. *Kurin, Inc.*, Defendant; Memorandum Opinion, (Document 514) filed Aug. 4, 2023, 38 pages.
Case 1: 19-cv-00097-CFC-CJB, *Magnolia Medical Technologies, Inc.*, Plaintiff v. *Kurin, Inc.*, Defendant; Order, (Document 515) filed Aug. 4, 2023, 1 page.
Case 1: 19-cv-00097-CFC-CJB, *Magnolia Medical Technologies, Inc.*, Plaintiff v. *Kurin, Inc.*, Defendant; Order, (Document 516) filed Aug. 4, 2023, 2 pages.
Challiner, A. et al., Queen Alexandra Hospital, Portsmouth P06 3LY, "Venous/arterial blood management protection system," Anaesthesia, Correspondence (Feb. 1992); 47(2), p. 169.
Chang et al., "Impact of Blood Culture Diversion Device and Molecular Pathogen Identification on Vancomycin Use," San Antonio Military Medical Center (2016), 1 page.
Chinese Office Action and Search Report for Chinese Application No. 202080033513.6, dated Oct. 9, 2022, 19 pages with English translation.
Claim Construction Order, *Magnolia Medical Techs*. v. *Kurin*, Case No. 19-00097-CFC-CJB, at 3 (D. Del.) (May 20, 2020), 4 pages.
De Korte, D. et al., "Diversion of first blood volume results in a reduction of bacterial contamination for whole-blood collections," Vox Sanguinis, 83:13-16 (2002).
De Korte, D. et al., "Effects of skin disinfection method, deviation bag, and bacterial screening on clinical safety of platelet transfusions in the Netherlands," Transfusion, 46:476-485 (2006).
Declaration of Dr. Morten Jensen under 37 C.F.R. § 1.132, Oct. 10, 2023, 400 pages.
Doern et al., "A Comprehensive Update on the Problem of Blood Culture Contamination and a Discussion of Methods for Addressing the Problem," Clinical Microbiology, vol. 33, No. 1, e00009-19 (Jan. 2020), 21 pages.
Edwards Lifesciences, "Conservation. Safety. Simplicity. Edwards VAMP and VAMP Jr. Systems," 2002 Brochure. Retrieved from the Internet (Sep. 11, 2019) https://www.medline.com/media/catalog/Docs/MKT/VAMPSYSTEMBROCHURE.PDF, 4 pages.
Ernst, D. J. et al., "NCCLS simplifies the order of draw: a brief history," MLO, pp. 26-27 (2004).
European Examination Report for EP Application No. 20716348.6, dated Jul. 12, 2022, 7 pages.
Extended European Search Report for European Application No. 23218666.8 dated Apr. 18, 2024, 9 pages.
Extended European Search Report for European Application No. EP 2023029844.2 dated Mar. 20, 2024, 9 pages.
Extended European Search Report for European Application No. EP23182529 dated Dec. 19, 2023, 13 pages.
Geisler et al., "Model to Evaluate the Impact of Hospital-Based Interventions Targeting False-Positive Blood Cultures on Economic and Clinical Outcomes," J. Hospital Infection, vol. 102, No. 4, pp. 438-444 (Mar. 2019).
Gottlieb, T., "Hazards of Bacterial Contamination of Blood Products," Anaesth Intens Care, 21:20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, pp. 575-589 (2003).
International Preliminary Report on Patentability for Application No. PCT/US2020/022125, mailed on Sep. 23, 2021, 14 Pages.
JP Application No. 2021-552145 Notice of Reasons for Rejection dated Jan. 9, 2024, mailed Jan. 15, 2024, 9 pages.
JP Application No. 2023-075104 Notice of Reasons for Rejection dated Feb. 29, 2024, mailed Mar. 5, 2024, with English Translation, 9 pages.
Kim, J. Y. et al., "The Sum of the Parts is Greater Than the Whole: Reducing Blood Culture Contamination," Annals of Internal Medicine, 154:202-203 (2011).
Lanteri et al., "Reduction of Blood Culture Contaminations in the Emergency Department," Department of Emergency Medicine, San Antonio Military Medical Center (2016), 1 page.
Levin, P. D. et al., "Use of the Nonwire Central Line Hub to Reduce Blood Culture Contamination," Chest, 143(3):640-645 (2013).
Liumbruno, G. M. et al., "Reduction of the risk of bacterial contamination of blood components through diversion of the first part of the donation of blood and blood components," Blood Transfus, 7: 86-93 (2009).
Li, Y. et al., "Direct labeling and visualization of blood vessels with lipophilic carbocyanine dye Oil," Nature Protocols, 3(11):1703-1708 (2008).
Mayer, G. A, "A Method for the Reliable Determination of Clotting Time in Whole Blood," Can Med Assoc J., 72(12):927-929 (1955).
McDonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2):29-31 (1963).
Murphy, M., "Better Blood Transfusion," Journal of the Intensive Core Society, 4(3):78-80 (2003).
Napolitano, M. et al., "Quality control of bacterial contamination of blood components: the feasibility of diversion system testing," Blood Transfus, 2:231-232 (2004).
Nielsen et al., "Initial Specimen Diversion Device Reduces Blood Culture Contamination and Vancomycin Use in Academic Medical Centre," J. Hospital Infection, vol. 120:127-133 (Feb. 2022).

(56) References Cited

OTHER PUBLICATIONS

Non-Final Office Action for U.S. Appl. No. 16/815,526 mailed on Aug. 18, 2022, 13 pages.
Non-Final Office Action for U.S. Appl. No. 18/227,185 dated Apr. 18, 2024, 18 pages.
Norberg, A et al., "Contamination Rates of Blood Cultures Obtained by Dedicated Phlebotomy vs Intravenous Catheter," JAMA, 289(6):726-729 (2003).
Notice of Reasons for Rejection for Japanese Application No. 2022-149585, dated Sep. 26, 2023, 9 pages.
Office Action in Ex Parte Reexamination for U.S. Appl. No. 90/019,177, dated Aug. 9, 2023, 11 pages.
Order of Draw for Multiple Tube Collections, LabNotes, a newsletter from BD Diagnostics,—Preanalytical Systems, 17(1):3 (2007), 1 page.
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Pall Corp., "Leukotrap Filtration Systems for Whole Blood Derived Platelets: Leukotrap RC PL and Leukotrap PL Systems," 2005 Brochure, 2 pages.
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Povroznik, "Initial Specimen Diversion Device Utilization Mitigates Blood Culture Contamination Across Regional Community Hospital and Acute Care Facility," Am. J. Medical Quality, vol. 37, No. 5, 405 (Mar. 2022), 8 pages.
Proehl, J. A et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Rupp et al., "Reduction in Blood Culture Contamination Through Use of Initial Specimen Diversion Device," Clinical Infectious Diseases, vol. 65, No. 2, 201 (Jul. 15, 2017), 19 pages.
Schuur, J., "Blood Cultures: When Do they Help and When Do They Harm?" Brigham & Women's Hospital, Department of Emergency Medicine, (Jun. 21-23, 2012), 42 pages.
Sheppard, C. A et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1):11-19 (2000).
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Skoglund et al., "Estimated Clinical and Economic Impact through Use of a Novel Blood Collection Device To Reduce Blood Culture Contamination in the Emergency Department: a Cost-Benefit Analysis," J Clin Microbiol. (Jan. 2019); 57(1):e01015-18, 10 pages.
Steed et al., "Study Demonstrates Reduction in Blood Culture Contamination Rates with Novel Blood Culture Collection Device," Clinical Lab Products Magazine (Feb. 2018), 2 pages.
Stohl, S. et al., "Blood Cultures at Central Line Insertion in the Intensive Care Unit: Comparison with Peripheral Venipuncture," Journal of Clinical Microbiology, 49(7):2398-2403 (2011).
Tang, M. et al., "Closed Blood Conservation Device for Reducing Catheter-Related Infections in Children After Cardiac Surgery," Critical Care Nurse, 34(5):53-61 (2014).
Tompkins et al., "Getting to Zero: Impact of A Device To Reduce Blood Culture Contamination and False-Positive Central-Line-Associated Bloodstream Infection," Infection Control & Hospital Epidemiology, pp. 1-5 (Nov. 2022).
Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.
U.S. Appl. No. 18/399,007 Non-Final Office Action dated Mar. 7, 2024, 8 pages.
U.S. Appl. No. 18/407,010 Non-Final Office Action dated Mar. 13, 2024, 8 pages.
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23: pp. 63-66 (2012).
Weinbaum, F. I. et al., "Doing It Right the First Time: Quality Improvement and the Contaminant Blood Culture," Journal of Clinical Microbiology, 35(3):563-565 (1997).
Weinstein, M.P., "Current Blood Culture Methods and Systems: Clinical Concepts, Technology, and Interpretation of Results," Clinical Infectious Diseases, 23:40-46 (1996).
Weinstein, M.P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Weinstein, M.P., "Minireview: Blood Culture Contamination: Persisting Problems and Partial Progress," Journal of Clinical Microbiology, 41(6):2275-2278 (2003).
Ziegler, et al., "Controlled Clinical Laboratory Comparison of Two Supplemented Aerobic and Anaerobic Media Used in Automated Blood Culture Systems To Detect Bloodstream Infections," J. Clinical Microbiology, 36(3):657-661 (1998).
Zimmerman et al., "Reducing Blood Culture Contamination Using an Initial Specimen Diversion Device," Am. J. Infection Control, vol. 47, No. 7, pp. 822-826 (Jan. 2019).
Zimmon, D. S. et al., "Effect of Portal Venous Blood Flow Diversion on Portal Pressure," J Clin Invest, 65(6): 1388-1397 (1980).
Zundert, A V., "New Closed IV Catheter System," Acta Anaesth. Belg., 56:283-285 (2005).
AU Application No. 2013267448, Office Action mailed Nov. 5, 2016; Applicant Magnolia Medical Technologies, Inc.; 3 pages.
AU Application No. 2017216493, Office Action mailed Sep. 19, 2018; Applicant Magnolia Medical Technologies, Inc.; 2 pages.
AU Application No. 2018279941, Office Action mailed Mar. 20, 2023; Applicant Magnolia Medical Technologies, Inc.; 3 pages.
AU Application No. 2018334138, Office Action mailed Jun. 24, 2023; Applicant Magnolia Medical Technologies, Inc.; 3 pages.
AU Application No. 2019204941, Office Action mailed Jul. 15, 2019; Applicant Magnolia Medical Technologies, Inc.; 4 pages.
AU Application No. 2020213415, Office Action mailed May 21, 2021; Applicant Magnolia Medical Technologies, Inc.; 3 pages.
AU Application No. 2020218544, Office Action mailed Jul. 31, 2024; Applicant Magnolia Medical Technologies, Inc.; 3 pages.
AU Application No. 2020234829, Office Action mailed Nov. 15, 2024; Applicant Magnolia Medical Technologies, Inc.; 3 pages.
AU Application No. 2020234829, Office Action mailed Sep. 11, 2025; Applicant Magnolia Medical Technologies, Inc.; 3 pages.
AU Application No. 2022200818, Office Action mailed May 11, 2023; Applicant Magnolia Medical Technologies, Inc.; 4 pages.
AU Application No. 2024203105, Office Action mailed Jan. 21, 2025; Applicant Magnolia Medical Technologies, Inc.; 3 pages.
AU Application No. 2024203140, Office Action mailed Apr. 8, 2025; Applicant Magnolia Medical Technologies, Inc.; 4 pages.
AU Application No. 2024205062, Office Action mailed Sep. 8, 2025; Applicant Magnolia Medical Technologies, Inc.; 2 pages.
Author Unknown, "BACT/Alert® Culture Media: Strong Outside, Strong Inside," [website], Biomerieux, (Publication Date Unknown), [Accessed via Internet, publicly available at URL: https://www.biomerieux.com/us/en/our-offer/clinical-products/bact-alert-culture-media-bottles.html.], 10 pages.
Author Unknown, "BD Bactec™ Blood Culture System," [website], Becton, Dickinson and Company, (Publication Date Unknown),

(56) References Cited

OTHER PUBLICATIONS

[Accessed via Internet, publicly available at URL: https://www.bd.com/en-us/products-and-solutions/products/product-families/bd-bactec-blood-culture-system.], 9 pages.
Author Unknown, "Changing Blood Culture Collection in Hospitals Across America, Clinical Evidence, Studies," [website], KURIN, (Publication Date Unknown), [Retrieved from Internet on Sep. 15, 2025 at URL: https://www.kurin.com/studies/.], 22 pages.
Author Unknown, "Changing Blood Culture Collection in Hospitals Across America," [website], Kurin, (Publication Date Unknown), [Retrieved from Internet on Sep. 15, 2025 at URL: https://www.kurin.com/clinical-guidelines/.], 11 pages.
Author Unknown, "False Positive Blood Cultures—Improve the accuracy of blood culture," [website], Kurin, (Publication Date Unknown), [Retrieved from Internet on Sep. 15, 2025 at URL: https://www.kurin.com/false-positive-blood-cultures/.], 5 pages.
Author Unknown, "Kurin® Jet™ Blood Culture Collection Ordering Information," [website], Kurin, (Publication Date Unknown), [Accessed via Internet, publicly available at URL: https://www.kurin.com/kurin-jet/.], 2 pages.
Author Unknown, "Kurin Launches Kurin Jet, Redefining the Blood Culture Contamination Device Market," [website], Kurin, (Publication Date Unknown), [Accessed via Internet, publicly available at URL: https://www.kurin.com/kurin-launches-kurin-jet-redefining-the-blood-culture-contamination-device-market/.], 5 pages.
Author Unknown, "Kurin Lock® with Flash Technology: Better than conventional diversion," [website], Kurin, (Publication Date Unknown), [Retrieved from Internet on Sep. 26, 2025 at URL: https://www.kurin.com/kurin-jet/.], 10 pages.
Author Unknown, "Lowering the 3% Blood Culture Contamination Rate Benchmark," [website], Kurin, (Publication Date Unknown), [Retrieved from Internet on Sep. 15, 2025 at URL: https://www.kurin.com/3-percent-standard/.], 4 pages.
Author Unknown, "Newly Released CLSI National Blood Culture Guidelines Identify Best Practices and Evidence-Based Technology Solutions Such as Steripath® to Improve Patient Safety and Outcomes," [website], Magnolia Medical Technologies, Inc., (May 5, 2022), [Retrieved from Internet on Sep. 15, 2025 at URL: https://magnolia-medical.com/news/newly-released-cisi-national-blood-culture-guidelines-identify-best-practices-and-evidence-based-technology-solutions-such-as-steripath-to-improve-patient-safety-and-outcomes/.], 5 pages.
Author Unknown, "The Financial and Clinical Costs of False Positive Blood Cultures," [website], Kurin, (Publication Date Unknown), [Retrieved from Internet on Sep. 15, 2025 at URL: https://www.kurin.com/false-positives-blood-culture-cost/.], 5 pages.
Avatar: "Is it safe to reinfuse blood drawn from a CVAD via a syringe when checking line patency or drawing blood?" [retrieved online Jul. 31, 2024] URL:https://www.avatargroup.org.au/faq---blood-collection.html, 4 pages.
Bruneau et al., "Efficacy of a New Collection Procedure for Preventing Bacterial Contamination of Whole-blood Donations," Transfusion, 41(1):74-81, (Jan. 2001).
Buzard, B.A. et al., "Evaluation of an Initial Specimen Diversion Device (ISDD) on Rates of Blood Culture Contamination in the Emergency Department," Kans J Med. Mar. 19, 2021; 14(1): 73-76. eCollection 2021.
CA Application No. 2875118, Office Action mailed Apr. 7, 2020; Applicant Magnolia Medical Technologies, Inc. et al; 4 pages.
CA Application No. 2875118, Office Action mailed Mar. 21, 2019; Applicant Magnolia Medical Technologies, Inc. et al; 5 pages.
CA Application No. 2931983, Office Action mailed Oct. 1, 2020; Applicant Magnolia Medical Technologies, Inc.; 3 pages.
CA Application No. 2931983, Office Action mailed Oct. 16, 2019; Applicant Magnolia Medical Technologies, Inc.; 4 pages.
CA Application No. 2932536, Office Action mailed Jul. 13, 2021; Applicant Magnolia Medical Technologies, Inc.; 4 pages.
CA Application No. 2932536, Office Action mailed Nov. 8, 2019; Applicant Magnolia Medical Technologies, Inc.; 6 pages.
CA Application No. 2932536, Office Action mailed Oct. 23, 2020; Applicant Magnolia Medical Technologies, Inc.; 6 pages.
CA Application No. 3066670, Office Action mailed Oct. 4, 2024; Applicant Magnolia Medical Technologies, Inc. et al; 4 pages.
CA Application No. 3074105, Office Action mailed Nov. 15, 2024; Applicant Magnolia Medical Technologies, Inc.; 5 pages.
CA Application No. 3087992, Office Action mailed Apr. 9, 2026; Applicant Magnolia Medical Technologies, Inc.; 6 total pages.
CA Application No. 3087992, Office Action mailed Mar. 20, 2025; Applicant Magnolia Medical Technologies, Inc.; 4 pages.
CA Application No. 3101972, Office Action mailed May 13, 2025; Applicant Magnolia Medical Technologies, Inc.; 4 pages.
CA Application No. 3120161, Office Action mailed Jun. 20, 2022; Applicant Magnolia Medical Technologies, Inc.; 4 pages.
CA Application No. 3129065, Office Action mailed Feb. 11, 2025; Applicant Magnolia Medical Technologies, Inc.; 3 pages.
CA Application No. 3132981, Office Action mailed Aug. 22, 2025; Applicant Magnolia Medical Technologies, Inc.; 5 pages.
CA Application No. 3136331, Office Action mailed Feb. 21, 2023; Applicant Magnolia Medical Technologies, Inc.; 4 pages.
CA Application No. 3164339, Office Action mailed Jan. 26, 2026; Applicant Magnolia Medical Technologies, Inc.; 4 pages.
CA Application No. 3183294, Office Action mailed Aug. 19, 2024; Applicant Magnolia Medical Technologies, Inc.; 5 pages.
Callado, G. Y. et al., "Diagnostic Stewardship: A Systematic Review and Meta-analysis of Blood Collection Diversion Devices Used to Reduce Blood Culture Contamination and Improve the Accuracy of Diagnosis in Clinical Settings," Open Forum Infect Dis. Aug. 11, 2023; 10(9): ofad433, 10 pages. eCollection Sep. 2023.
Chamarthy, P., et al.; "Mixing Characteristics in a Serpentine Micro-Channel," IMECE2004-61902; Proceedings of the ASME 2004 International Mechanical Engineering Congress and Exposition. Fluids Engineering. Anaheim, California, USA; Nov. 13-19, 2004, pp. 253-261; Exhibit 4; 10 pages.
CN Application No. 201380040468.7, Office Action mailed Apr. 12, 2017; Applicant Magnolia Medical Technologies, Inc., with English Translation; 8 pages.
CN Application No. 201380040468.7, Office Action mailed Jun. 30, 2016; Applicant Magnolia Medical Technologies, Inc., with English Translation; 9 pages.
CN Application No. 201380071681.4, Office Action mailed Aug. 16, 2016; Applicant Magnolia Medical Technologies, Inc., with English Translation; 16 pages.
CN Application No. 201380071681.4, Office Action mailed Jun. 28, 2017; Applicant Magnolia Medical Technologies, Inc., with English Translation; 22 pages.
CN Application No. 201380072185.0, Office Action mailed Sep. 28, 2016; Applicant Magnolia Medical Technologies, Inc., with English Translation; 17 pages.
CN Application No. 201711078173.5, Office Action mailed Feb. 3, 2020; Applicant Magnolia Medical Technologies, Inc., with English Translation; 14 pages.
CN Application No. 201811146373.4, Office Action mailed Apr. 8, 2025; Applicant Magnolia Medical Technologies, Inc., with English Translation; 18 pages.
CN Application No. 201811146373.4, Office Action mailed Aug. 25, 2021; Applicant Magnolia Medical Technologies, Inc., with English Translation; 10 pages.
CN Application No. 201811146373.4, Office Action mailed Jan. 29, 2022; Applicant Magnolia Medical Technologies, Inc., with English Translation; 21 pages.
CN Application No. 201811146373.4, Office Action mailed Jul. 28, 2025; Applicant Magnolia Medical Technologies, Inc., with English Translation; 36 pages.
CN Application No. 201811146373.4, Office Action mailed Nov. 4, 2020; Applicant Magnolia Medical Technologies, Inc., with English Translation; 17 pages.
CN Application No. 201880050862.1, Office Action mailed Mar. 14, 2022; Applicant Magnolia Medical Technologies, Inc., with English Translation; 19 pages.
CN Application No. 201880066848.0, Office Action mailed Apr. 20, 2022; Applicant Magnolia Medical Technologies, Inc., with English Translation; 20 pages.

(56) References Cited

OTHER PUBLICATIONS

CN Application No. 201880088771.7, Office Action mailed May 7, 2022; Applicant Magnolia Medical Technologies, Inc., with English Translation; 5 pages.
CN Application No. 201880088771.7, Office Action mailed Sep. 3, 2021; Applicant Magnolia Medical Technologies, Inc., with English Translation; 17 pages.
CN Application No. 202011295348.X, Office Action mailed Nov. 29, 2023; Applicant Magnolia Medical Technologies, Inc., with English Translation; 10 pages.
CN Application No. 202080025953.7, Office Action mailed Aug. 28, 2024; Applicant Magnolia Medical Technologies, Inc., with English Translation; 26 pages.
CN Application No. 202080025953.7, Office Action mailed Dec. 17, 2024; Applicant Magnolia Medical Technologies, Inc., with English Translation; 22 pages.
CN Application No. 202080025953.7, Office Action mailed Jan. 9, 2024; Applicant Magnolia Medical Technologies, Inc., with English Translation; 27 pages.
CN Application No. 202080025953.7, Office Action mailed May 24, 2025; Applicant Magnolia Medical Technologies, Inc., with English Translation; 12 pages.
CN Application No. 202080094860.X, Office Action mailed Jan. 10, 2025; Applicant Magnolia Medical Technologies, Inc., with English Translation; 20 pages.
CN Application No. 202310257287.5, Office Action mailed Apr. 23, 2025; Applicant Magnolia Medical Technologies, Inc., with English Translation; 21 pages.
CN Application No. 202311117448.7, Office Action mailed Apr. 1, 2026; Applicant Magnolia Medical Technologies, Inc., with English Translation; 11 pages.
ENA (Emergency Nurses Association), "Clinical Practice Guideline: Synopsis—Prevention of Blood Culture Contamination," [website], Guidelinecentral, (May 8, 2018; last updated Oct. 18, 2025), [Accessed via Internet, publicly available at URL: https://www.guidelinecentral.com/guideline/308349/#section-420.], 1 page.
EP Application No. 13797732.8, Supplementary European Search Report mailed Dec. 7, 2015; Applicant Magnolia Medical Technologies, Inc et al.; 5 pages.
EP Application No. 13845555.5, Supplementary European Search Report mailed Jul. 12, 2016; Applicant Magnolia Medical Technologies, Inc.; 6 pages.
EP Application No. 13859067.4, Extended European Search Report mailed Aug. 16, 2017; Applicant Magnolia Medical Technologies, Inc.; 6 pages.
EP Application No. 13859067.4, Extended European Search Report mailed Jan. 27, 2017; Applicant Magnolia Medical Technologies, Inc.; 4 pages.
EP Application No. 13859067.4, Extended European Search Report mailed Jun. 7, 2016; Applicant Magnolia Medical Technologies, Inc.; 4 pages.
EP Application No. 13860741.1, Supplementary European Search Report mailed Jun. 7, 2016; Applicant Magnolia Medical Technologies, Inc.; 5 pages.
EP Application No. 16200112.7, Extended European Search Report mailed Feb. 15, 2018; Applicant Magnolia Medical Technologies, Inc.; 3 pages.
EP Application No. 16200112.7, Extended European Search Report mailed Mar. 1, 2017; Applicant Magnolia Medical Technologies, Inc.; 6 pages.
EP Application No. 16808502.5, Extended European Search Report mailed Jan. 23, 2019; Applicant Bullington, Gregory J. et al.; 5 pages.
EP Application No. 16843182.3, Extended European Search Report mailed Mar. 26, 2019; Applicant Magnolia Medical Technologies, Inc.; 4 pages.
EP Application No. 17204012.3, Extended European Search Report mailed Feb. 14, 2018; Applicant Magnolia Medical Technologies, Inc.; 7 pages.
EP Application No. 17206745.6, Extended European Search Report mailed Feb. 19, 2018; Applicant Magnolia Medical Technologies, Inc.; 8 pages.
EP Application No. 17206745.6, Office Action mailed Feb. 18, 2020; Applicant Magnolia Medical Technologies, Inc.; 4 pages.
EP Application No. 18188136.8, Extended European Search Report mailed May 16, 2019; Applicant Magnolia Medical Technologies, Inc.; 9 pages.
EP Application No. 18813278.1, Extended European Search Report mailed Feb. 17, 2021; Applicant Magnolia Medical Technologies, Inc.; 4 pages.
EP Application No. 18855938.9, Extended European Search Report mailed Aug. 2, 2021; Applicant Magnolia Medical Technologies, Inc.; 7 pages.
EP Application No. 18885543.1, Extended European Search Report mailed Oct. 8, 2021; Applicant Magnolia Medical Technologies, Inc.; 8 pages.
EP Application No. 19156636.3, Extended European Search Report mailed Aug. 27, 2019; Applicant Magnolia Medical Technologies, Inc.; 7 pages.
EP Application No. 19190772.4, Extended European Search Report mailed Feb. 10, 2020; Applicant Magnolia Medical Technologies, Inc.; 7 pages.
EP Application No. 20167572.5, Extended European Search Report mailed Sep. 30, 2020; Applicant Magnolia Medical Technologies, Inc.; 10 pages.
EP Application No. 20176877.7, Extended European Search Report mailed Dec. 1, 2020; Applicant Magnolia Medical Technologies, Inc.; 9 pages.
EP Application No. 20207898.6, Extended European Search Report mailed Aug. 30, 2021; Applicant Magnolia Medical Technologies, Inc.; 8 pages.
EP Application No. 20709440.0, Office Action mailed Feb. 18, 2025; Applicant Magnolia Medical Technologies, Inc.; 6 pages.
EP Application No. 21167069.0, Extended European Search Report mailed Nov. 10, 2021; Applicant Magnolia Medical Technologies, Inc.; 9 pages.
EP Application No. 21167625.9, Extended European Search Report mailed Oct. 8, 2021; Applicant Magnolia Medical Technologies, Inc.; 7 pages.
EP Application No. 21197514.9, Extended European Search Report mailed Mar. 30, 2022; Applicant Magnolia Medical Technologies, Inc.; 9 pages.
EP Application No. 22158983.1, Extended European Search Report mailed Aug. 1, 2022; Applicant Magnolia Medical Technologies, Inc.; 8 pages.
EP Application No. 22172183.0, Extended European Search Report mailed Nov. 9, 2022; Applicant Magnolia Medical Technologies, Inc.; 7 pages.
EP Application No. 22194769.0, Extended European Search Report mailed Feb. 28, 2023; Applicant Magnolia Medical Technologies, Inc.; 9 pages.
EP Application No. 22210589.2, Extended European Search Report mailed Apr. 17, 2023; Applicant Magnolia Medical Technologies, Inc.; 6 pages.
EP Application No. 23153164.1, Extended European Search Report mailed Aug. 7, 2023; Applicant Magnolia Medical Technologies, Inc.; 8 pages.
EP Application No. 23171135.9, Extended European Search Report mailed Oct. 30, 2023; Applicant Magnolia Medical Technologies, Inc.; 8 pages.
EP Application No. 23173044.1, Extended European Search Report mailed Oct. 27, 2023; Applicant Magnolia Medical Technologies, Inc.; 8 pages.
EP Application No. 23182529.0, Office Action mailed Apr. 16, 2026; Applicant Magnolia Medical Technologies, Inc.; 6 pages.
EP Application No. 23182529.0, Office Action mailed Jul. 29, 2025; Applicant Magnolia Medical Technologies, Inc.; 6 pages.
EP Application No. 23217471.4, Extended European Search Report mailed May 22, 2024; Applicant Magnolia Medical Technologies, Inc.; 8 pages.

(56) References Cited

OTHER PUBLICATIONS

EP Application No. 24217446.4, Extended European Search Report mailed Apr. 17, 2025; Applicant Magnolia Medical Technologies, Inc.; 8 pages.
EP Application No. 25164992.7, Extended European Search Report mailed Aug. 26, 2025; Applicant Magnolia Medical Technologies, Inc.; 8 pages.
Garstecki et al., "Formation of Droplets and Bubbles in a Microfluidic T-Junction—Scaling and Mechanism of Break-Up," Lab on a Chip, 6(3):437-446, (Mar. 2006).
GB Application No. 1506837.2, Office Action mailed Jul. 19, 2017; Applicant Magnolia Medical Technologies, Inc.; 6 pages.
GB Application No. 1805101.1, Office Action mailed May 25, 2018; Applicant Magnolia Medical Technologies, Inc.; 8 pages.
IL Application No. 238991, Office Action mailed Feb. 13, 2020; Applicant Magnolia Medical Technologies, Inc., with English Translation; 10 pages.
IL Application No. 238991, Office Action mailed Nov. 12, 2018; Applicant Magnolia Medical Technologies, Inc., with English Translation; 6 pages.
IL Application No. 273025, Office Action mailed Dec. 4, 2022; Applicant Magnolia Medical Technologies, Inc. et al., with English Translation; 6 pages.
IL Application No. 285289, Office Action mailed May 6, 2024; Applicant Magnolia Medical Technologies, Inc. et al.; 4 pages. (English Only).
IL Application No. 286263, Office Action mailed Aug. 5, 2025; Applicant Magnolia Medical Technologies, Inc. et al.; 3 pages. (English Only).
IL Application No. 286263, Office Action mailed May 12, 2024; Applicant Magnolia Medical Technologies, Inc. et al.; 4 pages. (English Only).
IL Application No. 303591, Office Action mailed Feb. 25, 2024; Applicant Magnolia Medical Technologies, Inc. et al.; 4 pages.
IL Application No. 309638, Office Action mailed Aug. 11, 2025; Applicant Magnolia Medical Technologies, Inc. et al.; 3 pages. (English Only).
IL Application No. 309638, Office Action mailed Jul. 16, 2024; Applicant Magnolia Medical Technologies, Inc. et al.; 3 pages. (English Only).
IL Application No. 313917, Office Action mailed May 29, 2025; Applicant Magnolia Medical Technologies, Inc. et al.; 4 pages. (English Only).
IN Application No. 11068/DELNP/2014, Office Action mailed Sep. 28, 2020; Applicant Magnolia Medical Technologies, Inc., with English Translation; 6 pages.
IN Application No. 202017008581, Office Action mailed Mar. 8, 2022; Applicant Magnolia Medical Technologies, Inc., with English Translation; 7 pages.
JP Application No. 2015-515178, Office Action mailed Feb. 16, 2017; Applicant Magnolia Medical Technologies, Inc. et al., with English Translation; 7 pages.
JP Application No. 2015-545494, Office Action mailed Jun. 19, 2017; Applicant Magnolia Medical Technologies, Inc., with English Translation; 9 pages.
JP Application No. 2015-545813, Office Action mailed Jul. 4, 2017; Applicant Magnolia Medical Technologies, Inc., with English Translation; 14 pages.
JP Application No. 2017-214629, Office Action mailed Jul. 23, 2019; Applicant Magnolia Medical Technologies, Inc., with English Translation; 8 pages.
JP Application No. 2017-214629, Office Action mailed Sep. 20, 2018; Applicant Magnolia Medical Technologies, Inc., with English Translation; 9 pages.
JP Application No. 2018-081980, Office Action mailed Feb. 21, 2019; Applicant Magnolia Medical Technologies, Inc., with English Translation; 9 pages.
JP Application No. 2018-081980, Office Action mailed Jan. 30, 2020; Applicant Magnolia Medical Technologies, Inc., with English Translation; 11 pages.
JP Application No. 2018-086721, Office Action mailed Mar. 15, 2019; Applicant Magnolia Medical Technologies, Inc., with English Translation; 6 pages.
JP Application No. 2019-230734, Office Action mailed Jan. 22, 2021; Applicant Magnolia Medical Technologies, Inc., with English Translation; 9 pages.
JP Application No. 2019-230734, Office Action mailed Jan. 5, 2022; Applicant Magnolia Medical Technologies, Inc., with English Translation; 6 pages.
JP Application No. 2020-075727, Office Action mailed Jul. 28, 2021; Applicant Magnolia Medical Technologies, Inc., with English Translation; 37 pages.
JP Application No. 2020-075727, Office Action mailed Mar. 28, 2023; Applicant Magnolia Medical Technologies, Inc., with English Translation; 6 pages.
JP Application No. 2020-075727, Office Action mailed May 18, 2022; Applicant Magnolia Medical Technologies, Inc., with English Translation; 11 pages.
JP Application No. 2020-094488, Office Action mailed Aug. 2, 2021; Applicant Magnolia Medical Technologies, Inc., with English Translation; 4 pages.
JP Application No. 2020-094488, Office Action mailed Mar. 31, 2022; Applicant Magnolia Medical Technologies, Inc., with English Translation; 6 pages.
JP Application No. 2020-511930, Office Action mailed Aug. 23, 2022; Applicant Magnolia Medical Technologies, Inc., with English Translation; 9 pages.
JP Application No. 2020-517772, Office Action mailed Dec. 26, 2022; Applicant Magnolia Medical Technologies, Inc., with English Translation; 6 pages.
JP Application No. 2020-517772, Office Action mailed Mar. 14, 2022; Applicant Magnolia Medical Technologies, Inc., with English Translation; 13 pages.
JP Application No. 2020-550048, Office Action mailed Aug. 5, 2022; Applicant Magnolia Medical Technologies, Inc., with English Translation; 5 pages.
JP Application No. 2020-566232, Office Action mailed Apr. 12, 2023; Applicant Magnolia Medical Technologies, Inc., with English Translation; 27 pages.
JP Application No. 2020-566232, Office Action mailed Sep. 19, 2023; Applicant Magnolia Medical Technologies, Inc., with English Translation; 6 pages.
JP Application No. 2021-546225, Office Action mailed Dec. 19, 2023; Applicant Magnolia Medical Technologies, Inc., with English Translation; 11 pages.
JP Application No. 2021-552145, Office Action mailed Sep. 11, 2024; Applicant Magnolia Medical Technologies, Inc., with English Translation; 4 pages.
JP Application No. 2022-074696, Office Action mailed Feb. 20, 2023; Applicant Magnolia Medical Technologies, Inc., with English Translation; 11 pages.
JP Application No. 2022-074696, Office Action mailed Oct. 25, 2023; Applicant Magnolia Medical Technologies, Inc., with English Translation; 7 pages.
JP Application No. 2022-184274, Office Action Appeal Decision No. 2024-016403 mailed Nov. 7, 2025, Applicant Magnolia Medical Technologies, Inc., with English translation; 73 pages.
JP Application No. 2022-184274, Office Action mailed Jun. 14, 2024; Applicant Magnolia Medical Technologies, Inc., with English Translation; 4 pages.
JP Application No. 2022-184274, Office Action mailed Oct. 27, 2023; Applicant Magnolia Medical Technologies, Inc., with English Translation; 6 pages.
JP Application No. 2022-212405, Office Action mailed Jun. 20, 2024; Applicant Magnolia Medical Technologies, Inc., with English Translation; 6 pages.
JP Application No. 2022-212405, Office Action mailed Nov. 29, 2023; Applicant Magnolia Medical Technologies, Inc., with English Translation; 13 pages.
JP Application No. 2022-534220, Office Action mailed Sep. 13, 2024; Applicant Magnolia Medical Technologies, Inc., with English Translation; 8 pages.

(56) References Cited

OTHER PUBLICATIONS

JP Application No. 2024-014849, Office Action mailed Apr. 30, 2025; Applicant Magnolia Medical Technologies, Inc., with English Translation; 9 pages.
JP Application No. 2024-014849, Office Action mailed Jan. 28, 2026; Applicant Magnolia Medical Technologies, Inc., with English Translation; 6 pages.
JP Application No. 2024-020482, Office Action mailed Mar. 11, 2025; Applicant Magnolia Medical Technologies, Inc., with English Translation; 16 pages.
JP Application No. 2024-115518, Office Action mailed Jun. 11, 2025; Applicant Magnolia Medical Technologies, Inc., with English Translation; 6 pages.
JP Application No. 2024-127830, Office Action mailed Nov. 4, 2025; Applicant Magnolia Medical Technologies, Inc., with English Translation; 8 pages.
JP Application No. 2024-153369, Office Action mailed Feb. 18, 2026; Applicant Magnolia Medical Technologies, Inc., with English Translation; 6 pages.
JP Application No. 2024-153369, Office Action mailed Sep. 5, 2025; Applicant Magnolia Medical Technologies, Inc., with English Translation; 10 pages.
JP Application No. 2024-187934, Office Action mailed Apr. 28, 2025; Applicant Magnolia Medical Technologies, Inc., with English Translation; 12 pages.
Marshall, L.A., et al.; "An injection molded microchip for nucleic acid purification from 25 microliter samples using isotachophoresis," J Chromatogr A.; 1331; pp. 139-142 (Feb. 2014).
McDonald, C.P.; "Bacterial risk reduction by improved donor arm disinfection, diversion and bacterial screening," Transfus Med., Dec. 2006, 16(6), pp. 381-396. doi: 10.1111/j.1365-3148.2006.00697.x.
Mohajer, M.A., et al.; "The Impact of Initial Specimen Diversion Systems on Blood Culture Contamination," Open Forum Infect Dis.; 10(5):ofad182; pp. 1-6. doi: 10.1093/ofid/ofad182 (Apr. 5, 2023).
Patel, R. et al., "Optimized Pathogen Detection with 30-Compared to 20-Milliliter Blood Culture Draws," Journal of Clinical Microbiology, Epub Oct. 5, 2011, 49(12):4047-4051 (Dec. 2011).
PCT Application No. PCT/US2007/087951, International Search Report and Written Opinion mailed May 16, 2008, Applicant Patton, Richard G.; 8 pages.
PCT Application No. PCT/US2013/043289, International Search Report and Written Opinion mailed Oct. 24, 2013, Applicant Magnolia Medical Technologies, Inc. et al.; 15 pages.
PCT Application No. PCT/US2013/052493, International Search Report and Written Opinion mailed Nov. 27, 2013, Applicant Magnolia Medical Technologies, Inc.; 7 pages.
PCT Application No. PCT/US2013/063975, International Search. Report and Written Opinion mailed Mar. 20, 2014, Applicant Magnolia Medical Technologies, Inc.; 16 pages.
PCT Application No. PCT/US2013/071491, International Search Report and Written Opinion mailed Aug. 5, 2014, Applicant Magnolia Medical Technologies, Inc.; 9 pages.
PCT Application No. PCT/US2013/072563, International Search Report and Written Opinion mailed Feb. 7, 2014, Applicant Magnolia Medical Technologies, Inc.; 11 pages.
PCT Application No. PCT/US2013/073080, International Search Report and Written Opinion mailed Feb. 18, 2014, Applicant Magnolia Medical Technologies, Inc.; 14 pages.
PCT Application No. PCT/US2016/037160, International Search Report and Written Opinion mailed Sep. 30, 2016, Applicant Magnolia Medical Technologies, Inc.; 10 pages.
PCT Application No. PCT/US2016/050380, International Search Report and Written Opinion mailed Dec. 1, 2016, Applicant Magnolia Medical Technologies, Inc.; 6 pages.
PCT Application No. PCT/US2018/036910, International Search Report and Written Opinion mailed Sep. 4, 2018, Applicant Magnolia Medical Technologies, Inc.; 13 pages.
PCT Application No. PCT/US2018/050621, International Search Report and Written Opinion mailed Nov. 26, 2018, Applicant Magnolia Medical Technologies, Inc.; 11 pages.
PCT Application No. PCT/US2018/064561, International Search Report and Written Opinion mailed Feb. 11, 2019, Applicant Magnolia Medical Technologies, Inc.; 9 pages.
PCT Application No. PCT/US2019/034626, International Search Report and Written Opinion mailed Aug. 22, 2019, Applicant Magnolia Medical Technologies, Inc.; 16 pages.
PCT Application No. PCT/US2020/017261, International Search Report and Written Opinion mailed May 14, 2020, Applicant Magnolia Medical Technologies, Inc.; 13 pages.
PCT Application No. PCT/US2020/022125, International Search Report and Written Opinion mailed May 26, 2020, Applicant Magnolia Medical Technologies, Inc.; 17 pages.
PCT Application No. PCT/US2020/064600, International Search Report and Written Opinion mailed Mar. 18, 2021, Applicant Magnolia Medical Technologies, Inc.; 14 pages.
Shen, H., et al.; "A microfluidic chip based sequential injection system with trapped droplet liquid-liquid extraction and chemiluminescence detection," Lab Chip; 6(10):1387-1389 (Oct. 2006).
Snyder, S.R., et al.; "Effectiveness of practices to reduce blood culture contamination: A Laboratory Medicine Best Practices systematic review and meta-analysis," Clin Biochem.; Epub Jun. 16, 2012; 45(Issues 13-14):999-1011. doi: 10.1016/j.clinbiochem.2012.06.007, 13 pages (Sep. 2012).
U.S. Appl. No. 11/955,635, Final Office Action mailed Dec. 3, 2010; Inventor Patton, Richard G.; 11 pages.
U.S. Appl. No. 11/955,635, Non-Final Office Action mailed Jul. 22, 2010; Inventor Patton, Richard G.; 11 pages.
U.S. Appl. No. 13/335,241, Non-Final Office Action mailed Apr. 20, 2012; Inventor Patton, Richard G.; 12 pages.
U.S. Appl. No. 13/458,508, Non-Final Office Action mailed Jul. 24, 2012; Inventor Patton, Richard G.; 13 pages.
U.S. Appl. No. 13/675,295, Non-Final Office Action mailed May 23, 2013; Inventor Patton, Richard G.; 15 pages.
U.S. Appl. No. 13/952,964, Non-Final Office Action mailed Mar. 20, 2015; Inventor Bullington, Gregory J. et al.; 11 pages.
U.S. Appl. No. 13/954,528, Non-Final Office Action mailed Mar. 17, 2014; Inventor Bullington, Gregory J. et al.; 10 pages.
U.S. Appl. No. 14/049,326, Non-Final Office Action mailed Apr. 24, 2015; Inventor Bullington, Gregory J. et al.; 10 pages.
U.S. Appl. No. 14/089,267, Non-Final Office Action mailed Jun. 19, 2014; Inventor Patton, Richard G.; 13 pages.
U.S. Appl. No. 14/096,826, Final Office Action mailed Mar. 8, 2018; Inventor Bullington, Gregory J. et al.; 14 pages.
U.S. Appl. No. 14/096,826, Non-Final Office Action mailed Jul. 26, 2017; Inventor Bullington, Gregory J. et al.; 12 pages.
U.S. Appl. No. 14/264,481, Final Office Action mailed Apr. 13, 2017; Inventor Bullington, Gregory J. et al.; 14 pages.
U.S. Appl. No. 14/264,481, Final Office Action mailed Jul. 14, 2016; Inventor Bullington, Gregory J. et al.; 9 pages.
U.S. Appl. No. 14/264,481, Non-Final Office Action mailed Feb. 26, 2016; Inventor Bullington, Gregory J. et al.; 10 pages.
U.S. Appl. No. 14/264,481, Non-Final Office Action mailed Jul. 1, 2015; Inventor Bullington, Gregory J. et al.; 13 pages.
U.S. Appl. No. 14/264,481, Non-Final Office Action mailed Oct. 21, 2016; Inventor Bullington, Gregory J. et al.; 10 pages.
U.S. Appl. No. 14/264,481, Non-Final Office Action mailed Sep. 7, 2017; Inventor Bullington, Gregory J. et al.; 12 pages.
U.S. Appl. No. 14/493,796, Non-Final Office Action mailed Jan. 27, 2015; Inventor Bullington, Gregory et al.; 7 pages.
U.S. Appl. No. 14/494,208, Non-Final Office Action mailed Jan. 27, 2015; Inventor Bullington, Gregory et al.; 7 pages.
U.S. Appl. No. 14/498,102, Final Office Action mailed Sep. 24, 2018; Inventor Patton, Richard G.; 18 pages.
U.S. Appl. No. 14/498,102, Non-Final Office Action mailed Oct. 17, 2017; Inventor Patton, Richard G.; 20 pages.
U.S. Appl. No. 14/662,676, Non-Final Office Action mailed Sep. 5, 2018; Inventor Bullington, Gregory et al.; 25 pages.
U.S. Appl. No. 14/712,431, Non-Final Office Action mailed Sep. 14, 2018; Inventor Bullington, Gregory et al.; 10 pages.

(56) References Cited

OTHER PUBLICATIONS

U.S. Appl. No. 14/712,437, Non-Final Office Action mailed Oct. 25, 2018; Inventor Bullington, Gregory J. et al.; 20 pages.
U.S. Appl. No. 14/728,318, Final Office Action mailed Dec. 20, 2018; Inventor Bullington, Gregory J. et al.; 26 pages.
U.S. Appl. No. 14/728,318, Final Office Action mailed Jan. 8, 2018; Inventor Bullington, Gregory J. et al.; 36 pages.
U.S. Appl. No. 14/728,318, Final Office Action mailed Jul. 18, 2019; Inventor Bullington, Gregory J. et al.; 27 pages.
U.S. Appl. No. 14/728,318, Non-Final Office Action mailed May 19, 2017; Inventor Bullington, Gregory J. et al.; 26 pages.
U.S. Appl. No. 14/838,794, Non-Final Office Action mailed Aug. 3, 2017; Inventor Bullington, Gregory J. et al.; 8 pages.
U.S. Appl. No. 14/880,397, Final Office Action mailed Sep. 24, 2018; Inventor Bullington, Gregory J. et al.; 5 pages.
U.S. Appl. No. 14/880,397, Non-Final Office Action mailed Apr. 17, 2018; Inventor Bullington, Gregory J. et al.; 6 pages.
U.S. Appl. No. 14/926,784, Final Office Action mailed Jan. 15, 2019; Inventor Bullington, Gregory J. et al.; 15 pages.
U.S. Appl. No. 14/926,784, Non-Final Office Action mailed Jan. 21, 2020; Inventor Bullington, Gregory J. et al.; 17 pages.
U.S. Appl. No. 14/926,784, Non-Final Office Action mailed May 25, 2018; Inventor Bullington, Gregory J. et al.; 17 pages.
U.S. Appl. No. 15/088,842, Non-Final Office Action mailed Nov. 23, 2016; Inventor Patton, Richard G.; 20 pages.
U.S. Appl. No. 15/180,454, Final Office Action mailed Apr. 1, 2020; Inventor Bullington, Gregory J. et al.; 28 pages.
U.S. Appl. No. 15/180,454, Non-Final Office Action mailed Jan. 21, 2021; Inventor Bullington, Gregory J. et al.; 24 pages.
U.S. Appl. No. 15/180,454, Non-Final Office Action mailed Jul. 25, 2019; Inventor Bullington, Gregory J. et al.; 27 pages.
U.S. Appl. No. 15/257,185, Non-Final Office Action mailed Aug. 8, 2017; Inventor Bullington, Gregory J. et al.; 5 pages.
U.S. Appl. No. 15/432,310, Non-Final Office Action mailed Apr. 12, 2017; Inventor Patton, Richard G.; 14 pages.
U.S. Appl. No. 15/435,684, Non-Final Office Action mailed Jun. 12, 2017; Inventor Patton, Richard G.; 19 pages.
U.S. Appl. No. 15/448,891, Non-Final Office Action mailed Jun. 16, 2017; Inventor Patton, Richard G.; 25 pages.
U.S. Appl. No. 15/457,082, Non-Final Office Action mailed Jun. 15, 2017; Inventor Patton, Richard G.; 22 pages.
U.S. Appl. No. 15/829,015, Non-Final Office Action mailed Feb. 6, 2018; Inventor Patton, Richard G.; 24 pages.
U.S. Appl. No. 15/829,018, Non-Final Office Action mailed Feb. 16, 2018; Inventor Patton, Richard G.; 13 pages.
U.S. Appl. No. 15/829,023, Non-Final Office Action mailed Feb. 7, 2018; Inventor Patton, Richard G.; 25 pages.
U.S. Appl. No. 15/832,055, Non-Final Office Action mailed Feb. 8, 2018; Inventor Patton, Richard G.; 21 pages.
U.S. Appl. No. 15/832,087, Non-Final Office Action mailed Feb. 7, 2018; Inventor Patton, Richard G.; 24 pages.
U.S. Appl. No. 15/832,091, Non-Final Office Action mailed Feb. 22, 2018; Inventor Bullington, Gregory J. et al.; 16 pages.
U.S. Appl. No. 15/854,273, Final Office Action mailed Mar. 15, 2019; Inventor Bullington, Gregory J. et al.; 19 pages.
U.S. Appl. No. 15/854,273, Non-Final Office Action mailed Jan. 13, 2020; Inventor Bullington, Gregory J. et al.; 13 pages.
U.S. Appl. No. 15/854,273, Non-Final Office Action mailed Sep. 7, 2018; Inventor Bullington, Gregory J. et al.; 15 pages.
U.S. Appl. No. 15/925,159, Final Office Action mailed May 14, 2019; Inventor Bullington, Gregory J. et al.; 13 pages.
U.S. Appl. No. 15/925,159, Non-Final Office Action mailed Nov. 26, 2018; Inventor Bullington, Gregory J. et al.; 11 pages.
U.S. Appl. No. 16/004,955, Non-Final Office Action mailed Feb. 16, 2021; Inventor Bullington, Gregory J. et al.; 28 pages.
U.S. Appl. No. 16/129,066, Non-Final Office Action mailed Sep. 3, 2020; Inventor Bullington, Gregory J. et al.; 13 pages.
U.S. Appl. No. 16/213,005, Non-Final Office Action mailed Feb. 3, 2021; Inventor Bullington, Gregory J. et al.; 15 pages.
U.S. Appl. No. 16/255,055, Non-Final Office Action mailed Mar. 18, 2019; Inventor Bullington, Gregory J. et al.; 16 pages.
U.S. Appl. No. 16/255,058, Non-Final Office Action mailed Mar. 30, 2021; Inventor Bullington, Gregory J. et al.; 16 pages.
U.S. Appl. No. 16/274,835, Non-Final Office Action mailed Feb. 12, 2021; Inventor Bullington, Gregory J. et al.; 17 pages.
U.S. Appl. No. 16/299,962, Final Office Action mailed Dec. 26, 2019; Inventor Bullington, Gregory J. et al.; 14 pages.
U.S. Appl. No. 16/299,962, Final Office Action mailed Jun. 15, 2021; Inventor Bullington, Gregory J. et al.; 17 pages.
U.S. Appl. No. 16/299,962, Non-Final Office Action mailed Dec. 9, 2020; Inventor Bullington, Gregory J. et al.; 15 pages.
U.S. Appl. No. 16/299,962, Non-Final Office Action mailed May 2, 2019; Inventor Bullington, Gregory J. et al.; 14 pages.
U.S. Appl. No. 16/376,745, Non-Final Office Action mailed May 14, 2021; Inventor Bullington, Gregory J. et al.; 13 pages.
U.S. Appl. No. 16/379,128, Non-Final Office Action mailed Apr. 26, 2022; Inventor Patton, Richard G.; 14 pages.
U.S. Appl. No. 16/426,380, Final Office Action mailed May 7, 2021; Inventor Bullington, Gregory J. et al.; 28 pages.
U.S. Appl. No. 16/426,380, Non-Final Office Action mailed Oct. 30, 2020; Inventor Bullington, Gregory J. et al.; 29 pages.
U.S. Appl. No. 16/785,170, Non-Final Office Action mailed Sep. 14, 2022; Inventor Bullington, Gregory J. et al.; 11 pages.
U.S. Appl. No. 16/789,034, Non-Final Office Action mailed Feb. 9, 2023; Inventor Bullington, Gregory J. et al.; 11 pages.
U.S. Appl. No. 16/815,521, Non-Final Office Action mailed Oct. 25, 2023; Inventor Bullington, Gregory J. et al.; 9 pages.
U.S. Appl. No. 16/934,975, Non-Final Office Action mailed Oct. 6, 2022; Inventor Bullington, Gregory J. et al.; 18 pages.
U.S. Appl. No. 17/119,732, Non-Final Office Action mailed Aug. 25, 2022; Inventor Bullington, Gregory J. et al.; 30 pages.
U.S. Appl. No. 17/136,882, Final Office Action mailed Dec. 31, 2024; Inventor Bullington, Gregory J. et al.; 6 pages.
U.S. Appl. No. 17/136,882, Final Office Action mailed Nov. 8, 2023; Inventor Bullington, Gregory J. et al.; 11 pages.
U.S. Appl. No. 17/136,882, Non-Final Office Action mailed Apr. 19, 2024; Inventor Bullington, Gregory J. et al.; 8 pages.
U.S. Appl. No. 17/136,882, Non-Final Office Action mailed Jun. 9, 2023; Inventor Bullington, Gregory J. et al.; 11 pages.
U.S. Appl. No. 17/138,056, Non-Final Office Action mailed Dec. 21, 2022; Inventor Bullington, Gregory J. et al.; 11 pages.
U.S. Appl. No. 17/388,971, Non-Final Office Action mailed Nov. 23, 2021; Inventor Bullington, Gregory J. et al.; 19 pages.
U.S. Appl. No. 17/388,979, Non-Final Office Action mailed Dec. 8, 2021; Inventor Bullington, Gregory J. et al.; 21 pages.
U.S. Appl. No. 17/390,249, Non-Final Office Action mailed Nov. 8, 2023; Inventor Bullington, Gregory J. et al.; 9 pages.
U.S. Appl. No. 17/403,500, Final Office Action mailed Jul. 28, 2023; Inventor Bullington, Gregory J. et al.; 18 pages.
U.S. Appl. No. 17/403,500, Final Office Action mailed Nov. 13, 2024; Inventor Bullington, Gregory J. et al.; 27 pages.
U.S. Appl. No. 17/403,500, Non-Final Office Action mailed May 20, 2024; Inventor Bullington, Gregory J. et al.; 28 pages.
U.S. Appl. No. 17/403,500, Non-Final Office Action mailed Sep. 27, 2022; Inventor Bullington, Gregory J. et al.; 29 pages.
U.S. Appl. No. 17/516,887, Final Office Action mailed Aug. 13, 2025; Inventor Bullington, Gregory J. et al.; 24 pages.
U.S. Appl. No. 17/516,887, Non-Final Office Action mailed Jan. 13, 2025; Inventor Bullington, Gregory J. et al.; 42 pages.
U.S. Appl. No. 17/525,682, Non-Final Office Action mailed Feb. 7, 2022; Inventor Bullington, Gregory J. et al.; 12 pages.
U.S. Appl. No. 17/532,382, Non-Final Office Action mailed Feb. 7, 2022; Inventor Bullington, Gregory J. et al.; 10 pages.
U.S. Appl. No. 17/559,081, Non-Final Office Action mailed Jan. 12, 2026; Inventor Bullington, Gregory J. et al.; 10 pages.
U.S. Appl. No. 17/583,791, Non-Final Office Action mailed Dec. 23, 2024; Inventor Bullington, Gregory J. et al.; 19 pages.
U.S. Appl. No. 17/591,237, Final Office Action mailed Aug. 20, 2025; Inventor Bullington, Gregory J. et al.; 24 pages.
U.S. Appl. No. 17/591,237, Final Office Action mailed Aug. 25, 2023; Inventor Bullington, Gregory J. et al.; 25 pages.

(56) References Cited

OTHER PUBLICATIONS

U.S. Appl. No. 17/591,237, Final Office Action mailed Aug. 4, 2022; Inventor Bullington, Gregory J. et al.; 26 pages.
U.S. Appl. No. 17/591,237, Non-Final Office Action mailed Feb. 16, 2023; Inventor Bullington, Gregory J. et al.; 34 pages.
U.S. Appl. No. 17/591,237, Non-Final Office Action mailed Jan. 24, 2025; Inventor Bullington, Gregory J. et al.; 34 pages.
U.S. Appl. No. 17/591,237, Non-Final Office Action mailed May 3, 2022; Inventor Bullington, Gregory J. et al.; 20 pages.
U.S. Appl. No. 17/591,239, Final Office Action mailed Aug. 23, 2023; Inventor Bullington, Gregory J. et al.; 23 pages.
U.S. Appl. No. 17/591,239, Final Office Action mailed Aug. 4, 2022; Inventor Bullington, Gregory J. et al.; 26 pages.
U.S. Appl. No. 17/591,239, Non-Final Office Action mailed Feb. 17, 2023; Inventor Bullington, Gregory J. et al.; 34 pages.
U.S. Appl. No. 17/591,239, Non-Final Office Action mailed Jan. 24, 2025; Inventor Bullington, Gregory J. et al.; 32 pages.
U.S. Appl. No. 17/591,239, Non-Final Office Action mailed May 3, 2022; Inventor Bullington, Gregory J. et al.; 21 pages.
U.S. Appl. No. 17/684,920, Final Office Action mailed Jan. 31, 2023; Inventor Bullington, Gregory J. et al.; 9.pages.
U.S. Appl. No. 17/684,920, Non-Final Office Action mailed Jul. 11, 2022; Inventor Bullington, Gregory J. et al.; 12 pages.
U.S. Appl. No. 17/710,389, Non-Final Office Action mailed Jun. 16, 2022; Inventor Bullington, Gregory J. et al.; 25 pages.
U.S. Appl. No. 17/710,401, Non-Final Office Action mailed Jul. 6, 2022; Inventor Bullington, Gregory J. et al.; 22 pages.
U.S. Appl. No. 17/710,411, Non-Final Office Action mailed Jul. 6, 2022; Inventor Bullington, Gregory J. et al.; 22 pages.
U.S. Appl. No. 17/863,605, Non-Final Office Action mailed Nov. 28, 2023; Inventor Bullington, Gregory J. et al.; 15 pages.
U.S. Appl. No. 17/869,256, Non-Final Office Action mailed May 5, 2025; Inventor Bullington, Gregory J. et al.; 24 pages.
U.S. Appl. No. 18/130,207, Non-Final Office Action mailed Aug. 21, 2023; Inventor Bullington, Gregory J. et al.; 7 pages.
U.S. Appl. No. 18/209,327, Non-Final Office Action mailed Dec. 16, 2025; Inventor Patton, Richard G.; 19 pages.
U.S. Appl. No. 18/227,185, Final Office Action mailed Oct. 31, 2024; Inventor Bullington, Gregory J. et al.; 17 pages.
U.S. Appl. No. 18/240,178, Non-Final Office Action mailed Feb. 27, 2025; Inventor Bullington, Gregory J. et al.; 12 pages.
U.S. Appl. No. 18/240,178, Non-Final Office Action mailed Jun. 12, 2024; Inventor Bullington, Gregory J. et al.; 16 pages.
U.S. Appl. No. 18/243,540, Non-Final Office Action mailed Jun. 4, 2025; Inventor Bullington, Gregory J. et al.; 34 pages.
U.S. Appl. No. 18/299,680, Non-Final Office Action mailed Aug. 15, 2023; Inventor Bullington, Gregory J. et al.; 5 pages.
U.S. Appl. No. 18/380,259, Non-Final Office Action mailed Jan. 29, 2024; Inventor Bullington, Gregory J. et al.; 33 pages.
U.S. Appl. No. 18/380,259, Non-Final Office Action mailed Oct. 16, 2024; Inventor Bullington, Gregory J. et al.; 15 pages.
U.S. Appl. No. 18/381,369, Non-Final Office Action mailed Nov. 28, 2023; Inventor Bullington, Gregory J. et al.; 16 pages.
U.S. Appl. No. 18/407,010, Final Office Action mailed Sep. 6, 2024; Inventor Bullington, Gregory J. et al.; 11 pages.
U.S. Appl. No. 18/407,010, Non-Final Office Action mailed Dec. 4, 2025; Inventor Bullington, Gregory J. et al.; 7 pages.
U.S. Appl. No. 18/675,824, Non-Final Office Action mailed Jul. 26, 2024; Inventor Bullington, Gregory J. et al.; 13 pages.
U.S. Appl. No. 18/676,186, Non-Final Office Action mailed Aug. 5, 2024; Inventor Bullington, Gregory J. et al.; 13 pages.
U.S. Appl. No. 18/680,331, Final Office Action mailed Nov. 24, 2025; Inventor Bullington, Gregory J. et al.; 9 pages.
U.S. Appl. No. 18/680,331, Non-Final Office Action mailed Mar. 25, 2025; Inventor Bullington, Gregory J. et al.; 8 pages.
U.S. Appl. No. 18/680,348, Final Office Action mailed Nov. 24, 2025; Inventor Bullington; Gregory J. et al.; 8 pages.
U.S. Appl. No. 18/680,348, Non-Final Office Action mailed Mar. 25, 2025; Inventor Bullington, Gregory J. et al.; 7 pages.
U.S. Appl. No. 18/680,377, Final Office Action mailed Nov. 25, 2025; Inventor Bullington, Gregory J., et al.; 14 pages.
U.S. Appl. No. 18/680,377, Non-Final Office Action mailed Mar. 26, 2025; Inventor Bullington, Gregory J. et al.; 12 pages.
U.S. Appl. No. 18/680,439, Final Office Action mailed Nov. 25, 2025; Inventor Bullington, Gregory J., et al.; 10 pages.
U.S. Appl. No. 18/680,439, Non-Final Office Action mailed Mar. 31, 2025; Inventor Bullington, Gregory J. et al.; 8 pages.
U.S. Appl. No. 18/680,466, Final Office Action mailed Aug. 20, 2025; Inventor Bullington, Gregory J. et al.; 10 pages.
U.S. Appl. No. 18/680,466, Non-Final Office Action mailed Dec. 30, 2024; Inventor Bullington, Gregory J. et al.; 7 pages.
U.S. Appl. No. 18/960,441, Non-Final Office Action mailed Jan. 17, 2025; Inventor Bullington, Gregory J. et al.; 8 pages.
U.S. Appl. No. 18/990,547, Non-Final Office Action mailed Jan. 31, 2025; Inventor Bullington, Gregory J. et al.; 10 pages.
U.S. Appl. No. 19/175,765, Final Office Action mailed Nov. 26, 2025; Inventor Bullington, Gregory J. et al.; 14 pages.
U.S. Appl. No. 19/175,765, Non-Final Office Action mailed Aug. 8, 2025; Inventor Bullington, Gregory J. et al.; 11 pages.
U.S. Appl. No. 19/353,350, Non-Final Office Action mailed Feb. 9, 2026; Inventor Bullington, Gregory et al.; 23 pages.
U.S. Appl. No. 90/015,399, Order Granting Request for Ex Parte Reexamination mailed Oct. 21, 2025; Inventor Bullington, Gregory J., et al.; 43 pages.
U.S. Appl. No. 90/015,399, Request for Ex Parte Reexamination of U.S. Pat. No. 10,039,483 Under 35 U.S.C. § 302 and 37 C.F.R. § 1.510 filed Jul. 21, 2025, Inventor Bullington, Gregory J., et al.; 66 pages.
U.S. Appl. No. 90/019,177, Declaration of Dr. Erik K. Antonsson (Ph.D., P.E., NAE) in Ex Parte Reexamination dated Mar. 21, 2023; 137 pages.
U.S. Appl. No. 90/019,177, Final Office Action in Ex Parte Reexamination mailed Dec. 1, 2023; Inventor Bullington, Gregory J. et al.; 19 pages.
U.S. Appl. No. 90/019,177, Order Granting Request for Ex Parte Reexamination mailed Apr. 26, 2023, Inventor Bullington, Gregory J., et al.; 16 pages.
U.S. Appl. No. 90/019,177, Patent Trial and Appeal Board Decision in Ex Parte Reexamination mailed May 20, 2025, Inventor Bullington, Gregory J., et al.; 22 pages.
U.S. Appl. No. 90/019,177, Request for Ex Parte Reexamination of U.S. Pat. No. 10,039,483 Under 35 U.S.C. § 302 and 37 C.F.R. § 1.510 filed Mar. 22, 2023; Inventor Bullington, Gregory J., et al.; 84 pages.
U.S. Appl. No. 90/019,177, "Vent" Definition & Meaning—Merriam-Webster (https://www.merriam-webster.com/dictionary/vent, accessed Mar. 21, 2023); 16 pages.
U.S. Appl. No. 90/019,177, "Vent," n.2: Oxford English Dictionary (https://www.oed.com/view/Entry/222207?&print, accessed Feb. 16, 2023); 12 pages.
U.S. Appl. No. 90/019,756, Declaration of Dr. Erik K. Antonsson (Ph.D., P.E., NAE) in Ex Parte Reexamination dated Dec. 5, 2024; 138 pages.
U.S. Appl. No. 90/019,756, Declaration of Dr. Morten Jensen (Ph.D., Dr.Med., FAHA) under 37 C.F.R. § 1.132 in Ex Parte Reexamination dated Feb. 10, 2026; 74 pages.
U.S. Appl. No. 90/019,756, Declaration of Dr. Morten Jensen (Ph.D., Dr.Med., FAHA) under 37 C.F.R. § 1.132 in Ex Parte Reexamination dated Oct. 1, 2025; 79 pages.
U.S. Appl. No. 90/019,756, Examiner Interview Summary in Ex Parte Reexamination mailed Feb. 18, 2026, Inventor Patton, Richard G.; 4 pages.
U.S. Appl. No. 90/019,756, Examiner Interview Summary in Ex Parte Reexamination mailed Sep. 17, 2025, Inventor Patton, Richard G.; 7 pages.
U.S. Appl. No. 90/019,756, Non-Final Office Action in Ex Parte Reexamination mailed Jun. 17, 2025; Inventor Patton, Richard G.; et al.; 38 pages.
U.S. Appl. No. 90/019,756, Non-Final Office Action in Ex Parte Reexamination mailed Nov. 10, 2025; Inventor Patton, Richard G.; 44 pages.

(56) References Cited

OTHER PUBLICATIONS

U.S. Appl. No. 90/019,756, Office Action Appendix in Ex Parte Reexamination dated Feb. 18, 2026, Inventor Patton, Richard G.; 28 pages.
U.S. Appl. No. 90/019,756, Order Granting Request for Ex Parte Reexamination mailed Jan. 22, 2025, Inventor Patton, Richard G.; 14 pages.
U.S. Appl. No. 90/019,756, Request for Ex Parte Reexamination of U.S. Pat. No. 10,052,053 Under 35 U.S.C. § 302 and 37 C.F.R. § 1.510 filed Dec. 6, 2024, Inventor Patton, Richard G.; 144 pages.
U.S. Appl. No. 90/019,757, Declaration of Dr. Erik K. Antonsson (Ph.D., P.E., NAE) in Ex Parte Reexamination dated Dec. 5, 2024; 141 pages.
U.S. Appl. No. 90/019,757, Declaration of Dr. Morten Jensen (Ph.D., Dr.Med., FAHA) under 37 C.F.R. § 1.132 in Ex Parte Reexamination dated Mar. 2, 2026; 61 pages.
U.S. Appl. No. 90/019,757, Declaration of Dr. Morten Jensen (Ph.D., Dr.Med., FAHA) under 37 C.F.R. § 1.132 in Ex Parte Reexamination dated Oct. 1, 2025; 61 pages.
U.S. Appl. No. 90/019,757, Examiner Interview Summary in Ex Parte Reexamination mailed Sep. 17, 2025, Inventor Patton, Richard G.; 7 pages.
U.S. Appl. No. 90/019,757, Final Office Action in Ex Parte Reexamination mailed Nov. 28, 2025, Inventor Patton, Richard G.; 46 pages.
U.S. Appl. No. 90/019,757, Non-Final Office Action in Ex Parte Reexamination mailed Jun. 17, 2025, Inventor Patton, Richard G.; 27 pages.
U.S. Appl. No. 90/019,757, Order Granting Request for Ex Parte Reexamination mailed Jan. 27, 2025, Inventor Patton, Richard G.; 15 pages.
U.S. Appl. No. 90/019,757, Request for Ex Parte Reexamination of U.S. Pat. No. 9,855,002 Under 35 U.S.C. § 302 and 37 C.F.R. § 1.510 filed Dec. 6, 2024, Inventor Patton, Richard G.; 147 pages.
U.S. Appl. No. 90/019,757, Response to Final Office Action in Ex Parte Reexamination Mar. 2, 2026; Inventor Bullington, Gregory J.; 154 pages.
U.S. Appl. No. 90/019,823, Declaration of Dr. Erik K. Antonsson (Ph.D., P.E., NAE) in Ex Parte Reexamination dated Jan. 20, 2025; 164 pages.
U.S. Appl. No. 90/019,823, Declaration of Dr. Morten Jensen (Ph.D., Dr.Med., FAHA) under 37 C.F.R. § 1.132 in Ex Parte Reexamination dated Nov. 25, 2025; 75 pages.
U.S. Appl. No. 90/019,823, Final Office Action in Ex Parte Reexamination mailed Mar. 2, 2026; Inventor Bullington, Gregory J. et al.; 16 pages.
U.S. Appl. No. 90/019,823, Examiner Interview Summary in Ex Parte Reexamination mailed Nov. 25, 2025, Inventor Bullington, Gregory J.; 31 pages.
U.S. Appl. No. 90/019,823, Non-Final Office Action in Ex Parte Reexamination mailed Aug. 25, 2025, Inventor Bullington, Gregory J. et al.; 30 pages.
U.S. Appl. No. 90/019,823, Order Granting Request for Ex Parte Reexamination mailed Feb. 24, 2025, Inventor Bullington, Gregory J. et al.; 16 pages.
U.S. Appl. No. 90/019,823, Request for Ex Parte Reexamination of U.S. Pat. No. 11,529,081 Under 35 U.S.C. § 302 and 37 C.F.R. § 1.510 filed Jan. 21, 2025, Inventor Bullington, Gregory J., et al.; 179 pages.
U.S. Appl. No. 90/019,823, Response to Non-Final Office Action in Ex Parte Reexamination filed Nov. 25, 2025; Inventor Bullington, Gregory J.; 211 pages.
U.S. Appl. No. 90/019,824, Declaration of Dr. Erik K. Antonsson (Ph.D., P.E., NAE) in Ex Parte Reexamination dated Jan. 20, 2025; 161 pages.
U.S. Appl. No. 90/019,824, Declaration of Dr. Morten Jensen (Ph.D., Dr.Med., FAHA) under 37 C.F.R. § 1.132 in Ex Parte Reexamination dated Feb. 3, 2026; 80 pages.
U.S. Appl. No. 90/019,824, Examiner Interview Summary in Ex Parte Reexamination mailed Jan. 29, 2026; Inventor Bullington, Gregory J., et al.; 3 pages.
U.S. Appl. No. 90/019,824, Final Office Action in Ex Parte Reexamination mailed Mar. 18, 2026; Inventor Bullington, Gregory J., et al.; 14 pages.
U.S. Appl. No. 90/019,824, Non-Final Office Action in Ex Parte Reexamination mailed Nov. 4, 2025; Inventor Bullington, Gregory J., et al.; 22 pages.
U.S. Appl. No. 90/019,824, Order Granting Request for Ex Parte Reexamination mailed Feb. 24, 2025, Inventor Bullington, Gregory J., et al.; 18 pages.
U.S. Appl. No. 90/019,824, Request for Ex Parte Reexamination of U.S. Pat. No. 11,903,709 Under 35 U.S.C. § 302 and 37 C.F.R. § 1.510 filed Jan. 21, 2025, Inventor Bullington, Gregory J., et al.; 176 pages.
U.S. Appl. No. 90/019,825, Declaration of Dr. Erik K. Antonsson (Ph.D., P.E., NAE) in Ex Parte Reexamination dated Jan. 20, 2025; 169 pages.
U.S. Appl. No. 90/019,825, Declaration of Dr. Morten Jensen (Ph.D., Dr.Med., FAHA) under 37 C.F.R. § 1.132 in Ex Parte Reexamination dated Feb. 16, 2026; 84 pages.
U.S. Appl. No. 90/019,825, Examiner Interview Summary in Ex Parte Reexamination mailed Jan. 29, 2026, Inventor Bullington, Gregory J. et al.; 3 pages.
U.S. Appl. No. 90/019,825, Final Office Action in Ex Parte Reexamination mailed Mar. 19, 2026, Inventor Bullington, Gregory J., et al.; 13 pages.
U.S. Appl. No. 90/019,825, Non-Final Office Action in Ex Parte Reexamination mailed Nov. 17, 2025, Inventor Bullington, Gregory J., et al.; 25 pages.
U.S. Appl. No. 90/019,825, Order Granting Request for Ex Parte Reexamination mailed Feb. 25, 2025, Inventor Bullington, Gregory J., et al.; 15 pages.
U.S. Appl. No. 90/019,825, Request for Ex Parte Reexamination of U11653863 Under 35 U.S.C. § 302 and 37 C.F.R. § 1.510 filed Jan. 21, 2025, Inventor Bullington, Gregory J., et al.; 180 pages.
Valleywise Health Medical Center Case Study "In anticipation of CMS changes, AZ hospital identifies solution to blood culture contaminations with new Kurin Jet™," Brochure; 1 page (Publication Date Unknown).
Widmer, A.F., et al.; "Sterilization of skin and catheters before drawing blood cultures," J Clin Microbiol.; 41(10):4910; 1 page (Oct. 2003).
Wilber, E.P., et al.; "Effect of an initial specimen diversion device on blood-culture contamination rates and vancomycin usage: A quasi-experimental study," Epub Aug. 3, 2023; Infect Control Hosp Epidemiol.; 45(1):100-102 (Jan. 2024).
Zwang, O., et al.; "Analysis of strategies to improve cost effectiveness of blood cultures," J Hosp Med.; 1(5):272-276. doi: 10.1002/jhm.115 (Sep. 2006).
CA Application No. 3129065, Office Action mailed Apr. 13, 2026; Applicant Magnolia Medical Technologies, Inc.; 3 total pages.
JP Application No. 2024-127830, Office Action mailed Apr. 22, 2026; Applicant Magnolia Medical Technologies, Inc., with English Translation; 6 pages.
U.S. Appl. No. 17/591,239, Final Office Action mailed Apr. 30, 2026; Inventor Bullington, Gregory J. et al.; 24 pages.
U.S. Appl. No. 90/019,757, Reexamination Certificate issued May 14, 2026, Inventor: Patton, 8 pages.
U.S. Appl. No. 90/019,823, Examiner Interview Summary in Ex Parte Reexamination mailed Apr. 28, 2026, Inventor Bullington, Gregory J.; 3 pages.
U.S. Appl. No. 90/019,823, Response to Office Action in Ex Parte Reexamination dated May 1, 2026, Inventor Bullington, Gregory J.; 185 pages.
U.S. Appl. No. 90/019,824, Examiner Interview Summary mailed Apr. 28, 2026; Inventor Bullington, Gregory J., et al.; 3 pages.
U.S. Appl. No. 90/019,825, Examiner Interview Summary mailed Apr. 28, 2026, Inventor Bullington, Gregory J., et al.; 3 pages.

FLUID CONTROL DEVICES AND METHODS OF USING THE SAME

CROSS-REFERENCE TO RELATED APPLICATIONS

This application is a continuation of U.S. patent application Ser. No. 16/815,526 entitled "Fluid Control Devices and Methods of Using the Same," filed Mar. 11, 2020, which claims priority to and the benefit of U.S. Provisional Patent Application Ser. No. 62/816,477 entitled, "Fluid Control Devices and Methods of Using the Same," filed Mar. 11, 2019, the disclosures of each of which is incorporated herein by reference in its entirety.

BACKGROUND

Embodiments described herein relate generally to the procurement of bodily fluid samples, and more particularly to fluid diversion, sequestration, and/or isolation devices and methods for procuring bodily fluid samples with reduced contaminants such as dermally residing microbes and/or other contaminants exterior to the bodily fluid source.

Health care practitioners routinely perform various types of microbial as well as other broad diagnostic tests on patients using parenterally obtained bodily fluids. As advanced diagnostic technologies evolve and improve, the speed, accuracy (both sensitivity and specificity), and value of information that can be provided to clinicians continues to improve. Maintaining the integrity of the bodily fluid sample during and/or after collection ensures that analytical diagnostic results are representative of the in vivo conditions of a patient. Examples of diagnostic technologies that are reliant on high quality, non-contaminated, and/or unadulterated bodily fluid samples include but are not limited to microbial detection, molecular diagnostics, genetic sequencing (e.g., deoxyribonucleic acid (DNA), ribonucleic acid (RNA), next-generation sequencing (NGS), etc.), biomarker identification, and the like.

Inaccurate results from such testing, can result from the presence of biological matter—including cells external to the intended sample source and/or other external contaminants—that inadvertently are included in the bodily fluid sample being analyzed. In short, when the purity of the bodily fluid sample is compromised during the specimen procurement process, resultant analytical test results may be inaccurate, distorted, adulterated, falsely positive, falsely negative, and/or otherwise not representative of the actual condition of the patient. In turn, these results can lead to faulty, inaccurate, confused, unsure, low confidence, and/or otherwise undesired clinical decision-making.

In some instances, devices and/or systems can be used to reduce the likelihood of contamination, adulteration, and/or the like of bodily fluid samples for testing. For example, some known devices can be configured to collect, divert, separate, and/or sequester (e.g., isolate) an initial volume of bodily fluid that may be more likely to contain contaminants such as dermally residing microbes or the like. Some such devices, however, can be cumbersome, non-intuitive, perceived as difficult to use, inappropriate or unusable for a target patient population, etc. In addition, some such devices can require training, user observation, intervention by more than one user, and/or can otherwise present challenges that can lead to limited efficacy. In some instances, these and/or other challenges can complicate the collection of consistently high quality samples that are non-contaminated, sterile, unadulterated, etc., which in turn, can influence the validity of test result outcomes.

Some known devices and/or systems may be configured to limit an amount of user intervention by passively diverting an initial volume of bodily fluid, however, some such devices and/or systems may fail to adequately divert, sequester, and/or isolate a clinically desired and/or efficacious initial volume of bodily fluid (e.g., a pre-sample volume). Moreover, in some instances, the operation of some known devices and/or systems is dependent on a positive pressure applied or supplied by a bodily fluid source (e.g., a patient's blood pressure). In some such instances, however, the positive pressure may be insufficient to result in desirable flow dynamics and/or flow rates that make the use of such devices practical in various clinical settings such as, for example, emergency rooms and other intensive settings.

As such, a need exists for fluid control and/or diversion devices and methods for procuring bodily fluid samples with reduced contaminants such as dermally residing microbes and/or other contaminants exterior to the bodily fluid source that result in consistent bodily fluid collection (e.g., from a general patient population and/or a challenging patient population). In addition, a need exists for devices and methods that include, for example, bodily fluid collection with the assistance of various sources of external energy and/or negative pressure.

SUMMARY

Devices and methods for procuring bodily fluid samples with reduced contaminants such as dermally residing microbes and/or other contaminants exterior to the bodily fluid source are described herein. In some embodiments an apparatus for procuring bodily fluid samples with reduced contamination includes a housing, an actuator, and a flow controller. The housing forms at least a portion of a sequestration chamber, and has an inlet configured to be fluidically coupled to a bodily fluid source, and an outlet configured to be fluidically coupled to a fluid collection device. The fluid collection device exerts a suction force in at least a portion of the housing when fluidically coupled to the outlet. The actuator is coupled to the housing and has a first configuration in which the inlet is in fluid communication with the sequestration chamber, and a second configuration in which the inlet is in fluid communication with the outlet and is fluidically isolated from the sequestration chamber. The flow controller is disposed in the housing and defines a portion of the sequestration chamber. The flow controller can assume a first state in which the portion of the sequestration chamber has a first volume, and a second state in which the portion of the sequestration chamber has a second volume greater than the first volume. When the actuator is in the first configuration, the flow controller is configured to transition from the first state to the second state in response to the suction force to draw an initial volume of bodily fluid into the portion of the sequestration chamber. The actuator is configured to be transitioned to the second configuration after the initial volume of bodily fluid is drawn into the sequestration chamber to (1) sequester the sequestration chamber from the inlet, and (2) allow a subsequent volume of bodily fluid to flow from the inlet to the outlet in response to the suction force.

DETAILED DESCRIPTION

Figure 1:
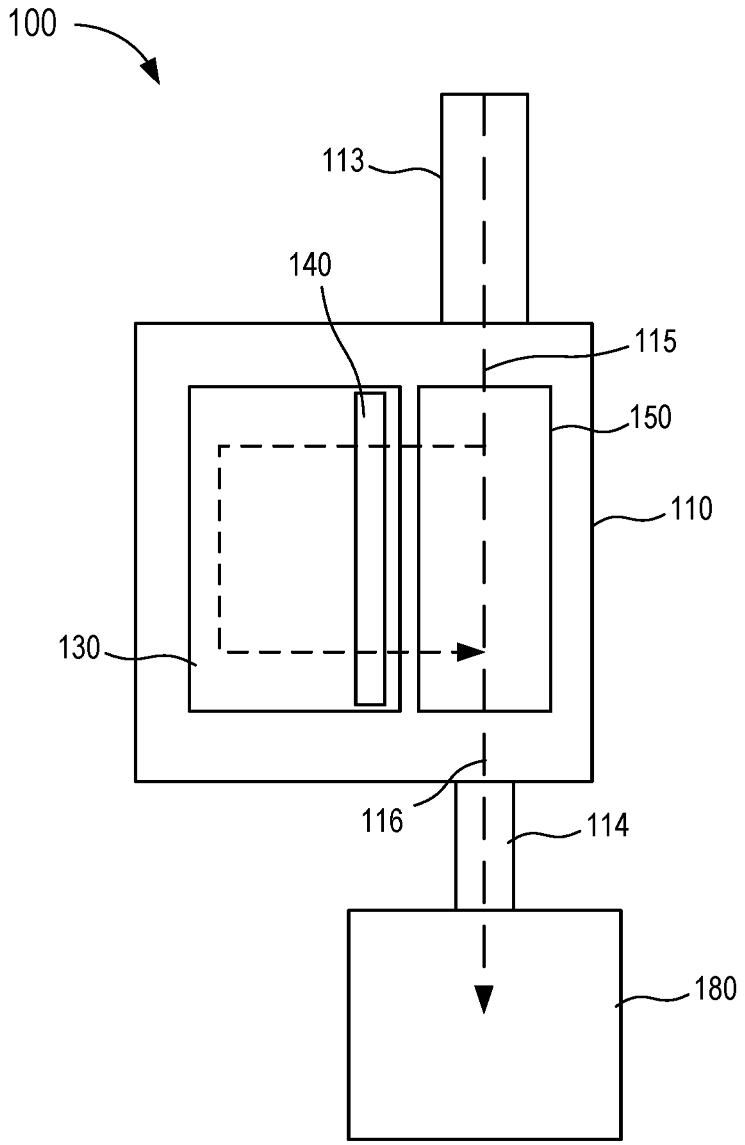
FIG. 1 is a schematic illustration of a fluid control device according to an embodiment.
Figure 2:
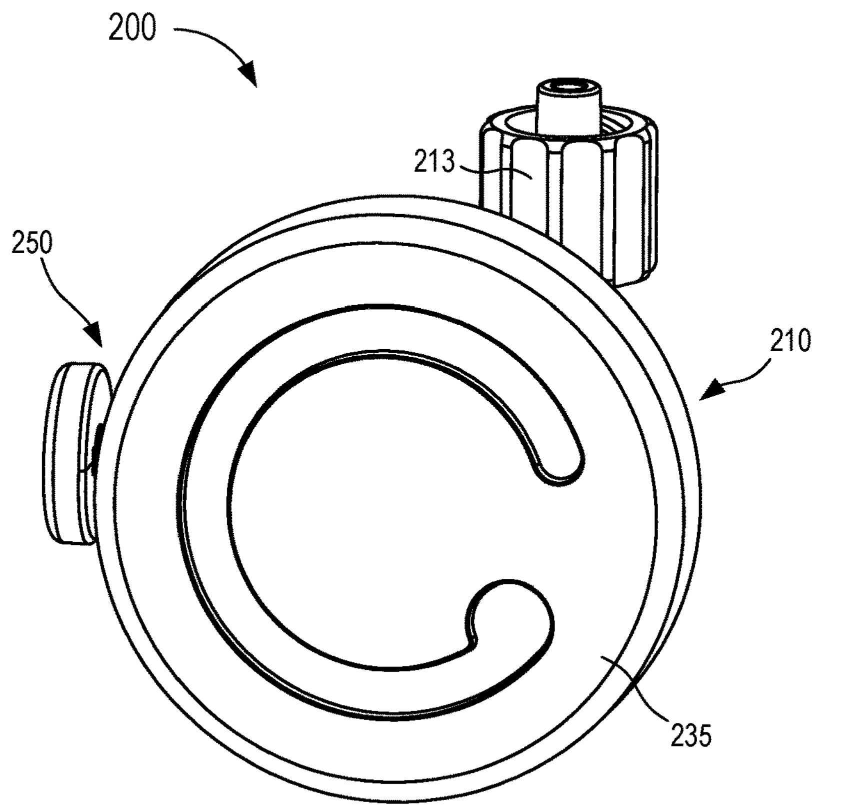
FIGS. 2 and 3 are a front perspective view and a rear perspective view, respectively, of a fluid control device according to an embodiment.
Figure 3:
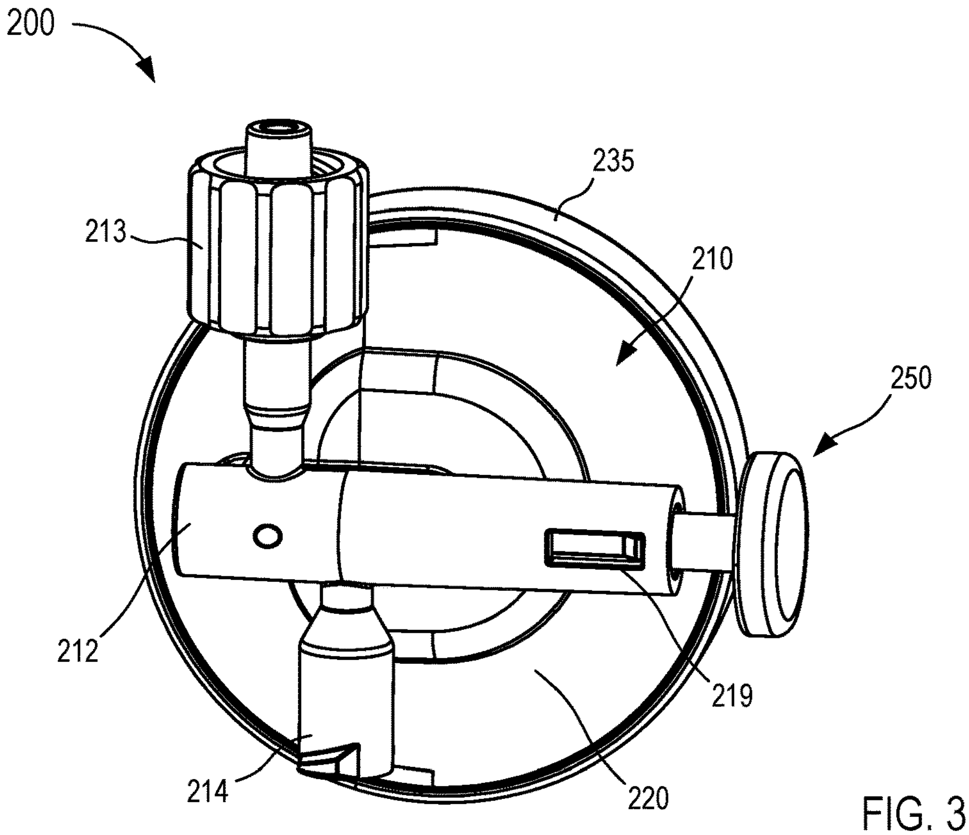
Figure 4:
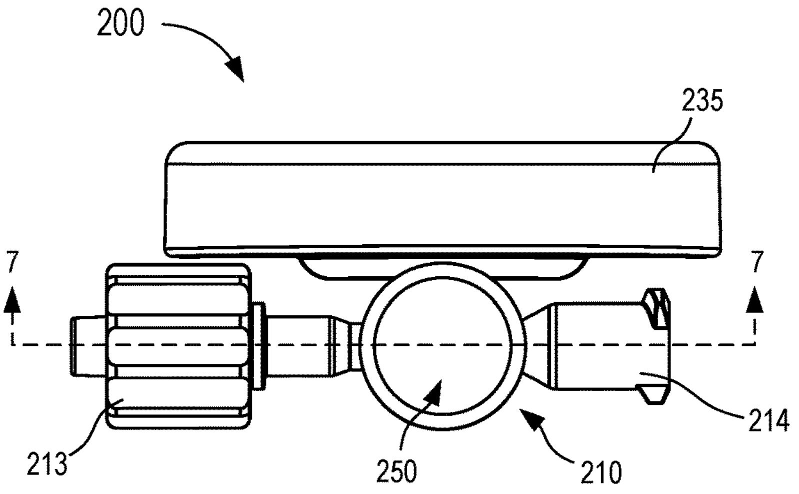
FIGS. 4 and 5 are a side view and a top view, respectively, of the fluid control device of FIG. 2.
Figure 5:
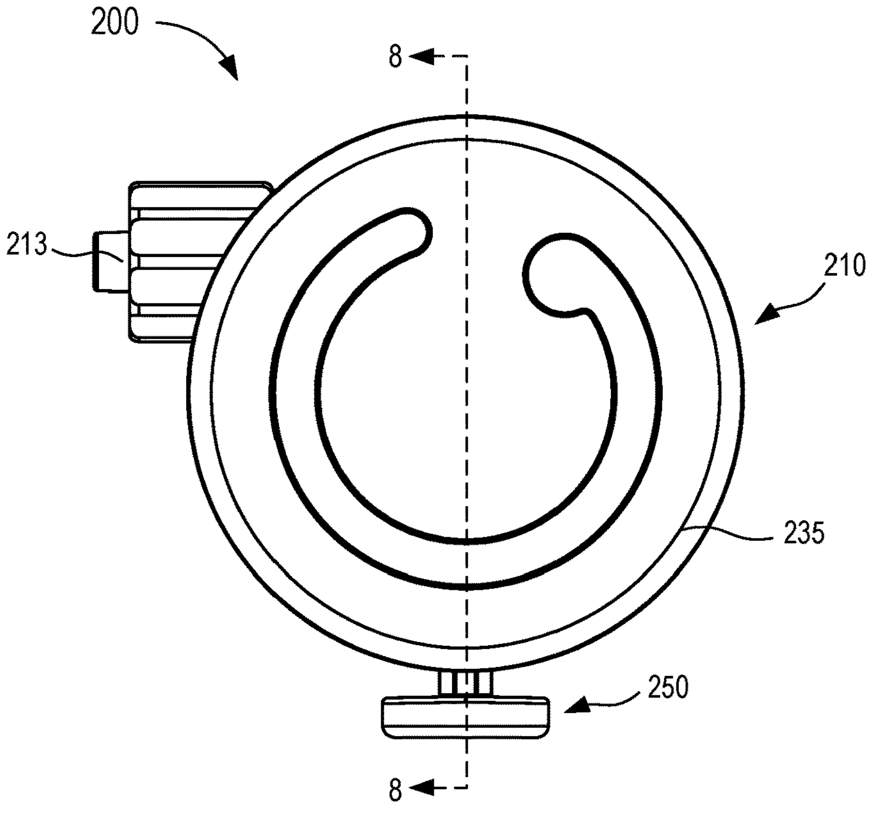

Devices and methods for collecting, diverting, sequestering, isolating, etc. an initial volume of bodily fluid to reduce contamination in subsequently procured bodily fluid samples are described herein. Any of the fluid control devices described herein can be configured to receive, procure, and/or transfer a flow, bolus, volume, etc., of bodily fluid. A first reservoir, channel, flow path, or portion of the device can receive an initial amount of the bodily fluid flow, which then can be substantially or fully sequestered therein (e.g., contained or retained, circumvented, isolated, segregated, vapor-locked, separated, and/or the like). In some instances, contaminants such as dermally residing microbes or the like can be included and/or entrained in the initial amount of the bodily fluid and likewise are sequestered in or by the first reservoir or first portion of the device. Once the initial amount is sequestered, any subsequent amount of the bodily fluid flow can be diverted, channeled, directed, and/or otherwise allowed to flow to or through a second portion of the device, and/or any additional flow path(s). Based at least in part on the initial amount being sequestered, the subsequent amount(s) of bodily fluid can be substantially free from contaminants that may otherwise produce inaccurate, distorted, adulterated, and/or false results in some diagnostics and/or testing. In some instances, the initial amount of bodily fluid also can be used, for example, in other testing such as those less affected by the presence of contaminants, can be discarded as a waste volume, can be infused back into the patient, and/or can be used for any other suitable clinical application.

In some embodiments, a feature of the fluid control devices and/or methods described herein is the use of an external negative pressure source (e.g., provided by a fluid collection device or any other suitable means) that can (1) overcome physical patient challenges which can limit and/or prevent a sufficient pressure differential to fully engage the sequestration chamber and/or to transition fluid flow to the fluid collection device (e.g., a differential in blood pressure to ambient air pressure); (2) result in proper filling of the sequestration chamber with a clinically validated and/or desirable volume of bodily fluid; (3) result in efficient, timely, and/or user-accepted consistency with the bodily fluid collection process; and/or (4) provide a means of transitioning fluid flow (e.g., automatically or by manipulation to move any number of physical components of the system or by changing, switching, engaging, and/or otherwise providing desired fluid flow dynamics) to enable sequestration and/or isolation of the initial amount (e.g., a pre-sample) and collection of a subsequent sample.

In some embodiments, for example, an apparatus for procuring bodily fluid samples with reduced contamination includes a housing, an actuator, and a flow controller. The housing forms at least a portion of a sequestration chamber, and has an inlet configured to be fluidically coupled to a bodily fluid source, and an outlet configured to be fluidically coupled to a fluid collection device. The fluid collection device exerts a suction force in at least a portion of the housing when fluidically coupled to the outlet. The actuator is coupled to the housing and has a first configuration in which the inlet is in fluid communication with the sequestration chamber, and a second configuration in which the inlet is in fluid communication with the outlet and is fluidically isolated from the sequestration chamber. The flow controller is disposed in the housing and defines a portion of the sequestration chamber. The flow controller has a first state in which the portion of the sequestration chamber has a first volume, and a second state in which the portion of the sequestration chamber has a second volume greater than the first volume. When the actuator is in the first configuration, the flow controller transitions from the first state to the second state in response to the suction force to draw an initial volume of bodily fluid into the portion of the sequestration chamber. The actuator is configured to be transitioned to the second configuration after the initial volume of bodily fluid is drawn into the sequestration chamber to (1) sequester the sequestration chamber from the inlet, and (2) allow a subsequent volume of bodily fluid to flow from the inlet to the outlet in response to the suction force.

In some embodiments, an apparatus for procuring bodily fluid samples with reduced contamination includes a housing, an actuator, and a flow controller. The housing forms at least a portion of a sequestration chamber, and has an inlet configured to be fluidically coupled to a bodily fluid source, and an outlet configured to be fluidically coupled to a fluid collection device. The fluid collection device exerts a suction force in at least a portion of the housing when fluidically coupled to the outlet. The actuator is coupled to the housing and has a first configuration in which the inlet is in fluid communication with the sequestration chamber, and a second configuration in which the inlet is in fluid communication with the outlet and is fluidically isolated from the sequestration chamber. The flow controller is disposed in the housing and defines a portion of the sequestration chamber. The flow controller has a first a first state in which a first side of the flow controller is in contact with at least a portion of a first surface of the sequestration chamber, and a second state in which a second side of the flow controller is in contact with at least a portion of a second surface of the sequestration chamber, opposite the first surface. The flow controller transitions from the first state to the second state when the actuator is in the first configuration, as a result of the suction force being exerted on the second side of the flow controller to draw an initial volume of bodily fluid into a portion of the sequestration chamber defined between the first surface and the first side of the flow controller. The actuator is configured to be transitioned to the second configuration after the initial volume of bodily fluid is drawn into the sequestration chamber to (1) sequester the sequestration chamber from the inlet, and (2) allow a subsequent volume of bodily fluid to flow from the inlet to the outlet in response to the suction force.

In some embodiments, a fluid control device can include a housing, a flow controller, and an actuator. The housing has an inlet and an outlet, and forms a sequestration chamber. The inlet is configured to be placed in fluid communication with a bodily fluid source. The outlet is configured to be placed in fluid communication with a fluid collection device configured to exert a suction force within at least a portion of the housing. The actuator is coupled to the housing and is configured to establish fluid communication between the inlet and the sequestration chamber when in a first state and to establish fluid communication between the inlet and the outlet when placed in a second state. The flow controller is disposed in the sequestration chamber and is configured to transition from a first state to a second state in response to the suction force when the actuator is in its first state to allow an initial volume of bodily fluid to flow into a portion of the sequestration chamber. The portion of the sequestration chamber has a first volume when the flow controller is in the first state and a second volume greater than the first volume when the flow controller is in the second state. The actuator is configured to be transitioned to its second state after the initial volume of bodily fluid is received in the portion of the sequestration chamber to (1) sequester the sequestration chamber, and (2) allow a subsequent volume of bodily fluid to flow from the inlet to the outlet in response to the suction force.

In some embodiments, a method for procuring bodily fluid samples with reduced contamination using a fluid control device having a housing, an actuator, and a flow controller includes establishing fluid communication between a bodily fluid source and an inlet of the housing. A fluid collection device is coupled to an outlet of the housing and exerts a suction force within at least a portion of the housing when coupled to the outlet. The flow controller is transitioned from a first state to a second state in response to the suction force, increasing a volume of a sequestration chamber collectively defined by the flow controller and a portion of the housing. In response to the increase in volume, a first portion of the sequestration chamber receives a volume of air contained in a flow path defined between the bodily fluid source and the sequestration chamber, and a second portion of the sequestration chamber receives an initial volume of bodily fluid. The actuator is transitioned from a first configuration to a second configuration after receiving the initial volume of bodily fluid in the second portion of the sequestration chamber to (1) sequester the sequestration chamber and (2) allow a subsequent volume of bodily fluid to flow from the inlet to the outlet in response to the suction force.

In some embodiments, a method for procuring a bodily fluid sample with reduced contamination using a fluid control device having a housing, a flow controller, and an actuator can include, for example, establishing fluid communication between a bodily fluid source and an inlet of the housing. A fluid collection device is fluidically coupled to an outlet of the housing. The flow controller is transitioned from a first state to a second state in response to a suction force exerted by the fluid collection device to increase a volume of a first portion of the sequestration chamber and a second portion of the sequestration chamber. The first portion of the sequestration chamber receives a volume of air contained in a flow path defined between the bodily fluid source and the sequestration chamber in response to the increase in the volume of the first portion of the sequestration chamber the second portion of the sequestration chamber. The second portion of the sequestration chamber receives an initial volume of bodily fluid in response to the increase in the volume of the first portion of sequestration chamber and the second portion of the sequestration chamber. After receiving the initial volume of bodily fluid in the second portion of the sequestration chamber, the actuator is transitioned from a first state to a second state to (1) sequester the sequestration chamber and (2) allow a subsequent volume of bodily fluid (e.g., the bodily fluid sample) to flow from the inlet to the outlet in response to the suction force.

Any of the embodiments and/or methods described herein can be used in the procurement of clean or substantially unadulterated bodily fluid samples such as, for example, blood samples. In some instances, bodily fluid samples (e.g., blood samples) can be tested for the presence of one or more potentially undesirable microbes, such as bacteria (e.g., Gram-Positive bacteria and/or Gram-Negative bacteria), fungi, yeast (e.g., Candida), and/or the like. Various technologies can be employed to assist in the detection of the presence of microbes as well as other types of biological matter, specific types of cells, biomarkers, proteins, antigens, enzymes, blood components, and/or the like during diagnostic testing. Examples include but are not limited to molecular polymerase chain reaction (PCR), magnetic resonance and other magnetic analytical platforms, automated microscopy, spatial clone isolation, flow cytometry, whole blood ("culture free") specimen analysis (e.g., NGS) and associated technologies, morphokinetic cellular analysis, and/or other common or evolving and advanced technologies to characterize patient specimens and/or to detect, identify, type, categorize, and/or characterize specific organisms, antibiotic susceptibilities, and/or the like.

For example, in some instances, microbial testing can include incubating patient samples in one or more vessels that may contain culture media (e.g., a nutrient rich and/or environmentally controlled medium to promote growth, and/or other suitable medium(s)), common additives, and/or other types of solutions conducive to microbial growth. Any microbes and/or organisms present in the patient sample flourish and/or grow over time in the culture medium (e.g., a variable amount of time from less than an hour to more than several days—which can be longer or shorter depending on the diagnostic technology employed). The presence of the microbes and/or organisms can be detected (e.g., by observing carbon dioxide levels and/or other detection methods) using automated, continuous monitoring, and/or other methods specific to the analytical platform or technology used for detection, identification, and/or the like. The presence of microbes and/or organisms in the culture medium suggests the presence of the same microbes and/or organisms in the patient sample, which in turn, suggests the presence of the same microbes and/or organisms in the bodily fluid of the patient from whom the sample was obtained. In other instances, a bodily fluid sample may be analyzed directly (i.e., not incubated) for the presence of microbes and/or organisms. When the presence of microbes is identified in the sample used for testing, the patient may be diagnosed and prescribed one or more antibiotics or other treatments specifically designed to treat or otherwise remove the undesired microbes and/or organisms from the patient.

Patient samples, however, can become contaminated during procurement and/or otherwise can be susceptible to false results. For example, microbes from a bodily surface (e.g., dermally residing microbes) that are dislodged during the specimen procurement process (e.g., either directly or indirectly via tissue fragments, hair follicles, sweat glands, and other skin adnexal structures) can be subsequently transferred to a culture medium, test vial, or other suitable specimen collection or transfer vessel with the patient sample and/or otherwise included in the specimen that is to be analyzed. Another possible source of contamination is from the person drawing the patient sample. For example, equipment, supplies, and/or devices used during a patient sample procurement process often include multiple fluidic interfaces (e.g., patient to needle, needle to transfer adapter, transfer adapter to sample vessel, catheter hub to syringe, syringe to transfer adapter, needle/tubing to sample vessels, and/or any other fluidic interface or any combination(s) thereof), each of which can introduce points of potential contamination. In some instances, such contaminants may thrive in a culture medium and/or may be otherwise identified, thereby increasing a risk or likelihood of a false positive microbial test result, which may inaccurately reflect the presence or lack of such microbes within the patient (i.e., in vivo).

Such inaccurate results because of contamination and/or adulteration are a concern when attempting to diagnose or treat a wide range of suspected illnesses, diseases, infections, patient conditions, and/or other maladies. For example, false results from microbial tests may lead to a patient being unnecessarily subjected to one or more antimicrobial therapies, and/or may lead to misdiagnosis and/or delayed treatment of a patient illness, any of which may cause serious side effects or consequences for the patient including, for example, death. As such, false results can produce an unnecessary burden and expense on the health care system due to extended length of patient stay and/or other complications associated with erroneous treatments. The use of diagnostic imaging equipment to arrive at these false results is also a concern from both a cost perspective and a patient safety perspective as unnecessary exposure to concentrated radiation associated with a variety of imaging procedures (e.g., CT scans) has many known adverse effects on long-term patient health.

As used in this specification and/or any claims included herein, the singular forms “a,” “an,” and “the” include plural referents unless the context clearly dictates otherwise. Thus, for example, the term “a member” is intended to mean a single member or a combination of members, “a material” is intended to mean one or more materials, and/or the like.

As used herein, “bodily fluid” can include any fluid obtained directly or indirectly from a body of a patient. For example, “bodily fluid” includes, but is not limited to, blood, cerebrospinal fluid, urine, bile, lymph, saliva, synovial fluid, serous fluid, pleural fluid, amniotic fluid, mucus, sputum, vitreous, air, and/or the like, or any combination thereof.

As used herein, the words “proximal” and “distal” refer to the direction closer to and away from, respectively, a user who would place a device into contact with a patient. Thus, for example, the end of a device first touching the body of a patient would be a distal end of the device, while the opposite end of the device (e.g., the end of the device being manipulated by the user) would be a proximal end of the device.

As used herein, the terms “about,” “approximately,” and/or “substantially” when used in connection with stated value(s) and/or geometric structure(s) or relationship(s) is intended to convey that the value or characteristic so defined is nominally the value stated or characteristic described. In some instances, the terms “about,” “approximately,” and/or “substantially” can generally mean and/or can generally contemplate a value or characteristic stated within a desirable tolerance (e.g., plus or minus 10% of the value or characteristic stated). For example, a value of about 0.01 can include 0.009 and 0.011, a value of about 0.5 can include 0.45 and 0.55, a value of about 10 can include 9 to 11, and a value of about 1000 can include 900 to 1100. Similarly, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms “about,” “approximately,” and/or “substantially” can be used herein to account for such tolerances and/or considerations.

As used herein, the terms “pre-sample,” “first,” and/or “initial,” can be used interchangeably to describe an amount, portion, or volume of bodily fluid that is collected and/or sequestered prior to procuring a “sample” volume. A “pre-sample,” “first,” and/or “initial” volume can be a predetermined, defined, desired, and/or given amount of bodily fluid. For example, a predetermined and/or desired pre-sample volume of bodily fluid can be a drop of bodily fluid, a few drops of bodily fluid, a volume of about 0.1 milliliter (mL), about 0.2 mL, about 0.3 mL, about 0.4 mL, about 0.5 mL, about 1.0 mL, about 2.0 mL, about 3.0 mL, about 4.0 mL, about 5.0 mL, about 10.0 mL, about 20.0 mL, about 50.0 mL, and/or any volume or fraction of a volume therebetween. In other embodiments, a pre-sample volume can be greater than 50 mL or less than 0.1 mL. In some specific embodiments, a predetermined and/or desired pre-sample volume can be between about 0.1 mL and about 5.0 mL. In other embodiments, a pre-sample volume can be, for example, a combined volume of any number of lumen (e.g., lumen that form at least a portion of a flow path from the bodily fluid source to an initial collection chamber, portion, reservoir, etc.).

As used herein, the terms “sample,” “second,” and/or “subsequent” can be used interchangeably to describe an amount, portion, or volume of bodily fluid that is used, for example, in one or more sample or diagnostic tests. A “sample” volume can be either a random volume or a predetermined or desired volume of bodily fluid collected after collecting, sequestering, and/or isolating a pre-sample volume of bodily fluid. In some embodiments, a desired sample volume of bodily fluid can be about 10 mL to about 60 mL. In other embodiments, a desired sample volume of bodily fluid can be less than 10 mL or greater than 60 mL. In some embodiments, for example, a sample volume can be at least partially based on one or more tests, assays, analyses, and/or processes to be performed on the sample volume.

The embodiments described herein can be configured to transfer bodily fluid substantially free of contaminants to one or more fluid collection device(s). In some embodiments, a fluid collection device can include, but is not limited to, any suitable vessel, container, reservoir, bottle, adapter, dish, vial, syringe, device, diagnostic and/or testing machine, and/or the like. In some embodiments, a fluid collection device can be substantially similar to or the same as known sample containers such as, for example, a Vacutainer® (manufactured by Becton Dickinson and Company (BD)), a BacT/ALERT® SN or BacT/ALERT® FA (manufactured by Biomerieux, Inc.), and/or any suitable reservoir, vial, microvial, microliter vial, nanoliter vial, container, microcontainer, nanocontainer, and/or the like. In some embodiments, a fluid collection device can be substantially similar to or the same as any of the sample reservoirs described in U.S. Pat. No. 8,197,420 entitled, "Systems and Methods for Parenterally Procuring Bodily-Fluid Samples with Reduced Contamination," filed Dec. 13, 2007 ("the 420 Patent"), the disclosure of which is incorporated herein by reference in its entirety.

In some embodiments, a fluid collection device can be devoid of contents prior to receiving a sample volume of bodily fluid. For example, in some embodiments, a fluid collection device or reservoir can define and/or can be configured to define or produce a vacuum or suction such as, for example, a vacuum-based collection tube (e.g., a Vacutainer®), a syringe, and/or the like. In other embodiments, a fluid collection device can include any suitable additives, culture media, substances, enzymes, oils, fluids, and/or the like. For example, a fluid collection device can be a sample or culture bottle including, for example, an aerobic or anaerobic culture medium. The sample or culture bottle can be configured to receive a bodily fluid sample, which can then be tested (e.g., after incubation via in vitro diagnostic (IVD) tests, and/or any other suitable test) for the presence of, for example, Gram-Positive bacteria, Gram-Negative bacteria, yeast, fungi, and/or any other organism. In some instances, if such a test of the culture medium yields a positive result, the culture medium can be subsequently tested using a PCR-based system to identify a specific organism. In some embodiments, a sample reservoir can include, for example, any suitable additive or the like in addition to or instead of a culture medium. Such additives can include, for example, heparin, citrate, ethylenediaminetetraacetic acid (EDTA), oxalate, sodium polyanethol sulfonate (SPS), and/or the like. In some embodiments, a fluid collection device can include any suitable additive or culture media and can be evacuated and/or otherwise devoid of air.

While the term "culture medium" can be used to describe a substance configured to react with organisms in a bodily fluid (e.g., microorganisms such as bacteria) and the term "additive" can be used to describe a substance configured to react with portions of the bodily fluid (e.g., constituent cells of blood, serum, synovial fluid, etc.), it should be understood that a sample reservoir can include any suitable substance, liquid, solid, powder, lyophilized compound, gas, etc. Moreover, when referring to an "additive" within a sample reservoir, it should be understood that the additive could be a culture medium, such as an aerobic culture medium and/or an anaerobic culture medium contained in a culture bottle, an additive and/or any other suitable substance or combination of substances contained in a culture bottle and/or any other suitable reservoir such as those described above. That is to say, the embodiments described herein can be used with any suitable fluid reservoir or the like containing any suitable substance or combination of substances.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly (butyric acid), poly(valeric acid), polyurethanes, and/or blends and copolymers thereof. Examples of non-biodegradable polymers include nylons, polyesters, polycarbonates, polyacrylates, polysiloxanes (silicones), polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

The embodiments described herein and/or portions thereof can include components formed of one or more parts, features, structures, etc. When referring to such components it should be understood that the components can be formed by a singular part having any number of sections, regions, portions, and/or characteristics, or can be formed by multiple parts or features. For example, when referring to a structure such as a wall or chamber, the structure can be considered as a single structure with multiple portions, or as multiple, distinct substructures or the like coupled to form the structure. Thus, a monolithically constructed structure can include, for example, a set of substructures. Such a set of substructures may include multiple portions that are either continuous or discontinuous from each other. A set of substructures can also be fabricated from multiple items or components that are produced separately and are later joined together (e.g., via a weld, an adhesive, or any suitable method).

While some of the embodiments are described herein as being used for procuring bodily fluid for one or more culture sample testing, it should be understood that the embodiments are not limited to such a use. Any of the embodiments and/or methods described herein can be used to transfer a flow of bodily fluid to any suitable device that is placed in fluid communication therewith. Thus, while specific examples are described herein, the devices, methods, and/or concepts are not intended to be limited to such specific examples.

Referring now to the drawings, FIG. 1 is a schematic illustration of a fluid control device 100 according to an embodiment. Generally, the fluid control device 100 (also referred to herein as "control device" or "device") is configured to withdraw bodily fluid from a patient. A first portion or amount (e.g., an initial amount) of the withdrawn bodily fluid is sequestered from a second portion or amount (e.g., a subsequent amount) of the withdrawn bodily fluid. In some instances, contaminants or the like can be sequestered within the first portion or amount, leaving the second portion or amount substantially free of contaminants. The second portion or amount of bodily fluid can then be used as a biological sample in one or more tests (e.g., a blood culture test or the like), as described in more detail herein. The first portion or amount of bodily fluid can be discarded as waste, reinfused into the patient, or used in any suitable test that is less likely to produce false, inaccurate, distorted, inconsistent, and unreliable results as a result of potential contaminants contained therein.

The control device 100 includes a housing 110, a flow controller 140, and an actuator 150. The housing 110 of the device 100 can be any suitable shape, size, and/or configuration. For example, in some embodiments, the housing 110 can have a size that is at least partially based on an initial amount or volume of bodily fluid configured to be transferred into and/or sequestered within a portion of the housing 110. In some embodiments, the housing 110 can have a size and/or shape configured to increase the ergonomics and/or ease of use associated with the device 100. Moreover, in some embodiments, one or more portions of the housing 110 can be formed of a relatively transparent material configured to allow a user to visually inspect and/or verify a flow of bodily fluid through at least a portion of the housing 110.

The housing 110 has and/or forms an inlet 113, an outlet 114, and a sequestration chamber 130. The inlet 113 is configured to fluidically couple to a lumen-containing device, which in turn, can place the housing 110 in fluid communication with a bodily fluid source. For example, the housing 110 can be coupled to and/or can include a lumen-containing device that is in fluid communication with the inlet 113 and that is configured to be percutaneously disposed in a patient (e.g., a butterfly needle, intravenous (IV) catheter, peripherally inserted central catheter (PICC), intermediary lumen-containing device, and/or the like). Thus, bodily fluid can be transferred from the patient and/or other bodily fluid source to the housing 110 via the inlet 113, as described in further detail herein. The outlet 114 can be placed in fluid communication with a fluid collection device 180 (e.g., a fluid or sample reservoir, syringe, evacuated container, culture bottle, etc.). As described in further detail herein, the control device 100 can be used and/or manipulated to selectively transfer a volume of bodily fluid from a bodily fluid source, through the inlet 113, the housing 110, and the outlet 114 to the fluid collection device 180.

The housing 110 can define at least a portion of any number of fluid flow paths. For example, as shown in FIG. 1, the housing 110 defines one or more fluid flow paths 115 between the inlet 113 and the sequestration chamber 130 and/or one or more fluid flow paths 116 between the inlet 113 and the outlet 114. As described in further detail herein, the control device 100 and/or the housing 110 can be configured to transition between any number of states, operating modes, and/or configurations to selectively control bodily fluid flow through at least one of the fluid flow paths 115 and/or 116. Moreover, the control device 100 and/or the housing 110 can be configured to transition automatically (e.g., based on pressure differential, time, electronically, saturation of a membrane, an absorbent and/or barrier material, etc.) or via intervention (e.g., user intervention, mechanical intervention, or the like).

The sequestration chamber 130 is at least temporarily placed in fluid communication with the inlet 113 via the fluid flow path(s) 115. As described in further detail herein, the sequestration chamber 130 is configured to (1) receive a flow and/or volume of bodily fluid from the inlet 113 and (2) sequester (e.g., separate, segregate, contain, retain, isolate, etc.) the flow and/or volume of bodily fluid therein. The sequestration chamber 130 can have any suitable arrangement such as, for example, those described herein with respect to specific embodiments. It should be understood, however, that the control device 100 and/or the housing 110 can have a sequestration chamber 130 arranged in any suitable manner and therefore, the sequestration chamber 130 is not intended to be limited to those shown and described herein. For example, in some embodiments, the sequestration chamber 130 can be at least partially formed by the housing 110. In other embodiments, the sequestration chamber 130 can be a reservoir placed and/or disposed within a portion of the housing 110. In other embodiments, the sequestration chamber 130 can be formed and/or defined by a portion of the fluid flow path 115. That is to say, the housing 110 can define one or more lumens and/or can include one or more lumen defining device(s) configured to receive an initial flow or volume of bodily fluid from the inlet 113, thereby forming and/or functioning as the sequestration chamber 130.

The sequestration chamber 130 can have any suitable volume and/or fluid capacity. For example, in some embodiments, the sequestration chamber 130 can have a volume and/or fluid capacity between about 0.1 mL and about 5.0 mL. In some embodiments, the sequestration chamber 130 can have a volume measured in terms of an amount of bodily fluid (e.g., the initial or first amount of bodily fluid) configured to be transferred in the sequestration chamber 130. For example, in some embodiments, the sequestration chamber 130 can have a volume sufficient to receive an initial volume of bodily fluid as small as a microliter or less of bodily fluid (e.g., a volume as small as 20 drops of bodily fluid, 10 drops of bodily fluid, 5 drops of bodily fluid, a single drop of bodily fluid, or any suitable volume therebetween). In other embodiments, the sequestration chamber 130 can have a volume sufficient to receive an initial volume of bodily fluid up to, for example, about 5.0 mL, 10.0 mL, 15.0 mL, 10.0 mL, 30.0 mL, 40.0 mL, 50.0 mL, or more. In some embodiments, the sequestration chamber 130 can have a volume that is equal to at least some of the volumes of one or more lumen(s) placing the sequestration chamber 130 in fluid communication with the bodily fluid source (e.g., a combined volume of a lumen of a needle, the inlet 113, and at least a portion of the fluid flow path 115).

The outlet 114 of the housing 110 is in fluid communication with and/or is configured to be placed in fluid communication with the fluid flow paths 115 and/or 116. The outlet 114 can be any suitable outlet, opening, port, stopcock, lock (e.g., a luer lock), seal, coupler, valve (e.g. one-way, check valve, duckbill valve, umbrella valve, and/or the like), etc. and is configured to be physically and/or fluidically coupled to the fluid collection device 180. In some embodiments, the outlet 114 can be monolithically formed with the fluid collection device 180. In other embodiments, the outlet 114 can be at least temporarily coupled to the fluid collection device 180 via an adhesive, a resistance fit, a mechanical fastener, a threaded coupling, a piercing or puncturing arrangement, a number of mating recesses, and/or any other suitable coupling or combination thereof. In still other embodiments, the outlet 114 can be operably coupled to the fluid collection device 180 via an intervening structure (not shown in FIG. 1), such as sterile tubing and/or the like. In some embodiments, the arrangement of the outlet 114 can be such that the outlet 114 is physically and/or fluidically sealed prior to coupling to the fluid collection device 180. In some embodiments, the outlet 114 can be transitioned from a sealed configuration to an unsealed configuration in response to being coupled to the fluid collection device 180 and/or in response to a negative pressure differential between an environment within the outlet 114 and/or housing 110 and an environment within the fluid collection device 180.

Although the outlet 114 of the control device 100 and/or the housing 110 is described above as being fluidically coupled to and/or otherwise placed in fluid communication with the fluid collection device 180, in other embodiments, the device 100 can be used in conjunction with any suitable bodily fluid collection device, system, adapter, and/or the like. For example, in some embodiments, the device 100 can be used in or with any suitable fluid transfer device and/or adapter such as those described in U.S. Pat. No. 10,123,783 entitled, "Apparatus and Methods for Disinfection of a Specimen Container," filed Mar. 3, 2015 (referred to herein as "the '783 patent") and/or U.S. Patent Publication No. 2015/0342510 entitled, "Sterile Bodily-Fluid Collection Device and Methods," filed Jun. 2, 2015 (referred to herein as "the '510 publication"), the disclosure of each of which is incorporated herein by reference in its entirety.

The fluid collection device 180 can be any suitable device for at least temporarily containing a bodily fluid, such as, for example, any of those described in detail above (e.g., an evacuated container, a sample reservoir, a syringe, a culture bottle, etc.). In some embodiments, the fluid collection device 180 can be a sample reservoir that includes a vacuum seal that maintains negative pressure conditions (vacuum conditions) inside the sample reservoir, which in turn, can facilitate withdrawal of bodily fluid from the patient, through the control device 100, and into the sample reservoir, via a vacuum or suction force. In embodiments in which the fluid collection device 180 is an evacuated container or the like, the user can couple the fluid collection device 180 to the outlet 114 to initiate a flow of bodily fluid from the patient and into the device 100 such that a first or initial portion of the flow of bodily fluid is transferred into and sequestered by the sequestration chamber 130, and a second or subsequent portion of the flow of bodily fluid bypasses and/or is otherwise diverted away from the sequestration chamber 130 and into the fluid collection device 180 (e.g., via the outlet 114), as described in further detail herein.

The flow controller 140 of the device 100 is at least partially disposed within the housing 110 and is configured to control, direct, and/or otherwise facilitate a selective flow of fluid through at least a portion of the housing 110. More particularly, in some embodiments, the flow controller 140 can be disposed within and/or can at least partially define a portion of the sequestration chamber 130 and/or an inner volume of the sequestration chamber 130 that receives the initial flow or amount of bodily fluid. In some embodiments, the flow controller 140 can be disposed within the housing 110 such that one or more surfaces of the flow controller 140 and one or more inner surfaces of the housing 110 collectively define the sequestration chamber 130. Said another way, the flow controller 140 can be disposed within the sequestration chamber 130 such that an inner surface of the housing 110 at least partially defining the sequestration chamber 130 and one or more surfaces of the flow controller 140 collectively define a portion of the sequestration portion 130 and/or a volume within the sequestration chamber 130. In some embodiments, the flow controller 140 can form a barrier and/or otherwise can fluidically isolate at least a portion of the fluid flow path 115 from at least a portion of the fluid flow path 116. For example, the flow controller 140 can be disposed in the housing 110 such that a first side and/or surface of the flow controller 140 is selectively in fluid communication with the at least a portion of the fluid flow path 115 and/or the inlet 113, and a second side and/or surface of the flow controller 140 is selectively in fluid communication with at least a portion of the fluid flow path 116 and/or the outlet 114.

The flow controller 140 can be any suitable shape, size, and/or configuration. For example, the flow controller 140 can be, for example, a membrane, a diaphragm, a bladder, a plunger, a piston, a bag, a pouch, and/or any other suitable member having a desired stiffness, flexibility, and/or durometer. In some embodiments, the flow controller 140 can be configured to transition from a first state to a second state in response to a negative pressure differential and/or suction force exerted on at least a portion of the flow controller 140. For example, in some embodiments, the flow controller 140 can be a bladder configured to transition or "flip" from a first state to a second state in response to a negative pressure differential and/or suction force exerted on a surface of the bladder, as described in further detail herein with reference to specific embodiments.

The flow controller 140 can be in a first state prior to using the device 100 (e.g., a storage or non-use state) and in response to the outlet 114 be fluidically coupled to the fluid collection device 180 (e.g., a collection device defining or configured to define a negative pressure and/or suction force), the flow controller 140 can be transitioned to a second state. In some embodiments, the flow controller 140 can define at least a portion of the sequestration chamber 130 when the flow controller 140 is in the second state. In some embodiments, the arrangement of the flow controller 140 is such that the sequestration chamber 130 defines and/or has a first volume when the flow controller 140 is in the first state and a second volume, greater than the first volume, when the flow controller 140 is placed in the second state. As described in further detail herein, the increase in the volume of the sequestration chamber 130 can result in a suction force operable to draw the initial volume of bodily fluid into the sequestration chamber 130. Moreover, in some embodiments, the flow controller 140 can have a size, shape, and/or configuration that allows the sequestration chamber 130 to receive a volume of air or gas (e.g., a volume of air disposed in the flow path between the bodily fluid source and the sequestration portion) and the initial amount or volume of bodily fluid. In such embodiments, the flow controller 140 can be configured to define any number of portions, volumes, channels, etc., that can receive and/or contain at least one of a volume of air or the initial volume of bodily fluid.

In some embodiments, a size, shape, arrangement, and/or constituent material of the flow controller 140 can be configured and/or otherwise selected such that the flow controller 140 transitions from the first state to the second state in a predetermined manner and/or with a predetermined or desired rate. In some instances, controlling a rate at which the flow controller 140 transitions from the first state to the second state can, in turn, control and/or modulate a rate of bodily fluid flow into the sequestration chamber 130 and/or a magnitude of a suction force generated in the sequestration chamber 130 that is operable in drawing the initial volume of bodily fluid into the sequestration chamber 130. Although not shown in FIG. 1, in some embodiments, the housing 110 can include a valve, a membrane, a porous material, a restrictor, an orifice, and/or any other suitable member, device, and/or feature configured to modulate a suction force exerted on a surface of the flow controller 140, which in turn, can modulate the rate at which the flow controller 140 transitions from the first state to the second state.

In some instances, controlling a rate at which the flow controller 140 transitions and/or a magnitude of a pressure differential and/or suction force generated within the sequestration chamber 130 can reduce, for example, hemolysis of a blood sample and/or a likelihood of collapsing a vein (e.g., which is particularly important when procuring bodily fluid samples from fragile patients). In some instances, modulating the transitioning of the flow controller 140 and/or the pressure differential generated in the sequestration chamber 130 can at least partially control an amount or volume of bodily fluid transferred into the sequestration chamber 130 (i.e., can control a volume of the initial amount of bodily fluid).

The actuator 150 of the device 100 is at least partially disposed within the housing 110 and is configured to control, direct, and/or otherwise facilitate a selective flow of fluid through at least a portion of the housing 110. The actuator 150 can be any suitable shape, size, and/or configuration. For example, in some embodiments, the actuator 150 can be any suitable member or device configured to transition between a first state and a second state. In some embodiments, for example, the actuator 150 can be a valve, plunger, seal, membrane, bladder, flap, plate, rod, switch, and/or the like. In some embodiments, the actuator 150 can include one or more seals configured to selectively establish fluid communication between the fluid flow channels 113 and 116 when the actuator 150 is transitioned from a first state to a second state.

The actuator 150 can be actuated and/or transitioned between the first state and the second state in any suitable manner. For example, in some embodiments, transitioning the actuator 150 can include activating, pressing, moving, translating, rotating, switching, sliding, opening, closing, and/or otherwise reconfiguring the actuator 150. In some instances, the actuator 150 can transition between the first and the second state in response to a manual actuation by the user (e.g., manually exerting a force on a button, slider, plunger, switch, valve, rotational member, conduit, etc.). In other embodiments, the actuator 150 can be configured to automatically transition between the first state and the second state in response to a pressure differential (or lack thereof), a change in potential or kinetic energy, a change in composition or configuration (e.g., a portion of an actuator could at least partially dissolve or transform), and/or the like. In still other embodiments, the actuator 150 can be mechanically and/or electrically actuated or transitioned (e.g., via a motor and/or the like) based on a predetermined time, volume of bodily fluid received, volumetric flow rate of a flow of bodily fluid, flow velocity of a flow of bodily fluid, etc. While examples of actuators and/or ways in which an actuator can transition are provided, it should be understood that they have been presented by way of example only and not limitation.

In some embodiments, the actuator 150 can be configured to isolate, sequester, separate, and/or otherwise prevent fluid communication between at least a portion of the fluid flow path 115 and at least a portion of the fluid flow path 116 when in the first state and can be configured to place the fluid flow path 115 (or at least a portion thereof) in fluid communication with the fluid flow path 116 (or at least a portion thereof) when in the second state. In addition, the actuator 150 can be configured to sequester, separate, isolate, and/or otherwise prevent fluid communication between the sequestration chamber 130 and the inlet 113, the outlet 114, and/or at least a portion of the fluid flow paths 115 and 116. Accordingly, when the actuator 150 is placed in its second state, the sequestration chamber 130 can be sequestered and/or fluidically isolated from other flow paths or portions of the housing 110 and the inlet 113 can be placed in fluid communication with the outlet 114. As such, the actuator 150 can allow a subsequent volume of bodily fluid (e.g., a volume of bodily fluid after the initial volume of bodily fluid) to be transferred to the fluid collection device 180 fluidically coupled to the outlet 114, as described in further detail herein.

As described above, the device 100 can be used to procure a bodily fluid sample having reduced contamination from microbes such as, for example, dermally residing microbes, and/or the like. For example, in some instances, a user such as a doctor, physician, nurse, phlebotomist, technician, etc. can manipulate the device 100 to establish fluid communication between the inlet 113 and the bodily fluid source (e.g., a vein of a patient, cerebral spinal fluid (CSF) from the spinal cavity, urine collection, and/or the like). As a specific example, in some instances, the inlet 113 can be coupled to and/or can include a needle or the like that can be manipulated to puncture the skin of the patient and to insert at least a portion of the needle in the vein of the patient, thereby placing the inlet 113 in fluid communication with the bodily fluid source (e.g., the vein, an IV catheter, a PICC, etc.).

In some embodiments, once the inlet 113 is placed in fluid communication with the bodily fluid source (e.g., the portion of the patient), the outlet 114 can be fluidically coupled to the fluid collection device 180. As described above, in some embodiments, the fluid collection device 180 can be any suitable reservoir, container, and/or device configured to receive a volume of bodily fluid. For example, the fluid collection device 180 can be an evacuated reservoir or container that defines a negative pressure and/or can be a syringe that can be manipulated to produce a negative pressure. In some instances, coupling the outlet 114 to the fluid collection device 180 selectively exposes at least a portion of the fluid flow path 116 to the negative pressure and/or suction force within the fluid collection device 180. As described above, a portion and/or surface of the flow controller 140 can be in fluid communication with the fluid flow path 116 and, as such, the negative pressure and/or suction force can be exerted on the portion and/or surface of the flow controller 140. The negative pressure and/or suction force, in turn, can be operable to transition the flow controller 140 from its first state, in which the sequestration chamber 130 has the first volume, to its second state, in which the sequestration chamber 130 has the second volume, greater than the first volume. As such, an initial volume of bodily fluid can be drawn into the sequestration chamber 130 in response to the transitioning of the flow controller 140 (e.g., the increase in volume of the sequestration chamber 130 as a result of the flow controller 140 transitioning from the first state to the second state).

In some embodiments, for example, the flow controller 140 can be a bladder or the like configured to transition or "flip" in response to the negative pressure. The flow controller 140 can be configured to transition in a predetermined manner and/or with a predetermined rate, which in turn, can control, modulate, and/or otherwise determine one or more characteristics associated with a flow of an initial volume of bodily fluid into the sequestration chamber 130. In some embodiments, the flow controller 140 and, for example, one or more inner surfaces of the housing 110 can collective define a number of different portions of the sequestration chamber 130. In such embodiments, at least one of the portions of the sequestration chamber 130 can be configured to contain a volume of air that was drawn into the sequestration chamber 130 immediately before the initial volume of bodily fluid, as described in detail above. Thus, the transitioning of the flow controller 140 from the first state to the second state can result in the initial portion of the volume of bodily fluid (also referred to herein as an "initial volume" or a "first volume") flowing from the inlet 113, through at least a portion of the fluid flow path 115, and into the sequestration chamber 130. In some embodiments, transitioning the flow controller 140 from the first state to the second state can transition the control device 100 from a first or initial state or configuration to a second state or configuration in which the initial portion or volume of bodily fluid can flow in or through at least a portion the fluid flow path 115 and into the sequestration chamber 130.

The initial volume of bodily fluid can be any suitable volume of bodily fluid, as described above. For example, in some instances, the control device 100 can remain in the second state or configuration until a predetermined and/or desired volume (e.g., the initial volume) of bodily fluid is transferred to the sequestration chamber 130. In some embodiments, the initial volume can be associated with and/or at least partially based on a volume of the sequestration chamber 130 or a portion thereof (e.g., a volume sufficient to fill the sequestration chamber 130 or a desired portion of the sequestration chamber 130). In other embodiments, the initial volume of bodily fluid can be associated with and/or at least partially based on an amount or volume of bodily fluid that is equal to or greater than a volume associated with the fluid flow path defined between the bodily fluid source and the sequestration chamber 130. In still other embodiments, the control device 100 can be configured to transfer a flow of bodily fluid (e.g., the initial volume) into the sequestration chamber 130 until a pressure differential between the sequestration chamber 130 and the fluid flow path 115 and/or the bodily fluid source is brought into substantial equilibrium and/or is otherwise reduced below a desired threshold.

After the initial volume of bodily fluid is transferred and/or diverted into the sequestration chamber 130, the control device 100 can be transitioned from the second state or configuration to a third state or configuration. For example, in some embodiments, the actuator 150 can be transitioned from its first state to its second state when the initial volume of bodily fluid is transferred into the sequestration chamber 130, which in turn, places the control device 100 in its third state. More particularly, in some embodiments, the arrangement of the control device 100 and/or the sequestration chamber 130 can be such that a flow of bodily fluid into the sequestration chamber 130 substantially stops or slows in response to receiving the initial volume. In some embodiments, for example, the sequestration chamber 130 can receive the flow of bodily fluid (e.g., the initial volume of bodily fluid) until a pressure differential equalizes within the sequestration chamber 130 and/or between the sequestration chamber 130 and the fluid flow path 115 and/or the bodily fluid source. In some instances, the user can visually inspect a portion of the device 100 and/or housing 110 to determine that the initial volume of bodily fluid is disposed in the sequestration chamber 130 and/or that the flow of bodily fluid into the sequestration chamber 130 has slowed or substantially stopped. In some embodiments, the user can exert a force on the actuator 150 and/or can otherwise actuate the actuator 150 to transition the actuator 150 from its first state to its second state. In other embodiments, the actuator 150 can be transitioned automatically (e.g., without user intervention).

The transitioning of the actuator 150 from its first state to its second state (e.g., placing the control device 100 in its third state or configuration) can sequester, isolate, separate, and/or retain the initial volume of the bodily fluid in the sequestration chamber 130. As described in further detail herein, in some instances, contaminants such as, for example, dermally residing microbes or the like dislodged during the venipuncture event, other external sources of contamination, colonization of catheters and PICC lines that are used to collect samples, and/or the like can be entrained and/or included in the initial volume of the bodily fluid. Thus, such contaminants are sequestered in the sequestration chamber 130 when the initial volume is sequestered therein.

In addition to sequestering the initial volume of bodily fluid in the sequestration chamber 130, placing the actuator 150 in its second state can also establish fluid communication between at least a portion of the fluid flow paths 115 and 116 such that a subsequent volume(s) of bodily fluid can flow through at least a portion the fluid flow paths 115 and/or 116 from the inlet 113 to the outlet 114. For example, in some embodiments, transitioning the actuator 150 from its first state to its second state can, for example, open or close a port or valve, move one or more seals, move or remove one or more obstructions, define one or more portions of a flow path, and/or the like. With the fluid collection device 180 fluidically coupled to the outlet 114 and with the control device 100 being in the third state or configuration, the negative pressure differential and/or the suction force otherwise exerted on the flow controller 140 can be exerted on or through at least a portion of the fluid flow paths 115 and 116. Thus, any subsequent volume(s) of the bodily fluid can flow from the inlet 113, through at least a portion of the fluid flow paths 115 and 116, through the outlet 114, and into the fluid collection device 180. As described above, sequestering the initial volume of bodily fluid in the sequestration chamber 130 prior to collecting or procuring one or more sample volumes of bodily fluid (e.g., in the fluid collection device 180) reduces and/or substantially eliminates an amount of contaminants in the one or more sample volumes. Moreover, in some embodiments, the arrangement of the control device 100 can be such that the control device 100 cannot transition to the third state prior to collecting and sequestering the initial volume in the sequestration chamber 130.

FIGS. 2-11 illustrate a fluid control device 200 according to another embodiment. The fluid control device 200 (also referred to herein as "control device" or "device") can be similar in at least form and/or function to the device 100 described above with reference to FIG. 1. For example, as described above with reference to the device 100, in response to being placed in fluid communication with a negative pressure source (e.g., a suction or vacuum source), the device 200 can be configured to (1) withdraw bodily fluid from a bodily fluid source into the device 200, (2) divert and sequester a first portion or amount (e.g., an initial volume) of the bodily fluid in a portion of the device 200, and (3) allow a second portion or amount (e.g., a subsequent volume) of the bodily fluid to flow through the device 200—bypassing the sequestered initial volume—and into a fluid collection device fluidically coupled to the device 200. As such, contaminants or the like can be sequestered in or with the initial volume of bodily fluid, leaving the subsequent volume of bodily fluid substantially free of contaminants.

The fluid control device 200 (also referred to herein as "control device" or "device") includes a housing 210, a flow controller 240, and an actuator 250. In some embodiments, the control device 200 or at least a portion of the control device 200 can be arranged in a modular configuration in which one or more portions of the housing 210 and/or the actuator 250 can be physically and fluidically coupled (e.g., by an end user) to collectively form the control device 200. Similarly, in some embodiments, the control device 200 can be packaged, shipped, and/or stored independent of a fluid collection device (e.g., a sample reservoir, syringe, etc.) and/or an inlet device (e.g., a needle, catheter, peripheral intravenous line (M), peripherally inserted central catheter (PICC), etc.), which a user can couple to the control device 200 before or during use. In other embodiments, the control device 200 need not be modular. For example, in some embodiments, the control device 200 can be assembled during manufacturing and delivered to a supplier and/or end user as an assembled device. In some embodiments, the control device 200 can include and/or can be pre-coupled (e.g., during manufacturing and/or prior to being delivered to an end user) to a fluid collection device such as any of those described above. Similarly, in some embodiments, the control device 200 can include and/or can be pre-coupled to an inlet device such as any of those described herein.

The housing 210 of the control device 200 can be any suitable shape, size, and/or configuration. The housing 210 includes an actuator portion 212 and a sequestration portion 220. The actuator portion 212 of the housing 210 receives at least a portion of the actuator 250. The sequestration portion 220 of the housing 210 is coupled to a cover 235 and includes, receives, houses, and/or at least partially defines a sequestration chamber 230. As described in further detail herein, the housing 210 can include and/or can define a first port 217 and a second port 218, each of which establishes fluid communication between the actuator portion 212 and the sequestration portion 220 of the housing 210 to selectively control and/or allow a flow of fluid through one or more portions of the housing 210.

As shown in FIGS. 2-6, the actuator portion 212 of the housing 210 includes an inlet 213 and an outlet 214. The inlet 213 is configured to be placed in fluid communication with a bodily fluid source to receive a flow of bodily fluid therefrom, as described in detail above. For example, the inlet 213 can be coupled directly or indirectly to a lumen-containing device such as a needle, IV catheter, PICC line, and/or the like, which in turn, is in fluid communication with the bodily fluid source (e.g., inserted into a patient). The outlet 214 is configured to be fluidically coupled to a fluid collection device such as any of those described above. For example, the fluid collection device can be a sample reservoir, a syringe, an intermediary bodily fluid transfer device, adapter, or vessel (e.g., a transfer adapter similar to those described in the '783 patent), and/or the like. Moreover, the fluid collection device can define and/or can be manipulated to define a vacuum within the fluid collection device such that coupling the fluid collection device to the outlet 214 generates a negative pressure differential between one or more portions of the housing 210, as described in further detail herein.

As shown, for example, in FIGS. 7-11, the actuator portion 212 defines a fluid flow path 215 in fluid communication with the inlet 213 and a fluid flow path 216 in fluid communication with the outlet 214. More particularly, the fluid flow path 215 (e.g., a first fluid flow path) is configured to selectively place the inlet 213 in fluid communication with the first port 217 and the fluid flow path 216 (e.g., a second fluid flow path) is configured to selectively place the outlet 214 in fluid communication with the second port 218. In addition, after an initial volume of bodily fluid has been transferred into the sequestration chamber 230, fluid communication can be established between the fluid flow paths 215 and 216, thereby allowing a subsequent volume of bodily fluid to flow from the inlet 213, through at least a portion of the fluid flow paths 215 and 216, and to the outlet 214 (and/or to a fluid collection device coupled to the outlet 214), as described in further detail herein.

The sequestration portion 220 of the housing 210 can be any suitable shape, size, and/or configuration. As shown, for example, in FIGS. 6-8, the sequestration portion 220 includes and/or forms an inner surface, a portion of which is arranged and/or configured to form a first contoured surface 221. At least a portion of the first contoured surface 221 can form and/or define a portion of the sequestration chamber 230, as described in further detail herein. Furthermore, the first port 217 and the second port 218 are configured to form and/or extend through a portion of the first contoured surface 221 to selectively place the sequestration chamber 230 in fluid communication with the fluid flow paths 215 and 216, as described in further detail here.

Figure 6:
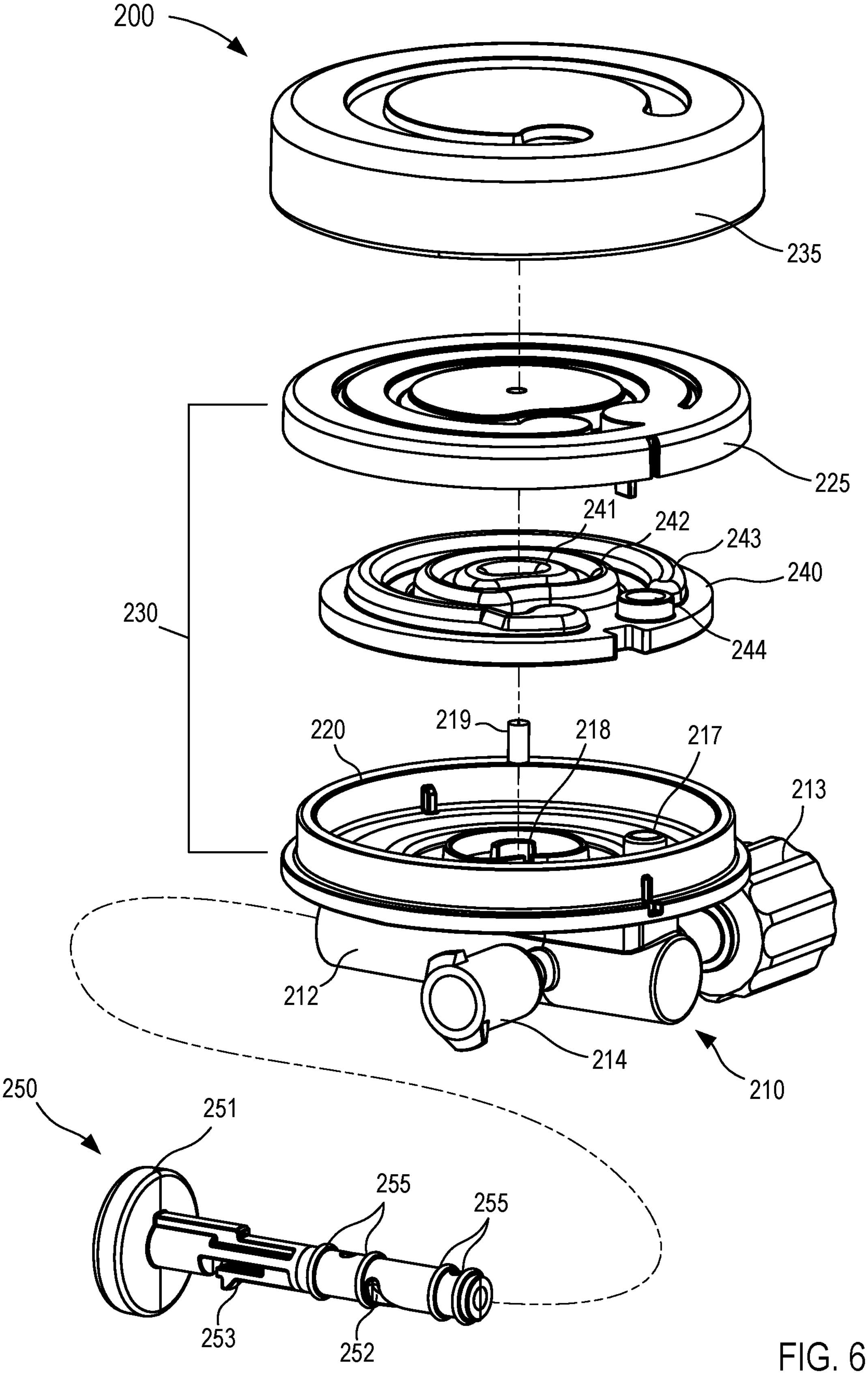
FIG. 6 is an exploded perspective view of the fluid control device of FIG. 2.
Figure 7:
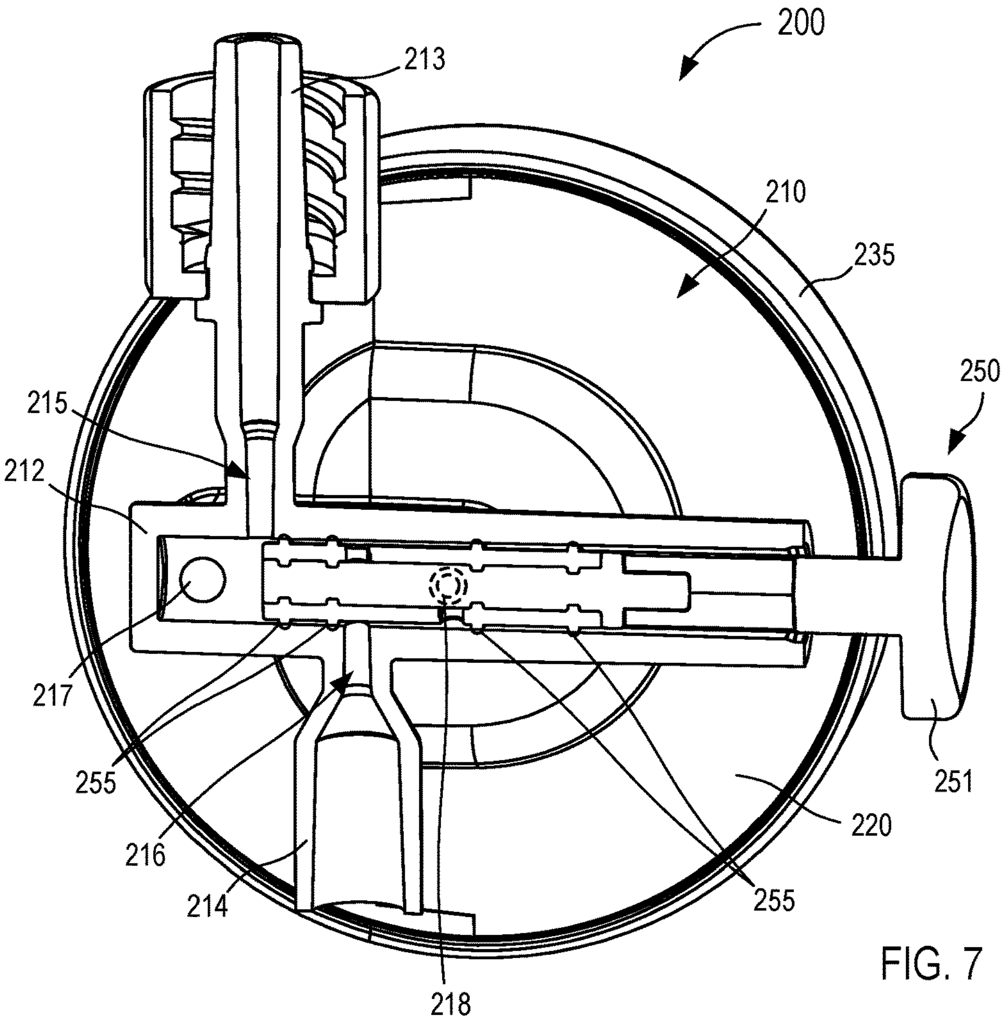
FIGS. 7 and 8 are each a cross-sectional view of the fluid control device of FIG. 2 taken along the line 7-7 in FIG. 4 and the line 8-8 in FIG. 5, respectively, shown in a first state.
Figure 8:
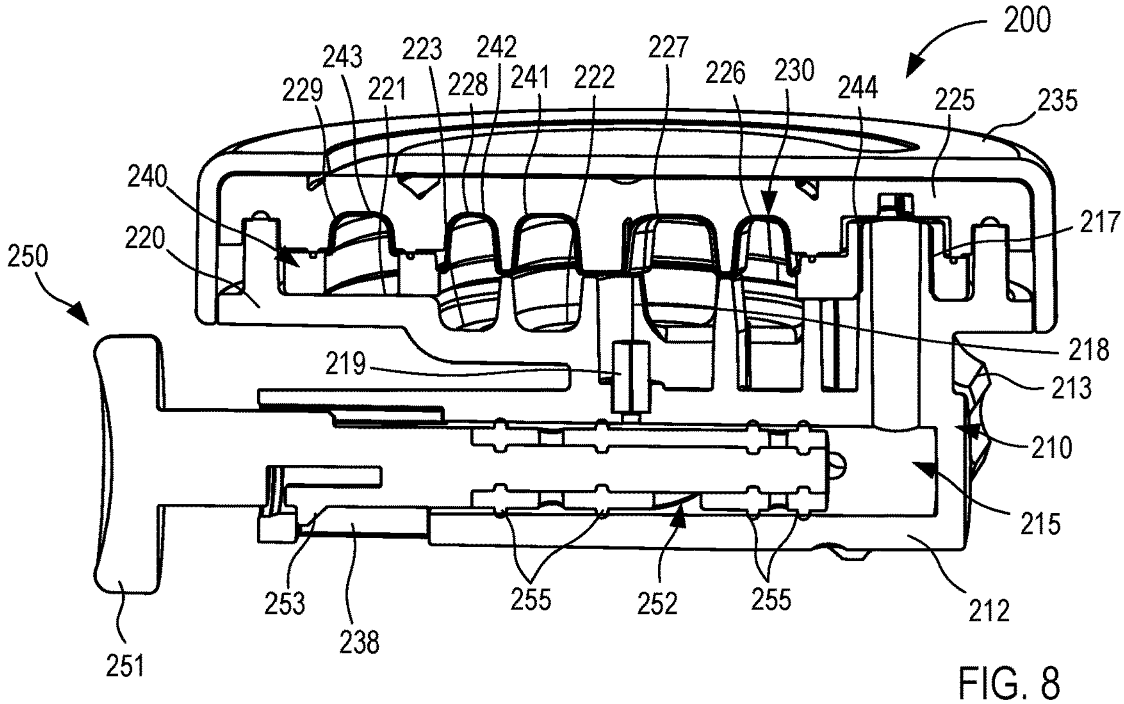

The sequestration portion 220 is configured to include, form, and/or house, a contour member 225 and the flow controller 240. More particularly, as shown in FIGS. 6-8, the sequestration portion 220 receives and/or is coupled to the contour member 225 such that the flow controller 240 is disposed therebetween. In some embodiments, the contour member 225 can be fixedly coupled to the sequestration portion 220 via an adhesive, ultrasonic welding, and/or any other suitable coupling method. In some embodiments, the contour member 225, the sequestration portion 220, and the flow controller 240 can collectively form a substantially fluid tight and/or hermetic seal that isolates the sequestration portion 220 from a volume outside of the sequestration portion 220.

As shown, a cover 235 is configured to be disposed about the contour member 225 such that the cover 235 and the sequestration portion 220 of the housing 210 enclose and/or house the contour member 225 and the flow controller 240. In some embodiments, the cover 235 can be coupled to the contour member 225 and/or the sequestration portion 220 via an adhesive, ultrasonic welding, one or more mechanical fasteners, a friction fit, a snap fit, a threaded coupling, and/or any other suitable manner of coupling. In some embodiments, the cover 235 can define an opening, window, slot, etc. configured to allow visualization of at least a portion of the sequestration chamber 230. While the contour member 225 and the cover 235 are described above as being separate pieces and/or components, in other embodiments, the contour member 225 can be integrated and/or monolithically formed with the cover 235.

The contour member 225 includes and/or forms a second contoured surface 226. The arrangement of the contour member 225 and the sequestration portion 220 of the housing 210 can be such that at least a portion of the first contoured surface 221 is aligned with and/or opposite a corresponding portion of the second contoured surface 226 of the contour member 225 (see e.g., FIG. 8). As such, a space, volume, opening, void, chamber, and/or the like defined between the first contoured surface 221 and the second contoured surface 226 forms and/or defines the sequestration chamber 230. Moreover, the flow controller 240 is disposed between the first contoured surface 221 and the second contoured surface 226 and can be configured to transition between a first state and a second state in response to a negative pressure differential and/or suction force applied to at least a portion of the sequestration chamber 230, as described in further detail herein.

The ports 217 and 218 of the housing 210 can be any suitable shape, size, and/or configuration. As described above, the first port 217 is in fluid communication with the sequestration chamber 230 and can selectively establish fluid communication between the sequestration chamber 230 and the fluid flow path 215 and/or the inlet 213. More specifically, the first port 217 is in fluid communication with a first portion of the sequestration chamber 230 defined between the second contoured surface 226 and a first side of the flow controller 240. As described in further detail herein, the first port 217 can be configured to provide and/or transfer a flow of bodily fluid from the inlet 213 and the fluid flow path 215 and into the first portion of the sequestration chamber 230 defined between the second contoured surface 226 and the first side of the flow controller 240 in response to the flow controller 240 transitioning from a first state to a second state.

The second port 218 is in fluid communication with the sequestration chamber 230 and can selectively establish fluid communication between the sequestration chamber 230 and the fluid flow path 216 and/or the outlet 214. More specifically, the second port 218 is in fluid communication with a second portion of the sequestration chamber 230 defined between the first contoured surface 221 and a second side of the flow controller 240 (e.g., opposite the first side). As described in further detail herein, the second port 218 can be configured to expose the second portion of the sequestration chamber 230 defined between the first contoured surface 221 and the second side of the flow controller 240 to a negative pressure differential and/or suction force resulting from the fluid collection device (e.g., an evacuated container, a culture bottle, a syringe, and/or the like) being fluidically coupled to the outlet 214. In turn, the negative pressure differential and/or suction force can be operable to transition the flow controller 240 from its first state to its second state. In some instances, it may be desirable to modulate and/or control a magnitude of the negative pressure differential. As such, the second port 218 can include and/or can be coupled to a restrictor 219. The restrictor 219 can be configured to limit and/or restrict a flow of fluid (e.g., air or gas) between the second portion of the sequestration chamber 230 and the fluid flow path 216, thereby modulating and/or controlling a magnitude of a pressure differential and/or suction force applied on or experienced by the flow controller 240, as described in further detail herein.

The flow controller 240 is disposed within the housing 210 between the sequestration portion 220 and the contour member 225 (e.g., within the sequestration chamber 230). The flow controller 240 can be any suitable shape, size, and/or configuration. Similarly, the flow controller 240 can be formed of any suitable material (e.g., any suitable biocompatible material such as those described herein and/or any other suitable material). For example, the flow controller 240 can be a fluid impermeable bladder, membrane, diaphragm, and/or the like configured to be transitioned from a first state and/or configuration to a second state and/or configuration. In some embodiments, the flow controller 240 (e.g., bladder) can include any number of relatively thin and flexible portions configured to deform in response to a pressure differential across the flow controller 240. For example, in some embodiments, the flow controller 240 can be formed of or from any suitable medical-grade elastomer and/or any of the biocompatible materials described above. In some embodiments, the flow controller 240 can have a durometer between about 5 Shore A and about 70 Shore A, between about 10 Shore A and about 60 Shore A, between about 20 Shore A and about 50 Shore A, between about 30 Shore A and about 40 Shore A, and/or any other suitable durometer. In some embodiments, the flow controller 240 can be formed of or from silicone having a durometer between about 20 Shore A and about 50 Shore A. More particularly, in some such embodiments, the flow controller 240 can be formed of or from silicone having a durometer of about 30 Shore A. In some embodiments, the flow controller 240 can include relatively thin and flexible portions having a thickness between about 0.001" and about 0.1". In other embodiments, the relatively thin and flexible portions can have a thickness that is less than 0.001" or greater than 0.1".

In some embodiments, the flow controller 240 can have a size and/or shape configured to facilitate, encourage, and/or otherwise result in fluid flow with a desired set of flow characteristics. Similarly, the flow controller 240 can be formed of or from a material having one or more material properties and/or one or more surface finishes configured to facilitate, encourage, and/or otherwise result in fluid flow with the desired set of flow characteristics. As described in further detail herein, the set of flow characteristics can be and/or can include a relatively even or smooth fluid flow, a substantially laminar fluid flow and/or a fluid flow with relatively low turbulence, a fluid flow with a substantially uniform front, a fluid flow that does not readily mix with other fluids (e.g., a flow of bodily fluid that does not mix with a flow or volume of air), and/or the like.

In the embodiment shown in FIG. 2-11, the flow controller 240 is a bladder (or diaphragm) formed of or from silicone having a durometer of about 30 Shore A. The flow controller 240 (e.g., bladder) includes a first deformable portion 241, a second deformable portion 242, and a third deformable portion 243. In addition, the flow controller 240 defines an opening 244. As shown, for example, in FIG. 8, the flow controller 240 can be positioned within the sequestration portion 220 of the housing 210 such that the first port 217 extends through the opening 244. In some embodiments, the arrangement of the flow controller 240 is such that a surface of the flow controller 240 defining the opening 244 forms a substantially fluid tight seal with a portion of the inner surface of the sequestration portion 220 of the housing 210 (e.g., the portion defining and/or forming the first port 217). Moreover, the flow controller 240 can include one or more portions configured to form one or more seals with and/or between the flow controller 240 and each of the contoured surfaces 221 and 226, as described in further detail herein.

The deformable portions 241, 242, and 243 of the flow controller 240 can be relatively thin and flexible portions configured to deform in response to a pressure differential between the first side of the flow controller 240 and the second side of the flow controller 240. More particularly, the deformable portions 241, 242, and 243 can each have a thickness of about 0.005". As shown, for example, in FIGS. 8 and 10, the deformable portions 241, 242, and 243 of the flow controller 240 correspond to and/or have substantially the same general shape as at least a portion of the contoured surfaces 221 and/or 226. As such, the deformable portions 241, 242, and 243 and the corresponding portion of the contoured surfaces 221 and/or 226 can collectively form and/or define one or more channels or the like, which in turn, can receive the initial volume of bodily fluid, as described in further detail herein.

As described above, the flow controller 240 is configured to transition between a first state and a second state. For example, when the flow controller 240 is in its first state, the deformable portions 241, 242, and 243 are disposed adjacent to and/or substantially in contact with the second contoured surface 226, as shown in FIG. 8. More specifically, the first deformable portion 241 can be disposed adjacent to and/or substantially in contact with a first recess 227 formed by the second contoured surface 226, the second deformable portion 242 can be disposed adjacent to and/or substantially in contact with a second recess 228 formed by the second contoured surface 226, and the third deformable portion 243 can be disposed adjacent to and/or substantially in contact with a third recess 229 formed by the second contoured surface 226.

As such, the first portion of the sequestration chamber 230 (e.g., the portion defined between the second contoured surface 226 and the first surface of the flow controller 240) can have a relatively small and/or relatively negligible volume. In contrast, when the flow controller 240 is transitioned from its first state to its second state (e.g., in response to a negative pressure applied and/or transmitted via the second port 218), at least the deformable portions 241, 242, and 243 are disposed adjacent to and/or substantially in contact with the first contoured surface 221. More specifically, the first deformable portion 241 can be disposed adjacent to and/or substantially in contact with a first recess 222 formed by the first contoured surface 221, the second deformable portion 242 can be disposed adjacent to and/or substantially in contact with a second recess 223 formed by the first contoured surface 221, and the third deformable portion 243 can be disposed adjacent to and/or substantially in contact with, for example, a non-recessed portion of the first contoured surface 221.

Accordingly, a volume of the first portion of the sequestration chamber 230 is larger when the flow controller 240 is in its second state than when the flow controller is in its first state. In other words, the deformable portions 241, 242, and 243 and the second contoured surface 226 can define one or more channels (e.g., the sequestration chamber 230) configured to receive the initial volume of bodily fluid. In some instances, the increase in the volume of the first portion of the sequestration chamber 230 can result in a negative pressure or vacuum therein that can be operable to draw the initial volume of bodily fluid into the sequestration chamber 230, as described in further detail herein. Moreover, in some embodiments, the arrangement of deformable portions 241, 242, and/or 243 can be such that a volume of air drawn into the sequestration chamber 230 immediately before the flow of bodily fluid can flow into and/or be disposed in a portion of the sequestration chamber 230 corresponding to the first deformable portion 241 and/or the second deformable portion 242.

While the flow controller 240 is particularly described above with reference to FIGS. 6-11, in other embodiments, the flow controller 240 and/or the sequestration chamber 230 can have any suitable configuration and/or arrangement. For example, in some embodiments, the contoured surfaces 221 and/or 226 can include more or fewer recesses (e.g., the recesses 222 and 223 and the recesses 227, 228, and 229, respectively). In other embodiments, a depth of one or more recesses can be modified. Similarly, the flow controller 240 can be modified in any suitable manner to substantially correspond to a shape and/or configuration of the contoured surfaces 221 and/or 226. In some embodiments, such modifications can, for example, modify one or more characteristics associated with a flow of a gas (e.g., air) and/or fluid (e.g., bodily fluid), one or more characteristics associated with the manner or rate at which the flow controller 240 transitions, and/or the like, as described in further detail herein.

While the flow controller 240 is described as being a bladder or the like including a number of deformable portions, in other embodiments, a flow controller can be arranged and/or configured as, for example, a bellows, a flexible pouch, an expandable bag, an expandable chamber, a plunger (e.g., similar to a syringe), and/or any other suitable reconfigurable container or the like. In addition, the sequestration chamber 230 at least partially formed by the flow controller 240 can have any suitable shape, size, and/or configuration.

The actuator 250 of the control device 200 can be any suitable shape, size, and/or configuration. At least a portion of the actuator 250 is disposed within the actuator portion 212 of the housing 210 and is configured to be transitioned between a first state, configuration, and/or position and a second state, configuration, and/or position. In the embodiment shown in FIGS. 2-11, the actuator 250 is configured as an actuator rod or plunger configured to be moved relative to the actuator portion 212 of the housing 210. The actuator 250 includes an end portion 251 disposed outside of the housing 210 and configured to be engaged by a user to transition the actuator 250 between its first state and its second state. As shown in FIGS. 6-11, a portion of the actuator 250 includes and/or is coupled to a set of seals 255. The seals 255 can be, for example, o-rings, elastomeric over-molds, proud or raised dimensions or fittings, and/or the like. The arrangement of the actuator 250 and the actuator portion 212 of the housing 210 can be such that an inner portion of the seals 255 forms a fluid tight seal with a surface of the actuator 250 and an outer portion of the seals 255 forms a fluid tight seal with an inner surface of the actuator portion 212 of the body 210. In other words, the seals 255 form one or more fluid tight seals between the actuator 250 and the inner surface of the actuator portion 212. As shown in 7-11, the actuator 250 includes and/or is coupled to four seals 255 which can be distributed along the actuator 250 to selectively form and/or define one or more flow paths therebetween. Moreover, the actuator 250 defines a flow channel 252 defined between a pair of seals 255 which can aid and/or facilitate the fluid communication between the fluid flow paths 215 and 216 when the actuator 250 is transitioned to its second state, as described in further detail herein. While the actuator 250 is described above as including four seals 255, in other embodiments, the actuator 250 can include fewer than four seals 255 or more than four seals 255.

In some embodiments, the actuator portion 212 of the housing 210 and the actuator 250 collectively include and/or collectively form a lock. For example, as shown in FIGS. 6 and 8, the actuator portion 212 of the housing 210 can define an opening 238 and the actuator 250 can include a locking member, latch, protrusion, tab, and/or the like (referred to herein as "lock 253") configured to be disposed, at least partially, within the opening 238. In some embodiments, the lock 253 can be arranged and/or disposed in the opening 238 and can limit and/or substantially prevent the actuator 250 from being removed from the housing 210. In some embodiments, the lock 253 can be transitioned between a locked state, in which the lock 253 limits and/or substantially prevents the actuator 250 from being moved relative to the housing 210, and an unlocked state, in which the actuator 250 can be moved, for example, between its first state and/or position and its second state and/or position. In some instances, such an arrangement may limit and/or substantially prevent the actuator 250 from being actuated, for example, prior to transferring the initial volume of bodily fluid in the sequestration chamber 230. In other embodiments, the lock 253 can transition from the unlocked state to a locked state, for example, after transferring the initial volume of bodily fluid into the sequestration chamber 230.

As shown in FIGS. 7 and 8, when the actuator 250 is disposed in its first state and/or position (e.g., prior to using the device 100), the fluid flow path 215 can establish fluid communication between the inlet 213 and the first port 217. More particularly, the actuator 250 can be in a position relative to the housing 210 such that each of the seals 255 is disposed on a side of the inlet 213 opposite to a side of the inlet 213 associated with the first port 217. In other words, the actuator 250 and/or the seals 255 do not obstruct and/or occlude the fluid flow path 215 when the actuator 250 is in the first state and/or position, as shown in FIGS. 7 and 8. As such, when the actuator 250 is in the first state and/or position, a volume of bodily fluid (e.g., an initial volume) can flow from the inlet 213, through the fluid flow path 215 and the first port 217, and into the sequestration chamber 230, as described in further detail herein.

Figure 9:
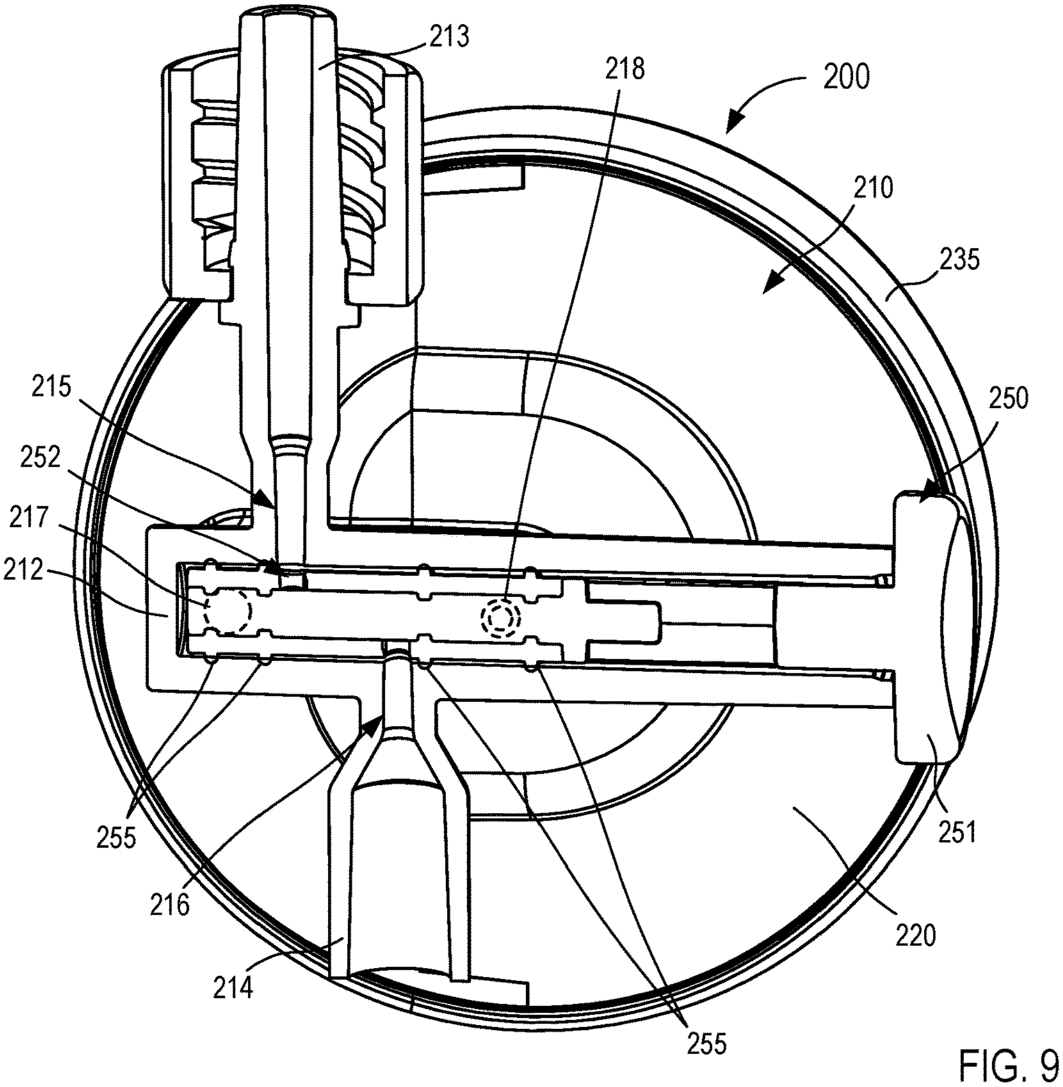
FIGS. 9 and 10 are each a cross-sectional view of the fluid control device of FIG. 2 taken along the line 7-7 in FIG. 4 and the line 8-8 in FIG. 5, respectively, shown in a second state.
Figure 10:
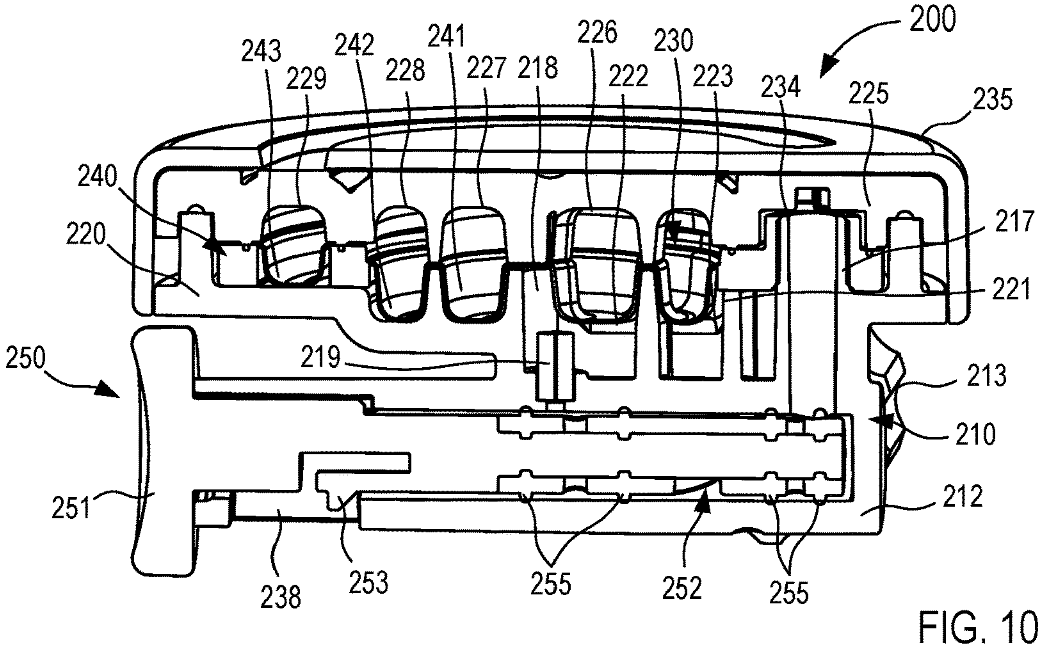
Figure 11:
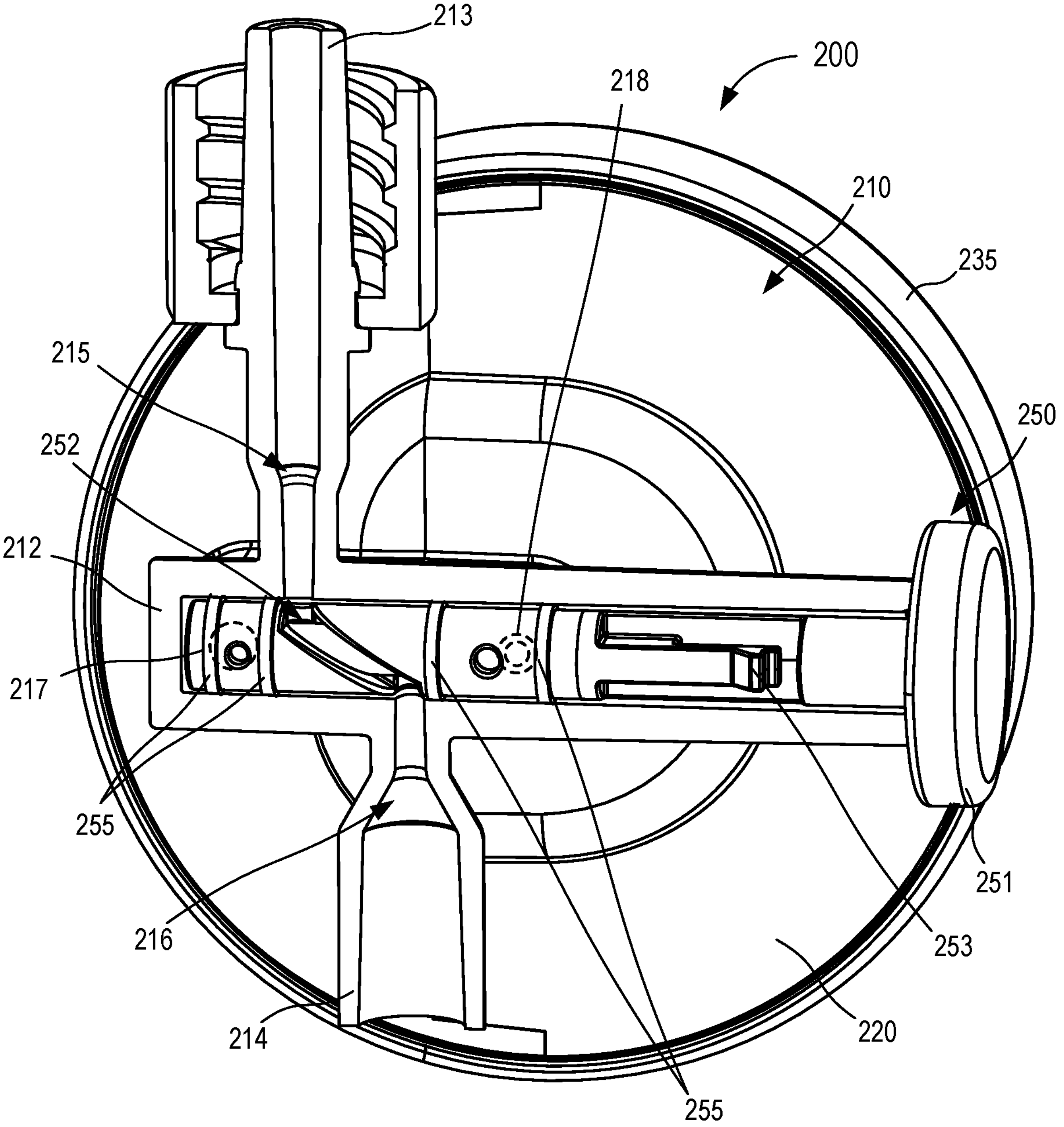
FIG. 11 is a partial cross-sectional view of the fluid control device of FIG. 2 taken along the line 8-8 in FIG. 5, shown in the second state.
Figure 12:
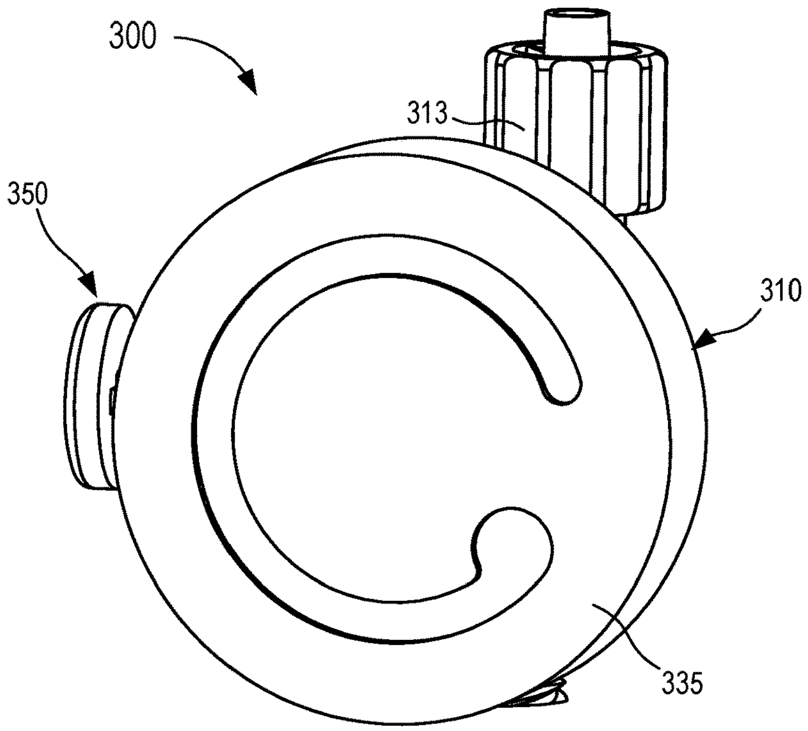
FIGS. 12 and 13 are a front perspective view and a rear perspective view, respectively, of a fluid control device according to an embodiment.
Figure 13:
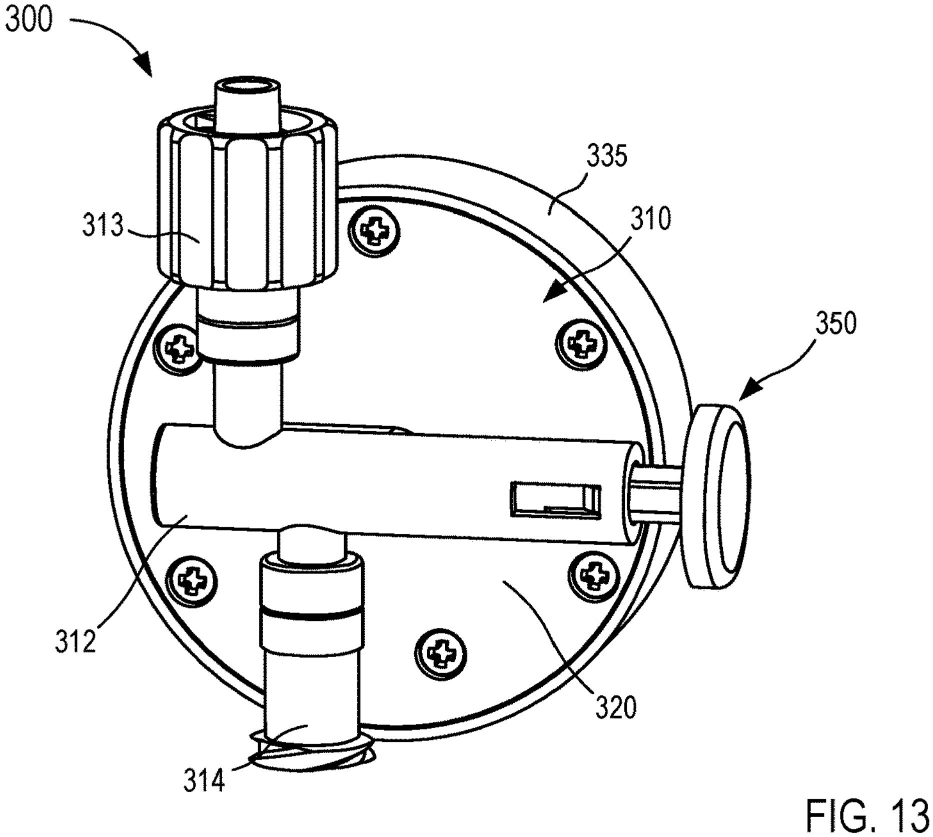
Figure 14:
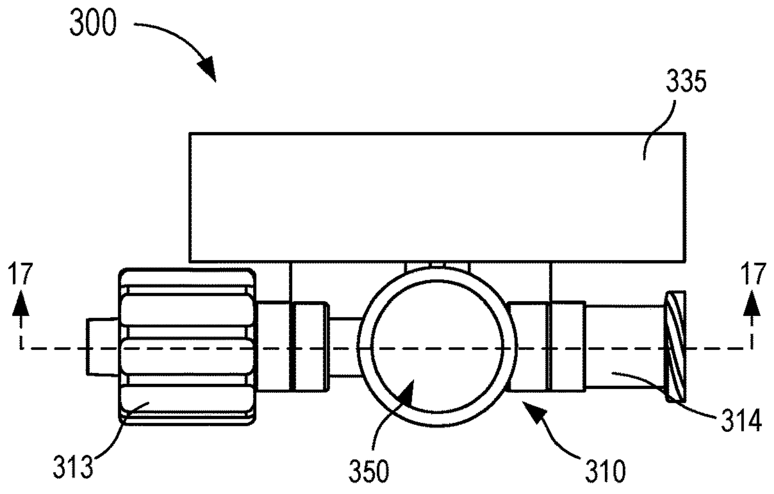
FIGS. 14 and 15 are a side view and a top view, respectively, of the fluid control device of FIG. 12.
Figure 15:
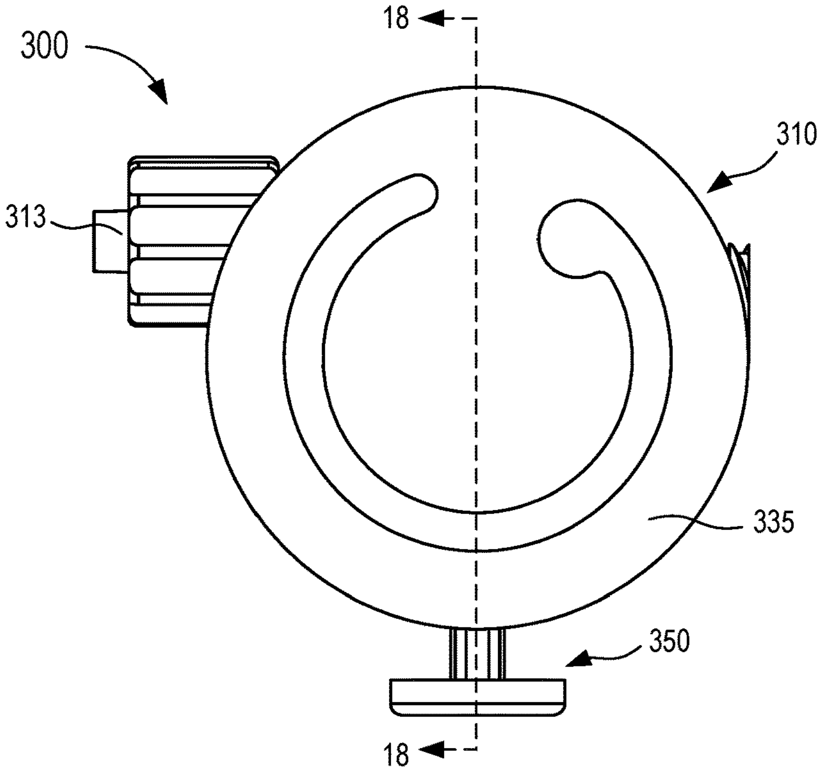

As shown in FIGS. 9-11, a force can be exerted on the end portion 251 of the actuator 250 to place the actuator 250 in its second state and/or position. When in the second state and/or position, the inlet 213 and the outlet 214 are placed in fluid communication via at least a portion of the fluid flow paths 215 and 216 and/or the flow channel 252. As shown in FIGS. 9 and 11, the actuator 250 can be position such that the inlet 213 and the outlet 214 are each disposed between the same pair of seals 255, thereby allowing a flow of bodily fluid therethrough. In addition, the flow channel 252 defined by the actuator 250 assists and/or facilitates the flow of bodily fluid (see e.g., FIG. 11). For example, in some embodiments, the flow channel 252 can establish fluid communication between a portion of the fluid flow path 215 defined by the inlet 213 and a portion of the fluid flow path 216 defined by the outlet 214. Moreover, the arrangement of the seals 255 is such that the first port 217 and the second port 218 are each sequestered and/or isolated from each of the inlet 213 and the outlet 214. As such, placing the actuator 250 in the second state and/or position can (1) sequester and/or isolate the sequestration chamber 230 and any volume of bodily fluid disposed therein and (2) establish fluid communication between the inlet 213 and the outlet 214, thereby allowing a volume of bodily fluid to flow through the device 200 and into a fluid collection device (not shown) fluidically coupled to the outlet 214.

In some embodiments, the set of seals 255 can be configured to sequester, isolate, and/or seal one or more portions of the device 200 prior to establishing fluid communication between other portions of the device 200. For example, in some embodiments, the actuator 250 can be in a first positon relative to the actuator portion 212 of the housing 210 when in the first state, as described above. In such instances, actuating the actuator 250 (e.g., exerting a force of the end portion 251 of the actuator 250) can include moving the actuator 250 from the first position relative to the actuator portion 212 to a second position relative to the actuator portion 212, in which (1) a first seal 255 is disposed between the first port 217 and the inlet 213 and/or a lumen thereof, (2) the inlet 213 and/or the lumen thereof is disposed between the first seal 255 and a second seal 255, (3) the outlet 214 and/or a lumen thereof is disposed between the second seal 255 and a third seal 255, and (4) the second port 218 is disposed between the third seal 255 and a fourth seal 255. In this manner, the inlet 213 is sequestered from the first port 217, the outlet 214 is sequestered from the second port 218, and fluid communication has not yet been established between the inlet 213 and the outlet 214 (e.g., the inlet 213 is sequestered from the outlet 214).

In some instances, actuating the actuator 250 can further include moving the actuator 250 from the second position relative to the actuator portion 212 to a third position relative to the actuator portion 212, in which the actuator 250 is in the second state. As such, the second seal 255 is disposed between the first port 217 and the inlet 213 and/or the lumen thereof, each of the inlet 213 and the outlet 214 (and/or the lumens thereof) is disposed between the second seal 255 and the third seal 255, and the second port 218 is disposed between the third seal 255 and the fourth seal 255. Thus, each of the first port 217 and the second port 218 are sequestered from the inlet 213 and the outlet 214 (and/or the lumens thereof), and fluid communication is established (e.g., via the flow channel 252) between the inlet 213 and the outlet (and/or the lumens thereof).

While the actuator 250, in this example, is described as being moved between the first, second, and third positions relative to the actuator portion 212, it should be understood that transitioning the actuator 250 from the first state to the second state can include moving the actuator 250 in a substantially continuous manner from the first position relative to the actuator portion 212, through the second position relative to the actuator portion 212, and to the third position relative to the actuator portion 212. In other embodiments, the actuator 250 can be actuated, moved, and/or transitioned, in any number of discrete steps. For example, in some instances, the actuator 250 can be transitioned a first predetermined amount to move the actuator 250 from the first position relative to the actuator portion 212 to the second position relative to the actuator portion 212 and can then be transitioned (e.g., in a second and/or discrete step) a second predetermined amount to move the actuator 250 from the second position relative to the actuator portion 212 to the third position relative to the actuator portion 212. While the actuator 250 is described above as including four seals 255, in other embodiments, an actuator can be functionally similar to the actuator 250 and can include fewer than four seals (e.g., one seal, two seals, or three seals) or more than four seals (e.g., five seals, six seals, seven seals, or more).

As described above, the device 200 can be used to procure a bodily fluid sample having reduced contamination (e.g., contamination from microbes such as, for example, dermally residing microbes, microbes external to the bodily fluid source, and/or the like). For example, prior to use, the device 200 can be in its first, initial, and/or storage state or operating mode, in which each of the flow controller 240 and the actuator 250 is in its respective first or initial state. With the device 200 in the first state, a user such as a doctor, physician, nurse, phlebotomist, technician, etc. can manipulate the device 200 to establish fluid communication between the inlet 213 and the bodily fluid source (e.g., a vein of a patient). Once the inlet 213 is placed in fluid communication with the bodily fluid source, the outlet 214 can be fluidically coupled to a fluid collection device (not shown in FIGS. 2-11). In the embodiment shown in FIGS. 2-11, for example, the fluid collection device can be an evacuated container, a culture bottle, a sample reservoir, a syringe, and/or any other suitable container or device configured to define or produce a negative pressure, suction force, vacuum, and/or energy potential.

When the actuator 250 is in the first position and/or configuration, the inlet 213 of the housing 210 is in fluid communication with, for example, the fluid flow path 215, which in turn, is in fluid communication with the first port 217. The outlet 214 of the of the housing 210 is in fluid communication with the fluid flow path 216, which in turn, is in fluid communication with the second port 218. More particularly, one or more of the seals 255 of the actuator 250 can be in a position relative to the actuator portion 212 of the housing 210 that (1) allows and/or establishes fluid communication between the inlet 213, the fluid flow path 215, and the first port 217 and (2) fluidically isolates the inlet 213, the fluid flow path 215, and the first port 217 from the outlet 214, the fluid flow path 216, and the second port 218, as shown in FIGS. 7 and 8. Thus, when the control device 200 is in the first state or operating mode (e.g., when the actuator 250 and the flow controller 240 are each in their first state), fluidically coupling the fluid collection device to the outlet 214 generates and/or otherwise results in a negative pressure differential and/or suction force within at least a portion of the fluid flow path 216 and, in turn, within the portion of the sequestration chamber 230 defined between a surface of the flow controller 240 (e.g., a first surface) and the first contoured surface 221 of the housing 210.

The flow controller 240 is in the first state and/or configuration prior to the fluid collection device being coupled to the outlet 214. In the embodiment shown in FIGS. 2-11, the flow controller 240 is a fluid impermeable bladder, diaphragm, membrane, and/or the like that can have a flipped, inverted, collapsed, and/or empty configuration (e.g., the first state and/or configuration) prior to coupling the fluid collection device to the outlet 214. For example, as shown in FIG. 8, the flow controller 240 can be disposed adjacent to and/or in contact with the second contoured surface 226 when the flow controller 240 is in its first state and/or configuration. Said another way, the first side of the flow controller 240 (opposite the second side) can be disposed adjacent to and/or can be in contact with the second contoured surface 226.

As described above, the flow controller 240 is configured to transition from its first state and/or configuration to its second state and/or configuration in response to the negative pressure differential and/or suction force generated within the portion of the sequestration chamber 230 defined between the flow controller 240 and the first contoured surface 221. For example, the flow controller 240 can be configured to transition, move, "flip", and/or otherwise reconfigure to its second state and/or configuration in which the flow controller 240 and/or the second side of the flow controller 240 (opposite the first side) is disposed adjacent to and/or in contact with the first contoured surface 221, as shown in FIG. 10. Said another way, the negative pressure differential and/or suction force draws, pulls, and/or otherwise moves at least a portion of the flow controller 240 toward the first contoured surface 221 and away from the second contoured surface 226. Moreover, the control device 200 is placed in its second state and/or configuration when the actuator 250 is in its first state and the flow controller 240 is in its second state.

The transitioning of the flow controller 240 results in an increase in an inner volume of the portion of the sequestration chamber 230 defined between a surface of the flow controller 240 (e.g., the first side of the flow controller 240) and the second contoured surface 226. The increase in the inner volume can, in turn, result in a negative pressure differential between the portion of the sequestration chamber 230 (defined at least in part by the flow controller 240) and, for example, the inlet 213 that is operable in drawing at least a portion of an initial flow, amount, or volume of bodily fluid from the inlet 213, through the fluid flow path 215 and the first port 217, and into the portion of the sequestration chamber 230. In some instances, the initial volume and/or flow of bodily fluid can be transferred into the sequestration chamber 230 until, for example, the flow controller 240 is fully expanded, flipped, and/or transitioned, until the negative pressure differential is reduced and/or equalized, and/or until a desired volume of bodily fluid is disposed within the portion of the sequestration chamber 230.

In some instances, it may be desirable to modulate and/or control a manner in which the flow controller 240 is transitioned and/or a magnitude of the negative pressure differential and/or suction force generated within the sequestration chamber 230 on one or both sides of the flow controller 240. In the embodiment shown in FIGS. 2-11, for example, the second port 218 defines, includes, receives, and/or is otherwise coupled to the restrictor 219 that establishes fluid communication between the fluid flow path 216 and the portion of the sequestration chamber 230 defined between the flow controller 240 and the first contoured surface 221.

In some embodiments, the restrictor 219 can define a lumen or flow path having a relatively small diameter (e.g., relative to a diameter of at least a portion of the fluid flow path 216). For example, in some embodiments, the restrictor 219 can have a diameter of about 0.0005", about 0.001", about 0.003", about 0.005", about 0.01", about 0.1", about 0.5", or more. In other embodiments, the restrictor 219 can have a diameter less than 0.0005" or greater than 0.5". In some embodiments, the restrictor 219 can have a predetermined and/or desired length of about 0.01", about 0.05", about 0.1", about 0.15", about 0.2", about 0.5", or more. In other embodiments, the restrictor 219 can have a predetermined and/or desired length that is less than 0.01" or more than about 0.5". Moreover, in some embodiments, the restrictor 219 can have any suitable combination of diameter and length to allow for and/or to provide a desired fluid (e.g., air) flow characteristic through at least a portion of the control device 200. While the restrictor 219 is described above as defining a relatively small lumen and/or flow path, in other embodiments, a restrictor can have any suitable shape, size, and/or configuration. For example, in some embodiments, a restrictor can be a porous material, a semi-permeable member or membrane, a mechanical valve, float, and/or limiter, and/or any other suitable member or device configured to modulate a pressure differential across at least a portion thereof.

In the embodiment shown in FIGS. 2-11, the relatively small diameter of the restrictor 219 results in a lower magnitude of negative pressure being applied through and/or within the portion of the sequestration chamber 230 than would otherwise be applied with a restrictor have a larger diameter or if the second port 218 did not include or receive a restrictor 219. For example, in some embodiments, a fluid collection device and/or other suitable negative pressure source may define and/or produce a negative pressure differential having a magnitude (e.g., a negative magnitude) of about 0.5 pounds per square inch (PSI), about 1.0 PSI, about 2.0 PSI, about 3.0 PSI, about 4.0 PSI, about 5.0 PSI, about 10.0 PSI, about 12.5 PSI, or about 14.7 PSI (at or substantially at atmospheric pressure at about sea level). In some embodiments, a fluid collection device such as an evacuated container or the like can have a predetermined negative pressure of about 12.0 PSI. Accordingly, by controlling the diameter and/or length of the restrictor 219, the amount of negative pressure to which the portion of the sequestration chamber 230 is exposed and/or the rate at which the negative pressure is applied can be controlled, reduced, and/or otherwise modulated. In some instances, the use of the restrictor 219 can result in a delay or ramp up of the negative pressure exerted on or in the portion of the sequestration chamber 230.

Although the pressure modulation is described above as being based on a diameter of the restrictor 219 (i.e., a single restricted flow path), it should be understood that this is presented by way of example only and not limitation. Other means of modulating the magnitude of negative pressure to which the portion of the sequestration chamber 230 is exposed can include, for example, a porous material, a valve, a membrane, a diaphragm, a specific restriction, a vent, a deformable member or flow path, and/or any other suitable means. In other embodiments, a control device can include any suitable number of restricted flow paths, each of which can have substantially the same diameter or can have varied diameters. For example, in some embodiments, a control device can include up to 100 restricted flow paths or more. In such embodiments, each of the restricted flow paths can have a diameter of between about 0.0005" and about 0.1", between about 0.0005" and about 0.05", or between about 0.0005" and about 0.01". In some embodiments, multiple restricted flow paths can be configured to selectively provide a flow path between the outlet 214 and the portion of the sequestration chamber 230 that exposes the portion of the sequestration chamber 230 to the negative pressure differential.

In some embodiments, modulating and/or controlling a magnitude of the pressure to which the portion of the sequestration chamber 230 is exposed can, in turn, modulate a rate at which one or more volumes of the sequestration chamber 230 are increased. In some instances, modulating the rate of volume increase (and thus, suction force) can modulate and/or limit a magnitude of pressure exerted on the bodily fluid and/or within a vein of a patient. In some instances, such pressure modulation can reduce, for example, hemolysis of a blood sample and/or a likelihood of collapsing a vein. In some instances, the ability to modulate and/or control an amount or magnitude of negative pressure or suction can allow the control device 200 to be used across a large spectrum of patients that may have physiological challenges whereby negative pressure is often needed to facilitate collection of bodily fluid such as, for example, blood (i.e. pressure differential between atmospheric pressure and a patient's vascular pressure is not sufficient to facilitate consistent and sufficiently forceful flow) but not so much pressure that a rapid force flattens, collapses, caves-in, and/or otherwise inhibits patency and ability to collect blood.

In some embodiments, the shape, size, and/or arrangement of the sequestration chamber 230 and/or the flow controller 240, the magnitude of the negative pressure differential or suction force, and/or the way in which the negative pressure differential or suction force is exerted can dictate and/or control a rate and/or manner in which the flow controller 240 is transitioned from the first state to the second state. In some instances, controlling the rate, order, and/or manner in which the flow controller 240 is transitioned can result in one or more desired flow characteristics associated with a flow of air, gas, and/or bodily fluid into and/or through at least a portion of the sequestration chamber 230.

For example, the arrangement included in this embodiment can be such that a transitioning and/or flipping of the third deformable portion 243 of the flow controller 240 is completed prior to completion of the transitioning and/or flipping of the first and second deformable portions 241 and 242. In some instances, this arrangement can be such that a portion of the sequestration chamber 230 collectively defined by the first deformable portion 241 and the first recess 227 of the second contoured surface 226 (e.g., a first volume of the sequestration chamber 230) receives at least a portion of a volume of air that was within the fluid flow path between the bodily fluid source and the sequestration chamber 230 prior to the fluid flow path receiving and/or being filled with bodily fluid. Similarly, a portion of the sequestration chamber 230 collectively defined by the second deformable portion 242 and the second recess 228 of the second contoured surface 226 (e.g., a second volume of the sequestration chamber 230) can receive at least a portion of the volume of air that was within the fluid flow path. In other words, the transitioning of the flow controller 240 can vent, evacuate, and/or purge air or gas from the fluid flow path between the bodily fluid source and the sequestration chamber 230, which can then be collected, stored, and/or contained within the first and second volumes of the sequestration chamber 230. On the other hand, a portion of the sequestration chamber 230 collectively defined by the third deformable portion 243 and the third recess 229 of the second contoured surface 226 (e.g., a third volume of the sequestration chamber 230) can receive the initial volume of bodily fluid that flows through the fluid flow path between the bodily fluid source and the sequestration chamber 230 after the air or gas is collected in the first and/or second volumes of the sequestration chamber 230.

In some instances, such an arrangement and/or order of the deformable portions 241, 242, and/or 243 transitioning can result in an even flow of the initial volume of bodily fluid into, for example, the third volume of the sequestration chamber 230. More particularly, the third deformable portion 243 is configured to complete or substantially complete the transition and/or flip from its first state and/or position prior to a complete or a substantially complete transition and/or flip of the first and/or second deformable portions 241 and/or 242, respectively, which in turn, can allow the bodily fluid to flow into and/or through at least a portion of the third deformable portion 243 with a substantially uniform front. In this manner, the third deformable portion 243 can be in the second state, configuration, and/or position prior to the flow of bodily fluid entering the sequestration chamber 230. Thus, the third volume of the sequestration chamber 230 can have and/or can define a relatively consistent and/or uniform cross-sectional shape and/or area as the flow of bodily fluid enters the sequestration chamber 230, which in turn, can limit wicking of a portion of the bodily fluid flow, inconsistent local flow rates of the bodily fluid flow, and/or an otherwise uneven filling of the third volume of the sequestration chamber 230.

As shown in FIGS. 8 and 10, the first contoured surface 221 includes the recesses 222 and 223 that are each deeper than a portion of the first contoured surface 221 aligned and/or otherwise associated with the third deformable portion 243 of the flow controller 240. Said another way, a distance between the first recess 222 and the second recess 223 of the first contoured surface 221 and the first recess 227 and the second recess 228, respectively, of the second contoured surface 226 is greater than a distance between the portion of the first contoured surface 221 and the third recess 229 of the second contoured surface 226. Accordingly, a distance traveled when the first and second deformable portions 241 and 242 transition and/or flip is greater than a distance traveled when the third deformable portion 243 transitions and/or flips. Furthermore, a width of the first and second deformable portions 241 and 242 can be similar to or less than a width of the third deformable portion 243. In some instances, such an arrangement can allow the third deformable portion 243 to complete or substantially complete its transition and/or flip prior to each of the first and second deformable portions 241 and 242, respectively, completing or substantially completing its transition and/or flip. In other embodiments, a distance traveled and/or a width of one or more of the deformable portions 241, 242, and/or 243 can be modified (increased or decreased) to modify and/or change a rate, order, and/or sequence associated with the deformable portions 241, 242, and/or 243 transitioning and/or flipping from the first state to the second state.

In some embodiments, including fewer deformable portions or including more deformable portions can, for example, modify a relative stiffness of or associated with each deformable portion and/or can otherwise control a rate and/or manner in which each of the deformable portions transitions or flips, which in turn, can control a rate and/or manner in which fluid (e.g., air and/or bodily fluid) flows into the sequestration chamber 230. For example, in some embodiments, increasing a number of deformable portions can result in a decrease in surface area on which the negative pressure is exerted, which in turn, can increase a pressure differential sufficient to transition and/or flip the deformable portions. While the deformable portions 241, 242, and 243 are shown in FIGS. 8 and 10 as having substantially the same thickness, in other embodiments, at least one deformable portion can have a thickness that is different from a thickness of the other deformable portions (e.g., the deformable portion 241 can have a different thickness than the thicknesses of the deformable portion 242 and/or the deformable portion 243 (or vice versa or in other combinations). In some instances, increasing a thickness of a deformable portion relative to a thickness of the other deformable portions can increase a stiffness of that deformable portion relative to a stiffness of the other deformable portions. In some such instances, the increase in the stiffness of the thicker deformable portion can, in turn, result in the other deformable portions (e.g., the thinner deformable portions) transitioning and/or flipping prior to the thicker/stiffer deformable portion transitioning and/or flipping. In some embodiments, a deformable portion can have a varied thickness along at least a portion of the deformable portion.

In some embodiments, a size, shape, material property, surface finish, etc. of the flow controller 240 and/or the deformable portions 241, 242, and/or 243 can also facilitate, encourage, and/or otherwise result in fluid flow with the substantially uniform front. For example, the third volume of the sequestration chamber 230 (collectively defined by the third deformable portion 243 and the third recess 229 of the second contoured surface 226) can have a size, shape, diameter, perimeter, and/or cross-sectional area that can limit and/or substantially prevent mixing of air with the bodily fluid flow (e.g., the front of the flow) due, at least in part, to a surface tension between the flow of bodily fluid and each of the third deformable portion 243 and the third recess 229 of the second contoured surface 226. In some embodiments, for example, the third volume of the sequestration chamber 230 can have a cross-sectional area between about 0.0001 square inch ($in^2$), and about 0.16 $in^2$, between about 0.001 $in^2$ and about 0.08 $in^2$, between about 0.006 $in^2$ and about 0.06 $in^2$, or between about 0.025 $in^2$ and about 0.04 $in^2$. In other embodiments, the third volume of the sequestration chamber 230 can have a cross-sectional area that is less than 0.0001 in 2 or greater than 0.16 $in^2$.

In some embodiments, the flow controller 240 and/or the contoured member 225 (or at least the second contoured surface 226 thereof) can be formed of or from a material having one or more material properties and/or one or more surface finishes configured to facilitate, encourage, and/or otherwise result in fluid flow with the desired set of flow characteristics. In other embodiments, the flow controller 240 and/or the second contoured surface 226 can have a coating configured to result in the desired set of flow characteristics. For example, in some embodiments, the flow controller 240 and/or the second contoured surface 226 can be formed of and/or can otherwise include a coating of a hydrophobic material or a hydrophilic material. Moreover, the flow controller 240 and at least a portion of the contoured member 225 (or at least the second contoured surface 226 thereof) can be formed of or from the same material and/or can include the same coating or can be formed of or from different materials and/or can include different coatings. Similarly, the flow controller 240 and/or the second contoured surface 226 can include any suitable surface finish which can be substantially the same or different. In some instances, a non-exhaustive list of a desired set of flow characteristics can be and/or can include one or more of a relatively even or smooth fluid flow, a substantially laminar fluid flow and/or a fluid flow with relatively low turbulence, a fluid flow with a substantially uniform front, a fluid flow that does not readily mix with other fluids (e.g., a flow of bodily fluid that does not mix with a flow or volume of air), a flow with a relatively uniform velocity, and/or the like.

While certain aspects and/or features of the embodiment shown in FIGS. 2-11 are described above, along with ways in which to modify and/or "tune" the aspects and/or features, it should be understood that a flow controller and/or a sequestration chamber (or any structure forming a sequestration chamber) can have any suitable arrangement to result in desired rate, manner, and/or order of conveying the initial volume of bodily fluid into one or more portions or volumes of the sequestration chamber 230. In some embodiments, a flow controller and/or a sequestration chamber can include and/or can incorporate any suitable combination of the aspects and/or features described above. Any number of the aspects and/or features described above can be included in a device and can act in concert or can act cooperatively to result in the desired fluid flow and/or desired fluid flow characteristics through at least a portion of the sequestration chamber. Moreover, it should be understood that the aspects and/or features described above are provided by way of example only and not limitation.

Having transferred the initial volume of bodily fluid into the sequestration chamber 230, a force can be exerted on the end portion 251 of the actuator 250 to transition and/or place the actuator 250 in its second position, state, operating mode, and/or configuration, as described in above. In some instances, prior to exerting the force on the end portion 251 of the actuator 250, the actuator 250 may be transitioned from a locked configuration or state to an unlocked configuration or state. In the embodiment shown in FIGS. 2-11, the transition of the actuator 250 can be achieved by and/or can otherwise result from user interaction and/or manipulation of the actuator 250. In other embodiments, however, the transition of the actuator 250 can occur automatically in response to negative pressure and/or associated flow dynamics within the device 200, and/or enacted by or in response to an external energy source that generates one or more dynamics or states that result in the transitioning of the actuator 250.

As shown in FIGS. 9-11, the control device 200 is placed in its third state when each of the flow controller 240 and the actuator 250 is in its second state. When the actuator 250 is transitioned to its second state, position, and/or configuration, the inlet 213 and the outlet 214 are placed in fluid communication (e.g., via a portion of the fluid flow paths 215 and 216 and/or the flow channel 252) while the first port 217 and the second port 218 are sequestered, isolated, and/or otherwise not in fluid communication with the inlet 213 and/or the outlet 214. As such, the initial volume of bodily fluid is sequestered in the portion of the sequestration chamber 230 (e.g., the third volume of the sequestration chamber 230, as described above). Moreover, in some instances, contaminants such as, for example, dermally residing microbes and/or any other contaminants can be entrained and/or included in the initial volume of the bodily fluid and thus, are sequestered in the sequestration chamber 230 when the initial volume is sequestered therein. As such, the negative pressure previously exerted on or through the fluid flow path 216 and through the second port 218 is now exerted on or through the outlet 214 and the inlet 213 via, for example, at least a portion of the fluid flow paths 215 and 216 and/or the flow channel 252 of the actuator 250 (FIG. 11). In response, bodily fluid can flow from the inlet 213, through the actuator portion 212 of the housing 210, through the outlet 214, and into the fluid collection device coupled to the outlet 214. Accordingly, the device 200 can function in a manner substantially similar to that of the device 100 described in detail above with reference to FIG. 1.

FIGS. 12-21 illustrate a fluid control device 300 according to another embodiment. The fluid control device 300 (also referred to herein as "control device" or "device") can be similar in at least form and/or function to the devices 100 and/or 200 described above. For example, as described above with reference to the devices 100 and 200, in response to being placed in fluid communication with a negative pressure source (e.g., a suction or vacuum source), the device 300 can be configured to (1) withdraw bodily fluid from a bodily fluid source into the device 300, (2) divert and sequester a first portion or amount (e.g., an initial volume) of the bodily fluid in a portion of the device 300, and (3) allow a second portion or amount (e.g., a subsequent volume) of the bodily fluid to flow through the device 300—bypassing the sequestered initial volume—and into a fluid collection device fluidically coupled to the device 300. As such, contaminants or the like can be sequestered in or with the initial volume of bodily fluid, leaving the subsequent volume of bodily fluid substantially free of contaminants. In some embodiments, portions and/or aspects of the control device 300 can be similar to and/or substantially the same as portions and/or aspects of the control device 200 described above with reference to FIGS. 2-11. Accordingly, such similar portions and/or aspects may not be described in further detail herein.

The fluid control device 300 (also referred to herein as "control device" or "device") includes a housing 310, a flow controller 340, and an actuator 350. In some embodiments, the control device 300 or at least a portion of the control device 300 can be arranged in a modular configuration in which one or more portions of the housing 310 and/or the actuator 350 can be physically and fluidically coupled (e.g., by an end user) to collectively form the control device 300. Similarly, in some embodiments, the control device 300 can be packaged, shipped, and/or stored independent of a fluid collection device (e.g., a sample reservoir, syringe, etc.) and/or an inlet device (e.g., a needle, catheter, PIV, PICC, etc.), which a user can couple to the control device 300 before or during use. In other embodiments, the control device 300 need not be modular. For example, in some embodiments, the control device 300 can be assembled during manufacturing and delivered to a supplier and/or end user as an assembled device. In some embodiments, the control device 300 can include and/or can be pre-coupled (e.g., during manufacturing and/or prior to being delivered to an end user) to a fluid collection device such as any of those described above. Similarly, in some embodiments, the control device 300 can include and/or can be pre-coupled to an inlet device such as any of those described herein.

The housing 310 of the control device 300 can be any suitable shape, size, and/or configuration. The housing 310 includes an actuator portion 312 and a sequestration portion 320. The actuator portion 312 receives at least a portion of the actuator 350. The sequestration portion 320 is coupled to a cover 335 and includes, receives, houses, and/or at least partially defines a sequestration chamber 330. As described in further detail herein, the housing 310 can include and/or can define a first port 317 and a second port 318, each of which establishes fluid communication between the actuator portion 312 and the sequestration portion 320 of the housing 310 to selectively control and/or allow a flow of fluid through one or more portions of the housing 310.

As shown in FIGS. 12-16, the actuator portion 312 of the housing 310 includes an inlet 313 and an outlet 314, and defines a fluid flow path 315 (e.g., a first fluid flow path) that is configured to selectively place the inlet 313 in fluid communication with the first port 317 and a fluid flow path 316 (e.g., a second fluid flow path) that is configured to selectively place the outlet 314 in fluid communication with the second port 318. The inlet 313 of the housing 310 is configured to be placed in fluid communication with a bodily fluid source (e.g., in fluid communication with a patient via a needle, IV catheter, PICC line, etc.) to receive a flow of bodily fluid therefrom, as described in detail above. The outlet 314 is configured to be fluidically coupled to a fluid collection device such as any of those described above (e.g., a sample reservoir, a syringe, culture bottle, an intermediary bodily fluid transfer device or adapter, and/or the like). The fluid collection device can define and/or can be manipulated to define a vacuum or negative pressure that results in a negative pressure differential between desired portions of the housing 310 when the fluid collection device is coupled to the outlet 314. In addition, after an initial volume of bodily fluid has been transferred into the sequestration chamber 330, fluid communication can be established between the fluid flow paths 315 and 316 to allow a subsequent volume of bodily fluid (e.g., a bodily fluid sample) to flow through the device 300 and into the fluid collection device. Accordingly, the actuator portion 312 of the housing 310 can be substantially similar in at least form and/or function to the actuator portion 212 of the housing 210 and thus, is not described in further detail herein.

The sequestration portion 320 of the housing 310 can be any suitable shape, size, and/or configuration. As shown, for example, in FIGS. 16-18, the sequestration portion 320 includes and/or forms an inner surface, a portion of which is arranged and/or configured to form a first contoured surface 321. At least a portion of the first contoured surface 321 can form and/or define a portion of the sequestration chamber 330, as described in further detail herein. Furthermore, the first port 317 and the second port 318 are configured to form and/or extend through a portion of the first contoured surface 321 to selectively place the sequestration chamber 330 in fluid communication with the fluid flow paths 315 and 316, as described in further detail here.

Figure 16:
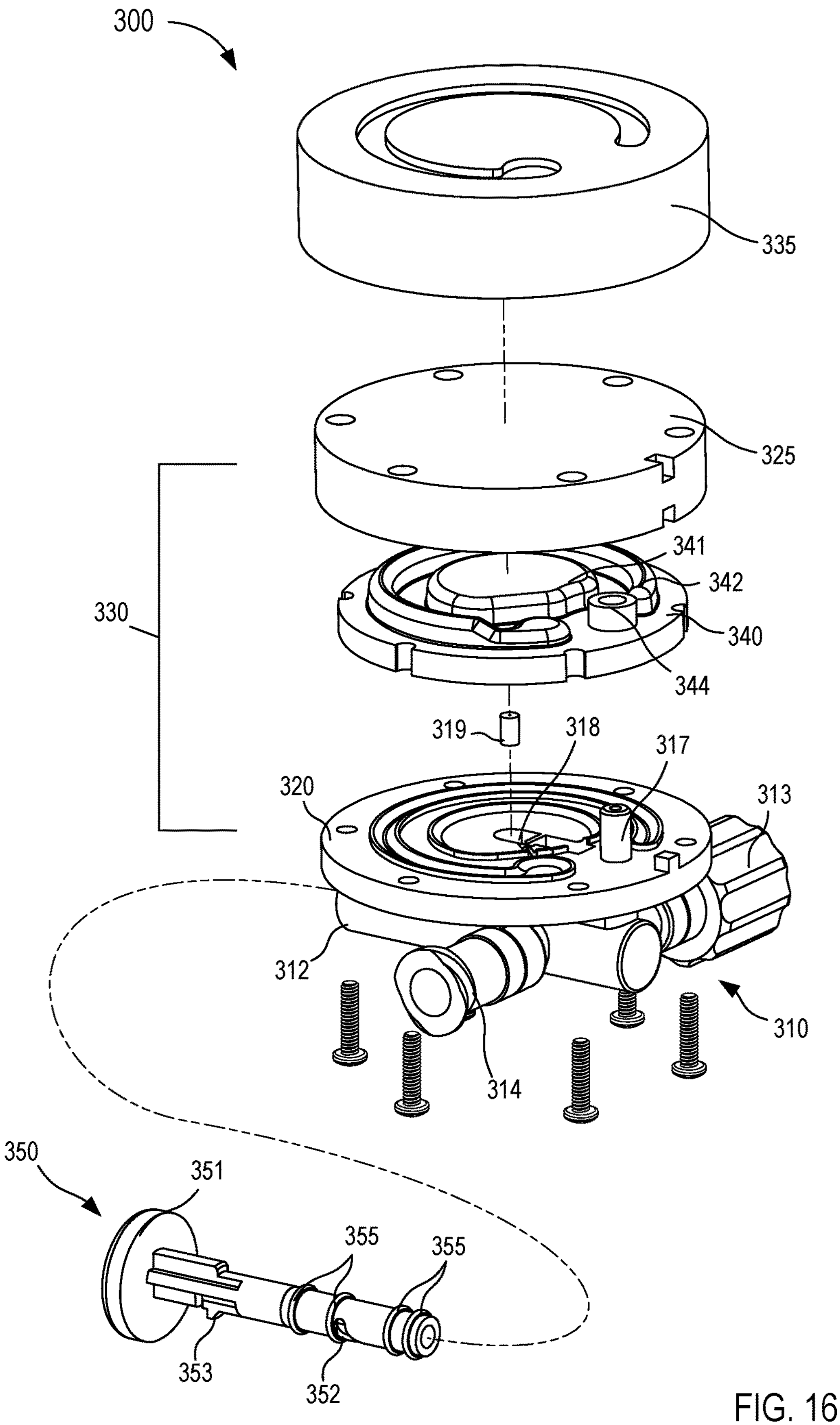
FIG. 16 is an exploded perspective view of the fluid control device of FIG. 12.
Figure 17:
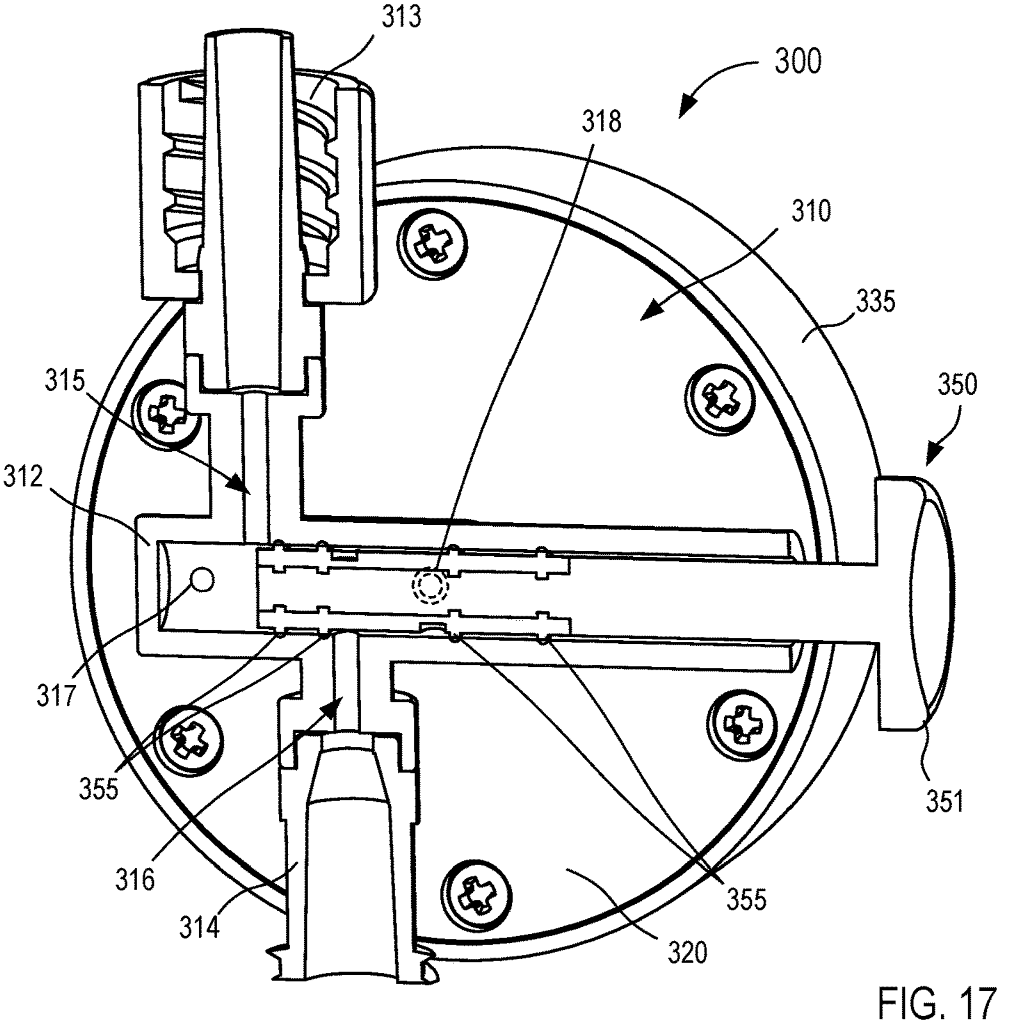
FIGS. 17 and 18 are each a cross-sectional view of the fluid control device of FIG. 12 taken along the line 17-17 in FIG. 14 and the line 18-18 in FIG. 15, shown in a first state.
Figure 18:
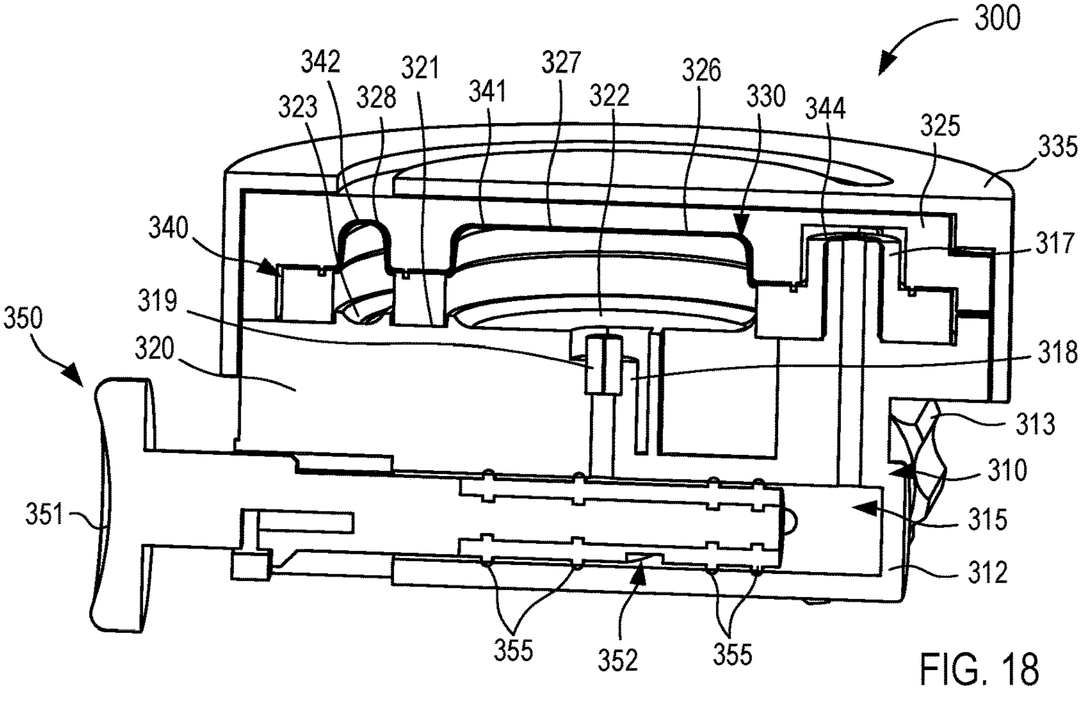

The sequestration portion 320 is configured to include, form, and/or house, a contour member 325 and the flow controller 340. More particularly, as shown in FIGS. 16-18, the sequestration portion 320 receives and/or is coupled to the contour member 325 such that the flow controller 340 is disposed therebetween. In some embodiments, the contour member 325 can be fixedly coupled to the sequestration portion 320 via an adhesive, ultrasonic welding, and/or any other suitable coupling method. In some embodiments, the contour member 325, the sequestration portion 320, and the flow controller 340 can collectively form a substantially fluid tight and/or hermetic seal that isolates the sequestration portion 320 for a volume outside of the sequestration portion 320.

As shown, a cover 335 is configured to be disposed about the contour member 325 such that the cover 335 and the sequestration portion 320 of the housing 310 enclose and/or house the contour member 325 and the flow controller 340. In some embodiments, the cover 335 can be coupled to the contour member 325 and/or the sequestration portion 320 via an adhesive, ultrasonic welding, one or more mechanical fasteners, a friction fit, a snap fit, a threaded coupling, and/or any other suitable manner of coupling. In some embodiments, the cover 335 can define an opening, window, slot, etc. configured to allow visualization of at least a portion of the sequestration chamber 330. While the contour member 325 and the cover 335 are described above as being separate pieces and/or components, in other embodiments, the contour member 325 can be integrated and/or monolithically formed with the cover 335.

The contour member 325 includes and/or forms a second contoured surface 326. The arrangement of the contour member 325 and the sequestration portion 320 of the housing 310 can be such that at least a portion of the first contoured surface 321 is aligned with and/or opposite a corresponding portion of the second contoured surface 326 of the contour member 325 (see e.g., FIG. 18). As such, a space, volume, opening, void, chamber, and/or the like defined between the first contoured surface 321 and the second contoured surface 326 forms and/or defines the sequestration chamber 330. Moreover, the flow controller 340 is disposed between the first contoured surface 321 and the second contoured surface 326 and can be configured to transition between a first state and a second state in response to a negative pressure differential and/or suction force applied to at least a portion of the sequestration chamber 330, as described in further detail herein.

The ports 317 and 318 of the housing 310 can be any suitable shape, size, and/or configuration. As described in detail above with reference to the first port 217, the first port 317 is in fluid communication with a first portion of the sequestration chamber 330 defined between the second contoured surface 326 and a first side of the flow controller 340 and is configured to provide and/or transfer a flow of bodily fluid from the inlet 313 and/or the fluid flow path 315 to the first portion of the sequestration chamber 330 in response to the flow controller 340 transitioning from a first state to a second state. As described above with reference to the second port 218, the second port 318 is in fluid communication with a second portion of the sequestration chamber 330 defined between the first contoured surface 321 and a second side of the flow controller 340 (e.g., opposite the first side). As such, the second port 318 can be configured to expose the second portion of the sequestration chamber 330 to a negative pressure differential and/or suction force resulting from the fluid collection device operable to transition the flow controller 340 from its first state to its second state, as described in detail above with reference to the device 200. In addition, the second port 318 can include and/or can be coupled to a restrictor 319 configured to limit and/or restrict a flow of fluid (e.g., air or gas) between the second portion of the sequestration chamber 330 and the fluid flow path 316, thereby modulating and/or controlling a magnitude of a pressure differential and/or suction force applied on or experienced by the flow controller 340, as described in detail above with reference to the restrictor 219 of the device 200.

The flow controller 340 disposed in the sequestration portion 320 of the housing 310 can be any suitable shape, size, and/or configuration. Similarly, the flow controller 340 can be formed of any suitable material (e.g., any suitable biocompatible material such as those described herein and/or any other suitable material). For example, the flow controller 340 can be a fluid impermeable bladder configured to be transitioned from a first state and/or configuration to a second state and/or configuration. In some embodiments, the flow controller 340 (e.g., bladder) can include any number of relatively thin and flexible portions configured to deform in response to a pressure differential across the flow controller 340. In some embodiments, the flow controller 340 can be substantially similar in at least form and/or function to the flow controller 240 described in detail above with reference to FIGS. 2-11. For example, in some embodiments, the flow controller 340 can be formed of or from any suitable material and/or can have any suitable durometer such as described the materials and/or durometers described above with reference to the flow controller 240. Similarly, the flow controller 340 can have a size, shape, surface finish, and/or material property(ies) configured to facilitate, encourage, and/or otherwise result in fluid flow with a desired set of flow characteristics, as described above with reference to the flow controller 240. Accordingly, portions of the flow controller 340 may not be described in further detail herein.

In the embodiment shown in FIG. 12-21, the flow controller 340 is a bladder formed of or from silicone having a durometer of about 30 Shore A. The flow controller 340 (e.g., bladder) includes a first deformable portion 341 and a second deformable portion 342. In addition, the flow controller 340 defines an opening 344 configured to receive at least a portion of the first port 317, as described above with reference to the flow controller 240. In some embodiments, the flow controller 340 can include one or more portions configured to form one or more seals with and/or between the flow controller 340 and each of the contoured surfaces 321 and 326, as described in further detail herein.

The deformable portions 341 and 342 of the flow controller 340 can be relatively thin and flexible portions configured to deform in response to a pressure differential between the first side of the flow controller 340 and the second side of the flow controller 340. More particularly, the deformable portions 341 and 342 can each have a thickness of about 0.005". As shown, for example, in FIGS. 18 and 20, the deformable portions 341 and 342 of the flow controller 340 correspond to and/or have substantially the same general shape as at least a portion of the contoured surfaces 321 and/or 326. As such, the deformable portions 341 and 342 and the corresponding portion(s) of the contoured surfaces 321 and/or 326 can collectively form and/or define one or more channels, volumes, and/or the like, which in turn, can receive the initial volume of bodily fluid, as described in further detail herein.

As described above with reference to the flow controller 240, the flow controller 340 is configured to transition between a first state and a second state. For example, when the flow controller 340 is in its first state, the first deformable portion 341 can be disposed adjacent to and/or substantially in contact with a first recess 327 formed by the second contoured surface 326 and the second deformable portion 342 can be disposed adjacent to and/or substantially in contact with a second recess 328 formed by the second contoured surface 326. As such, the first portion of the sequestration chamber 330 (e.g., the portion defined between the second contoured surface 326 and the first surface of the flow controller 340) can have a relatively small and/or relatively negligible volume. In contrast, when the flow controller 340 is transitioned from its first state to its second state (e.g., in response to a negative pressure applied and/or transmitted via the second port 318), the first deformable portion 341 can be disposed adjacent to and/or substantially in contact with a first recess 322 formed by the first contoured surface 321 and the second deformable portion 342 can be disposed adjacent to and/or substantially in contact with a second recess 323 formed by the first contoured surface 321. Accordingly, a volume of the first portion of the sequestration chamber 330 is larger when the flow controller 340 is in its second state than when the flow controller is in its first state. As described in detail above with reference to the sequestration chamber 230 and flow controller 240, the increase in the volume of the first portion of the sequestration chamber 330 can result in a negative pressure or vacuum therein that can be operable to draw a volume of air or gas as well as the initial volume of bodily fluid into the sequestration chamber 330.

While the flow controller 340 is particularly shown and described, in other embodiments, the flow controller 340 and/or the sequestration chamber 330 can have any suitable configuration and/or arrangement. For example, in some embodiments, the contoured surfaces 321 and/or 326 can include more or fewer recesses (e.g., the recesses 322 and 323 and the recesses 327 and 328). In other embodiments, a depth of one or more recesses can be modified. Similarly, the flow controller 340 can be modified in any suitable manner to substantially correspond to a shape and/or configuration of the contoured surfaces 321 and/or 326. While the flow controller 340 is described as being a bladder or the like including a number of deformable portions, in other embodiments, a flow controller can be arranged and/or configured as, for example, a bellows, a flexible pouch, an expandable bag, an expandable chamber, a plunger (e.g., similar to a syringe), and/or any other suitable reconfigurable container or the like. In addition, the sequestration chamber 330 at least partially formed by the flow controller 340 can have any suitable shape, size, and/or configuration.

The actuator 350 of the control device 300 can be any suitable shape, size, and/or configuration. At least a portion of the actuator 350 is disposed within the actuator portion 312 of the housing 310 and is configured to be transitioned between a first state, configuration, and/or position and a second state, configuration, and/or position. In the embodiment shown in FIGS. 12-21, the actuator 350 is configured as an actuator rod or plunger configured to be moved relative to the actuator portion 312 of the housing 310. The actuator 350 includes a set of seals 355 and defines a flow channel 352. The actuator 350 further includes an end portion 351 disposed outside of the housing 310 and configured to be engaged by a user to transition the actuator 350 between its first state, in which the fluid flow path 315 can establish fluid communication between the inlet 313 and the first port 317, and its second state, in which (1) the first port 317 (and thus, the sequestration chamber 330) are sequestered and/or fluidically isolated and (2) the inlet 313 and the outlet 314 are placed in fluid communication via at least a portion of the fluid flow paths 315 and 316 and/or the flow channel 352 of the actuator 350. As such, the actuator 350 is similar in form and/or function to the actuator 250 described above with reference to FIGS. 2-11. Thus, the actuator 350 is not described in further detail herein.

The device 300 can be used to procure a bodily fluid sample having reduced contamination (e.g., contamination from microbes such as, for example, dermally residing microbes, microbes external to the bodily fluid source, and/or the like) in a manner substantially similar to the manner described above with reference to the device 200. For example, prior to use, the device 300 can be in its first, initial, and/or storage state or operating mode, in which each of the flow controller 340 and the actuator 350 is in its respective first or initial state. With the device 300 in the first state, a user such as a doctor, physician, nurse, phlebotomist, technician, etc. can manipulate the device 300 to establish fluid communication between the inlet 313 and the bodily fluid source (e.g., a vein of a patient). Once the inlet 313 is placed in fluid communication with the bodily fluid source, the outlet 314 can be fluidically coupled to a fluid collection device (not shown in FIGS. 12-21). In the embodiment shown in FIGS. 12-21, for example, the fluid collection device can be an evacuated container, a culture bottle, a sample reservoir, a syringe, and/or any other suitable container or device configured to define or produce a negative pressure, suction force, vacuum, and/or energy potential.

When the actuator 350 is in the first position and/or configuration, the inlet 313 of the housing 310 is in fluid communication with, for example, the fluid flow path 315, which in turn, is in fluid communication with the first port 317 (see e.g., FIGS. 17 and 18). The outlet 314 of the of the housing 310 is in fluid communication with the fluid flow path 316, which in turn, is in fluid communication with the second port 318 (see e.g., FIGS. 17 and 18). As described in detail above, when the control device 300 is in the first state or operating mode (e.g., when the actuator 350 and the flow controller 340 are each in their first state), fluidically coupling the fluid collection device to the outlet 314 generates and/or otherwise results in a negative pressure differential and/or suction force within at least a portion of the fluid flow path 316 and, in turn, within the portion of the sequestration chamber 330 defined between a surface of the flow controller 340 (e.g., a first surface) and the first contoured surface 321 of the housing 310.

The flow controller 340 is in the first state and/or configuration prior to the fluid collection device being coupled to the outlet 314. In the embodiment shown in FIGS. 12-21, the flow controller 340 is a fluid impermeable bladder and/or the like that can have a flipped, inverted, collapsed, and/or empty configuration (e.g., the first state and/or configuration) prior to coupling the fluid collection device to the outlet 314. For example, as shown in FIG. 18, the flow controller 340 can be disposed adjacent to and/or in contact with the second contoured surface 326 when the flow controller 340 is in its first state and/or configuration.

Figure 20:
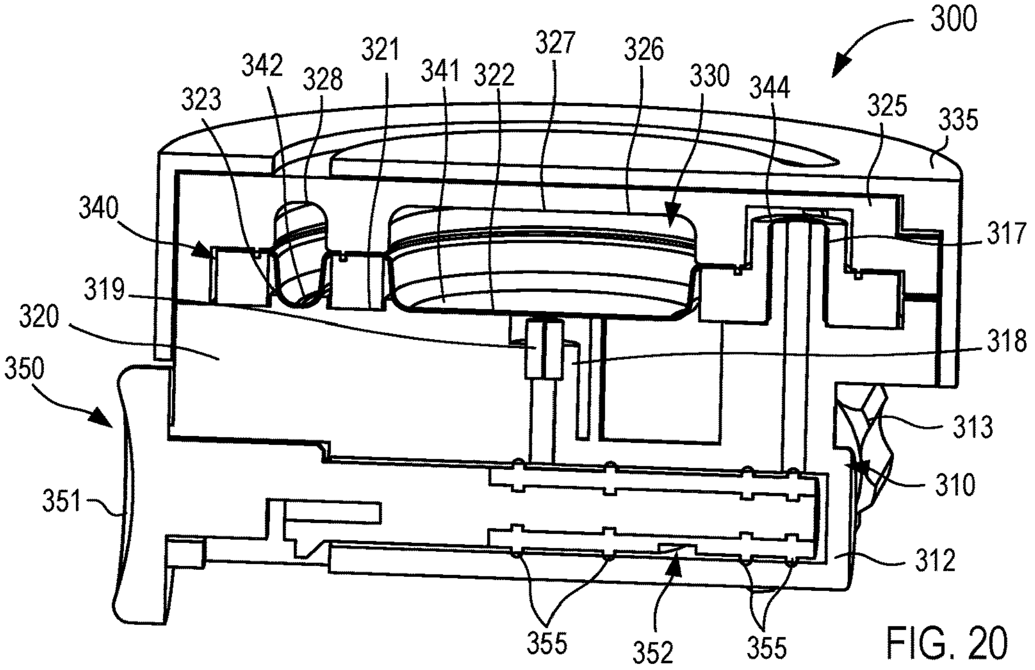

As described above, the flow controller 340 is configured to transition from its first state and/or configuration to its second state and/or configuration in response to the negative pressure differential and/or suction force generated within the portion of the sequestration chamber 330 defined between the flow controller 340 and the first contoured surface 321. For example, the flow controller 340 can be disposed adjacent to and/or in contact with the second contoured surface 326 when the flow controller 340 is in its first state (FIG. 18) and can be transitioned, moved, "flipped", placed, and/or otherwise reconfigured into its second state in which the flow controller 340 is disposed adjacent to and/or in contact with the first contoured surface 321 (FIG. 20). Moreover, the control device 300 is placed in its second state and/or configuration when the actuator 350 is in its first state and the flow controller 340 is in its second state.

The transitioning of the flow controller 340 results in an increase in an inner volume of the portion of the sequestration chamber 330 defined between a surface of the flow controller 340 (e.g., a second surface opposite the first surface) and the second contoured surface 326. As described in detail above with reference to the device 200, the increase in the inner volume can, in turn, result in a negative pressure differential between the portion of the sequestration chamber 330 (defined at least in part by the flow controller 340) and, for example, the inlet 313 that is operable in drawing at least a portion of an initial flow, amount, or volume of bodily fluid from the inlet 313, through the fluid flow path 315 and the first port 317, and into the portion of the sequestration chamber 330. In some instances, the initial volume and/or flow of bodily fluid can be transferred into the sequestration chamber 330 until, for example, the flow controller 340 is fully expanded, flipped, and/or transitioned, until the negative pressure differential is reduced and/or equalized, and/or until a desired volume of bodily fluid is disposed within the portion of the sequestration chamber 330. Moreover, the restrictor 319 can be configured to restrict, limit, control, and/or modulate a magnitude of the negative pressure differential and/or suction force generated within the sequestration chamber 330 and/or on a surface of the flow controller 340, which in turn, can modulate a suction force within one or more flow paths and/or within the bodily fluid source (e.g., the vein of the patient), as described above with reference to the device 200. In other embodiments, the second port 318 and/or any suitable portion of the device 300 can be configured to modulate a suction force within one or more portions of the sequestration chamber 330 in any suitable manner such as, for example, those described above with reference to the device 200.

In some embodiments, the shape, size, and/or arrangement of the sequestration chamber 330 and/or the flow controller 340, the magnitude of the negative pressure differential or suction force, and/or the way in which the negative pressure differential or suction force is exerted can dictate and/or control a rate and/or manner in which the flow controller 340 is transitioned from the first state to the second state. For example, while the flow controller 240 is described above as including the first deformable portion 241, the second deformable portion 242, and the third deformable portion 243, the flow controller 340 included in the embodiment shown in FIGS. 12-21 includes only the first deformable portion 341 and the second deformable portion 342. Moreover, as shown in FIGS. 18 and 20, the recesses 322 and 323 of the first contoured surface 321 have substantially the same depth. In some embodiments, such an arrangement can, for example, limit and/or reduce an amount of negative pressure and/or suction force sufficient to transition and/or flip the first deformable portion 341 relative to the amount of negative pressure and/or suction force sufficient to transition and/or flip the first and second deformable portions 341 and 342 of the flow controller 340.

As described above, in some embodiments, the first deformable portion 341 can have a thickness and/or stiffness that is greater than a thickness and/or stiffness of the second deformable portion 342 such that the second deformable portion 342 completes or substantially completes its transition and/or flip before the first deformable portion 341 completes or substantially completes its transition and/or flip. In other embodiments, the flow controller 340 can include any suitable feature, structure, material property, surface finish, and/or the like, and/or any other portion of the device 300 can include any suitable feature, structure, etc. configured to control an order and/or manner in which the flow controller 340 transitions from the first state to the second state, such as any of those described above with reference to the flow controller 240. In some embodiments, the arrangement of the flow controller 340 may result in the device 300 being compatible with fluid collection devices having a relatively low amount of negative pressure. In some embodiments, such an arrangement may also facilitate and/or simplify one or more manufacturing processes and/or the like. In some instances, controlling the rate, order, and/or manner can result in one or more desired flow characteristic associated with a flow of air, gas, and/or bodily fluid into and/or through at least a portion of the sequestration chamber 230.

As described above with reference to the deformable portions 241 and 242, the first deformable portion 341 and the first recess 327 of the second contoured surface 326 (e.g., a first volume of the sequestration chamber 330) can be configured to receive a volume of air that was within the fluid flow path between the bodily fluid source and the sequestration chamber 330 prior to the fluid flow path receiving and/or being filled with the flow of bodily fluid. In other words, the transitioning of the flow controller 340 can vent or purge air or gas from the fluid flow path between the bodily fluid source and the sequestration chamber 330, which can then be stored or contained within the first and second volumes of the sequestration chamber 330. On the other hand, a portion of the sequestration chamber 330 collectively defined by the second deformable portion 342 and the second recess 328 of the second contoured surface 326 (e.g., a second volume of the sequestration chamber 330) can be configured to receive the initial volume of bodily fluid that flows through the fluid flow path between the bodily fluid source and the sequestration chamber 330 after the air or gas is vented and/or purged. Thus, as described above with reference to the device 200, the initial volume can be transferred into the sequestration chamber 330.

In some instances, the arrangement of the sequestration chamber 330 and/or the flow controller 340 can result in an even flow of the initial volume of bodily fluid into, for example, the second volume of the sequestration chamber 330. For example, as described in detail above with reference to the device 200, the sequestration chamber 330 and/or the flow controller 340 can be configured and/or arranged such that bodily fluid flows into and/or through at least a portion of the sequestration chamber 330 (e.g., the second volume of the sequestration chamber 330) with a uniform flow front and substantially without mixing with a volume of air in the sequestration chamber 330. In other embodiments, a flow controller can have any other suitable arrangement to result in desired rate, manner, and/or order of conveying the initial volume of bodily fluid into one or more portions or volumes of the sequestration chamber 330 such as, for example, any of those described above with reference to the device 200.

Having transferred the initial volume of bodily fluid into the sequestration chamber 330, a force can be exerted on the end portion 351 of the actuator 350 to transition and/or place the actuator 350 in its second position, state, operating mode, and/or configuration, as described in above. In some instances, prior to exerting the force on the end portion 351 of the actuator 350, the actuator 350 may be transitioned from a locked configuration or state to an unlocked configuration or state. In the embodiment shown in FIGS. 12-21, the transition of the actuator 350 can be achieved by and/or can otherwise result from user interaction and/or manipulation of the actuator 350. In other embodiments, however, the transition of the actuator 350 can occur automatically in response to negative pressure and/or associated flow dynamics within the device 300, and/or enacted by or in response to an external energy source that generates one or more dynamics or states that result in the transitioning of the actuator 350.

Figure 19:
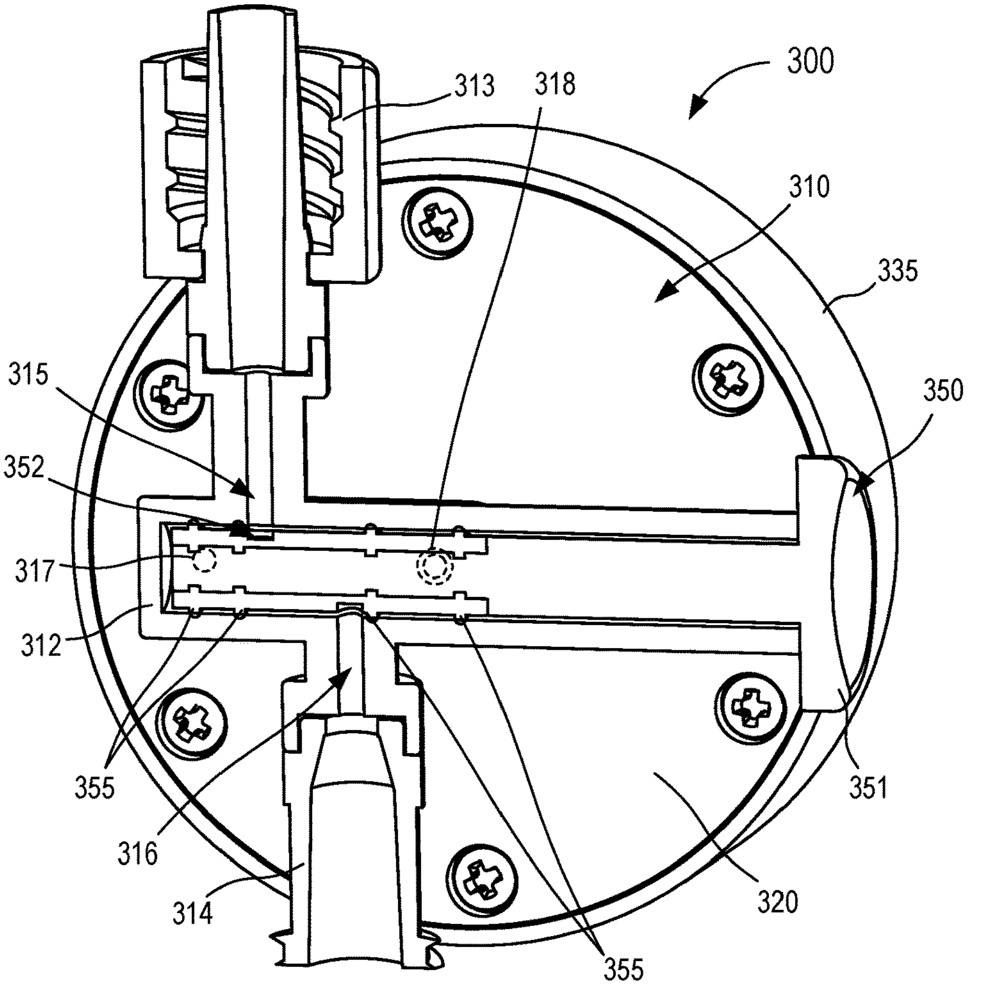
FIGS. 19 and 20 are each a cross-sectional view of the fluid control device of FIG. 12 taken along the line 17-17 in FIG. 14 and the line 18-18 in FIG. 15, shown in a second state.
Figure 21:
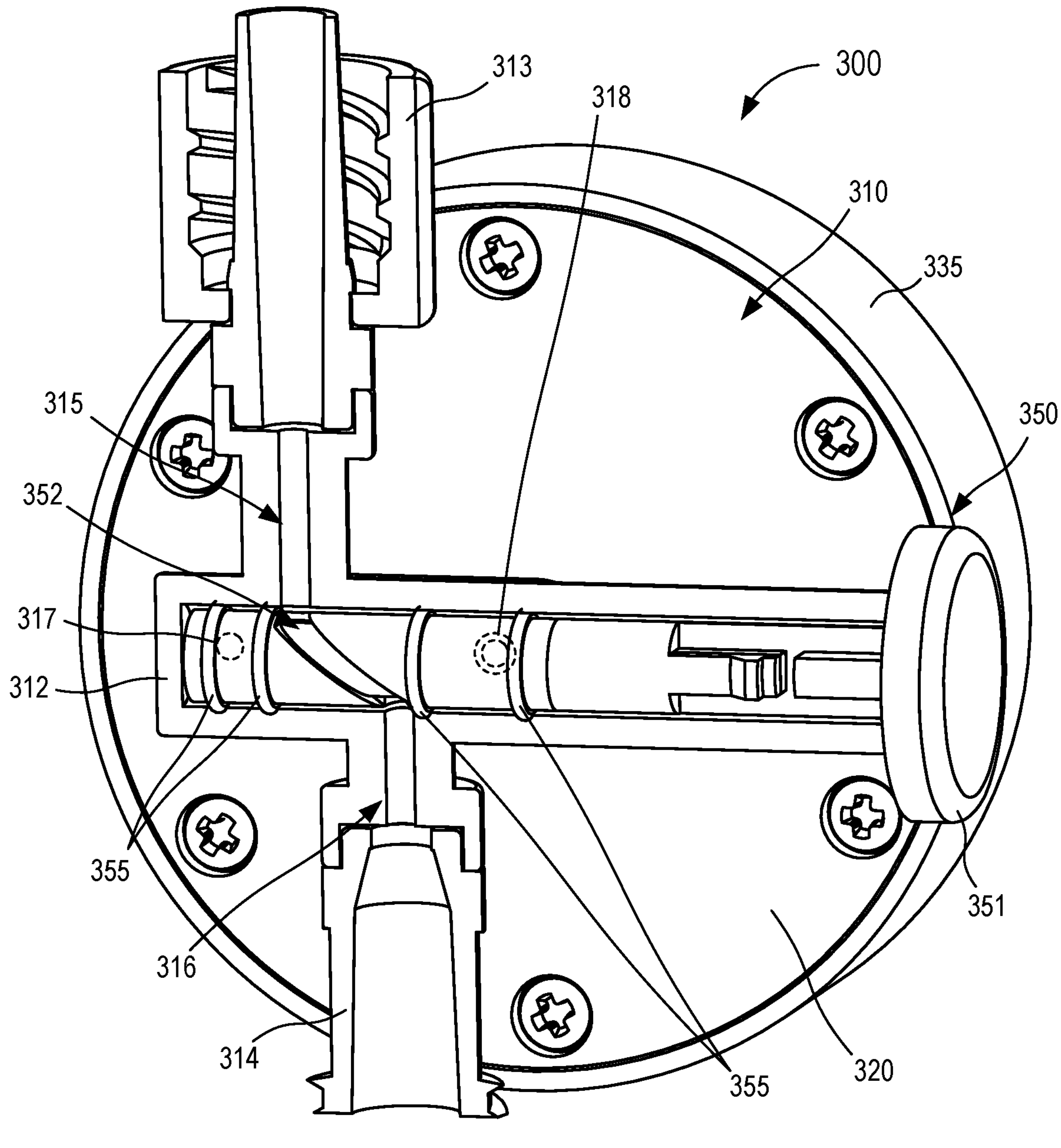
FIG. 21 is a partial cross-sectional view of the fluid control device of FIG. 12 taken along the line 18-18 in FIG. 15, shown in the second state.
Figure 22:
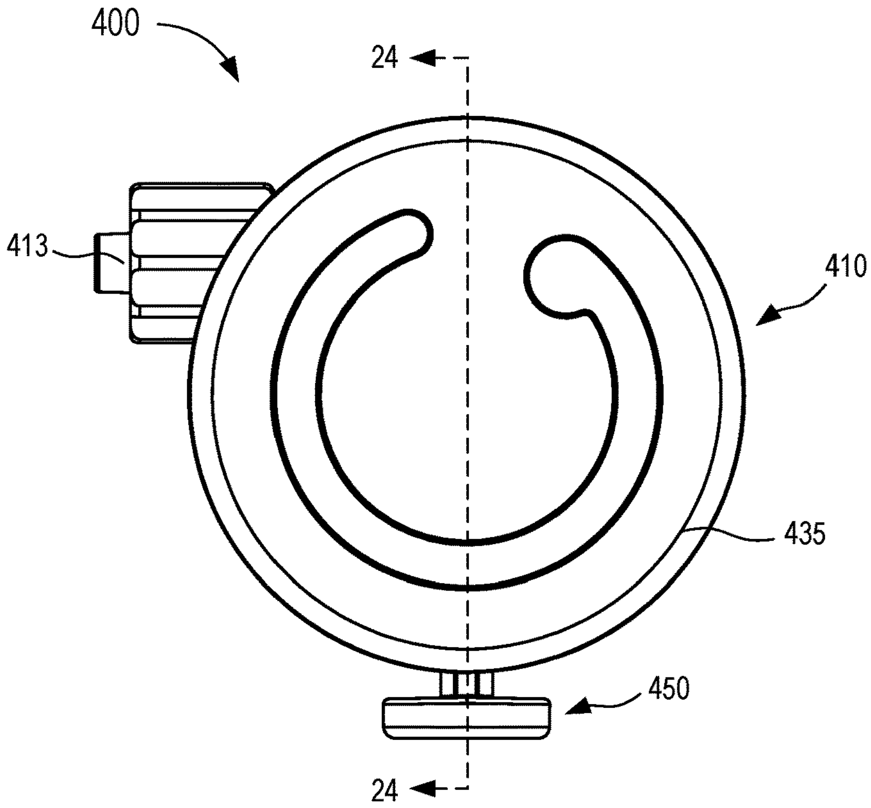
FIGS. 22 and 23 are a front perspective view and a rear perspective view, respectively, of a fluid control device according to an embodiment.
Figure 23:
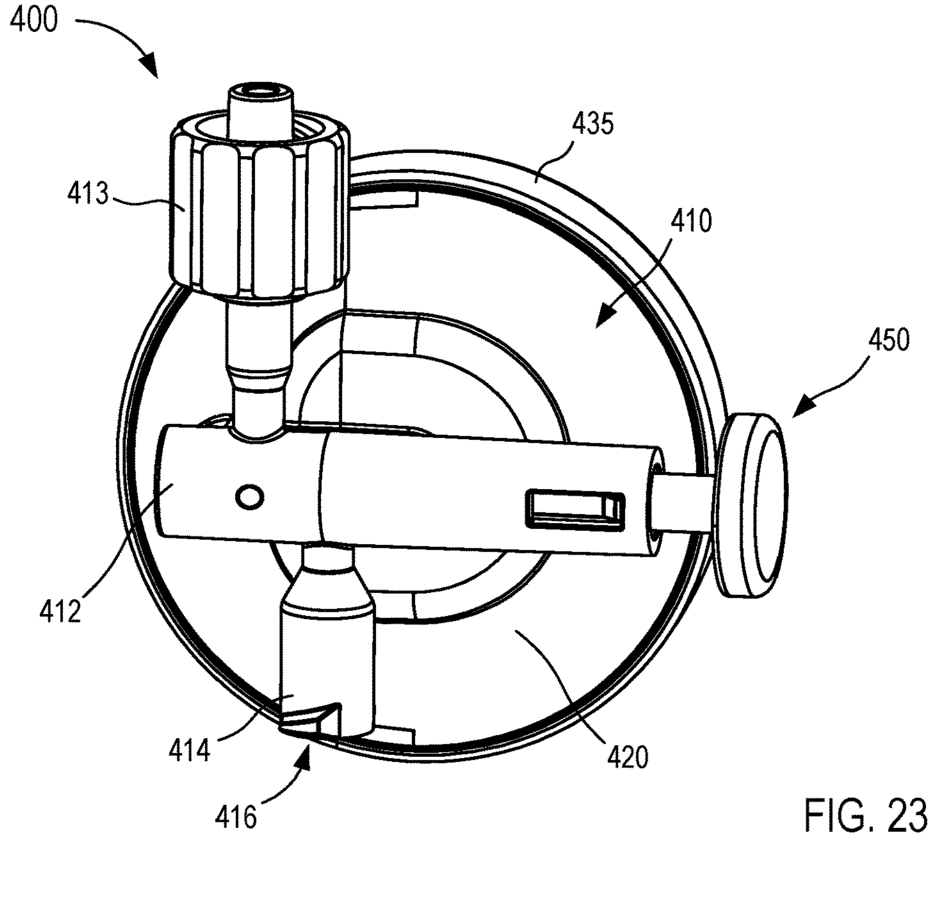

As shown in FIGS. 19-21, the control device 300 is placed in its third state when each of the flow controller 340 and the actuator 350 is in its second state. When the actuator 350 is transitioned to its second state, position, and/or configuration, the inlet 313 and the outlet 314 are placed in fluid communication (e.g., via the fluid flow path 316 and/or the flow channel 352) while the fluid flow path 315 and/or the first port 317 is/are sequestered, isolated, and/or otherwise not in fluid communication with the inlet 313 and/or the outlet 314. As such, the initial volume of bodily fluid is sequestered in the portion of the sequestration chamber 330 (e.g., the third volume of the sequestration chamber 330, as described above). Moreover, in some instances, contaminants such as, for example, dermally residing microbes and/or any other contaminants can be entrained and/or included in the initial volume of the bodily fluid and thus, are sequestered in the sequestration chamber 330 when the initial volume is sequestered therein. As such, the negative pressure otherwise exerted on or through the fluid flow path 316 and through the second port 318 is now exerted on or through the outlet 314 and the inlet 313 via, for example, at least a portion of the fluid flow paths 315 and 316 and/or the flow channel 352 of the actuator 350 (FIG. 21). In response, bodily fluid can flow from the inlet 313, through the actuator portion 312 of the housing 310, through the outlet 314, and into the fluid collection device coupled to the outlet 314. Accordingly, the device 300 can function in a manner substantially similar to that of the devices 100 and/or 200 described in detail above.

FIGS. 22-27 illustrate a fluid control device 400 according to another embodiment. The fluid control device 400 (also referred to herein as "control device" or "device") can be similar in at least form and/or function to the devices 100, 200, and/or 300 described above. For example, as described above with reference to the devices 100, 200, and/or 300, in response to being placed in fluid communication with a negative pressure source (e.g., a suction or vacuum source), the device 400 can be configured to (1) withdraw bodily fluid from a bodily fluid source into the device 400, (2) divert and sequester a first portion or amount (e.g., an initial volume) of the bodily fluid in a portion of the device 400, and (3) allow a second portion or amount (e.g., a subsequent volume) of the bodily fluid to flow through the device 400—bypassing the sequestered initial volume—and into a fluid collection device fluidically coupled to the device 400. As such, contaminants or the like can be sequestered in or with the initial volume of bodily fluid, leaving the subsequent volume of bodily fluid substantially free of contaminants. In some embodiments, portions and/or aspects of the control device 400 can be similar to and/or substantially the same as portions and/or aspects of at least the control device 200 described above with reference to FIGS. 2-11. Accordingly, such similar portions and/or aspects may not be described in further detail herein.

The fluid control device 400 includes a housing 410, a flow controller 440, and an actuator 450. In some embodiments, the control device 400 or at least a portion of the control device 400 can be arranged in a modular configuration (e.g., including one or more independent or separate components that are later assembled) or can be arranged in an integrated or at least partially integrated configuration (e.g., including one or more components that are pre-assembled or pre-coupled), as described above with reference to the device 200. For example, in some embodiments, the control device 400 can include and/or can be coupled to a fluid collection device and/or an inlet device such as any of those described above.

The housing 410 of the control device 400 can be any suitable shape, size, and/or configuration. In general, the housing 410 can be substantially similar in at least form and/or function to the housing 210. Accordingly, while certain components, features, aspects, and/or functions of the housing 410 are identified in the drawings and discussed below, such similarities are not described in further detail herein and should be considered similar to the corresponding components, features, aspects, and/or functions described above with reference to the device 200 unless explicitly described to the contrary.

The housing 410 includes an actuator portion 412 and a sequestration portion 420. The actuator portion 412 receives at least a portion of the actuator 450. The sequestration portion 420 is coupled to a cover 435 and includes, receives, houses, and/or at least partially defines a sequestration chamber 430. As described in further detail herein, the housing 410 can include and/or can define a first port 417 and a second port 418, each of which establishes fluid communication between the actuator portion 412 and the sequestration portion 420 of the housing 410 to selectively control and/or allow a flow of fluid through one or more portions of the housing 410.

The actuator portion 412 of the housing 410 includes an inlet 413 and an outlet 414, and defines a fluid flow path 415 (e.g., a first fluid flow path) that is configured to selectively place the inlet 413 in fluid communication with the first port 417 and a fluid flow path 416 (e.g., a second fluid flow path) that is configured to selectively place the outlet 414 in fluid communication with the second port 418. The actuator portion 412 of the housing 410 can be substantially similar in at least form and/or function to the actuator portion 212 of the housing 210 and thus, is not described in further detail herein.

The sequestration portion 420 of the housing 410 can be any suitable shape, size, and/or configuration. The sequestration portion 420 is configured to include, form, and/or house, a contour member 425 and the flow controller 440. More specifically, a cover 435 is configured to be disposed about the contour member 425 such that the cover 435 and the sequestration portion 420 of the housing 410 enclose and/or house the contour member 425 and the flow controller 440. The sequestration portion 420 of the housing 410 and/or components thereof or coupled thereto can be substantially similar in at least form and/or function to the sequestration portion 220 of the housing 210 (and/or components thereof or coupled thereto) and thus, is/are not described in further detail herein.

As shown for example, in FIGS. 24-27, the sequestration portion 420 includes and/or forms an inner surface, a portion of which is arranged and/or configured to form a first contoured surface 421. At least a portion of the first contoured surface 421 can form and/or define a portion of the sequestration chamber 430, as described in further detail herein. Furthermore, the first port 417 and the second port 418 are configured to form and/or extend through a portion of the first contoured surface 421 to selectively place the sequestration chamber 430 in fluid communication with the fluid flow paths 415 and 416, as described above with reference to the device 200.

Figure 24:
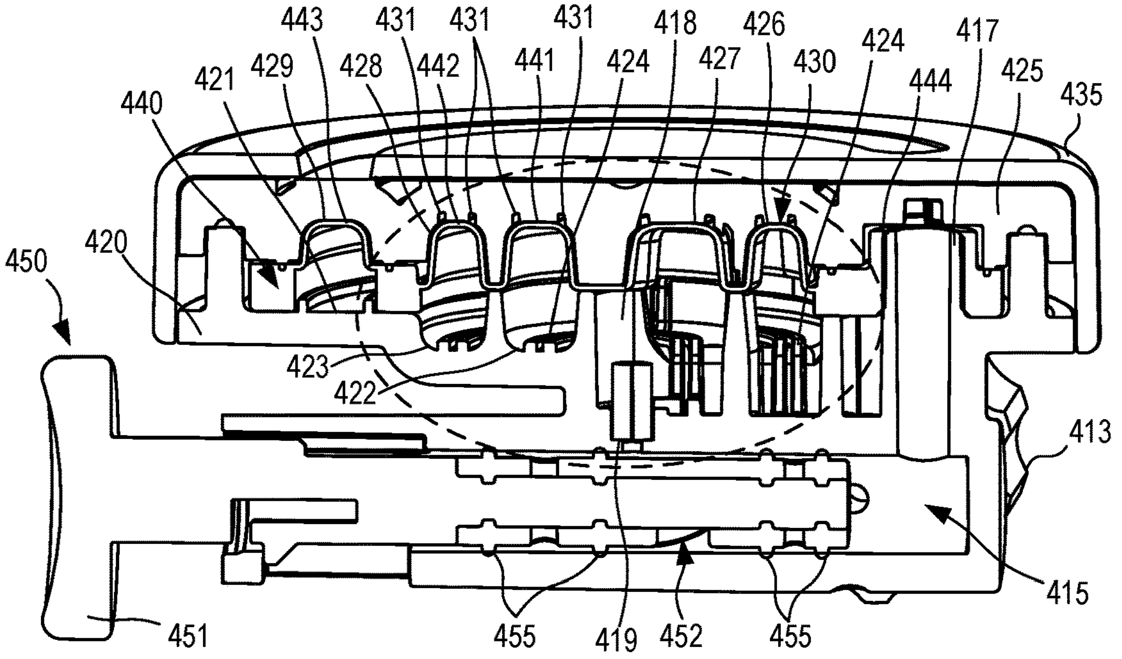
FIGS. 24 and 25 are each a cross-sectional view of the fluid control device of FIG. 22 taken along the line 24-24 and shown in a first state.
Figure 25:
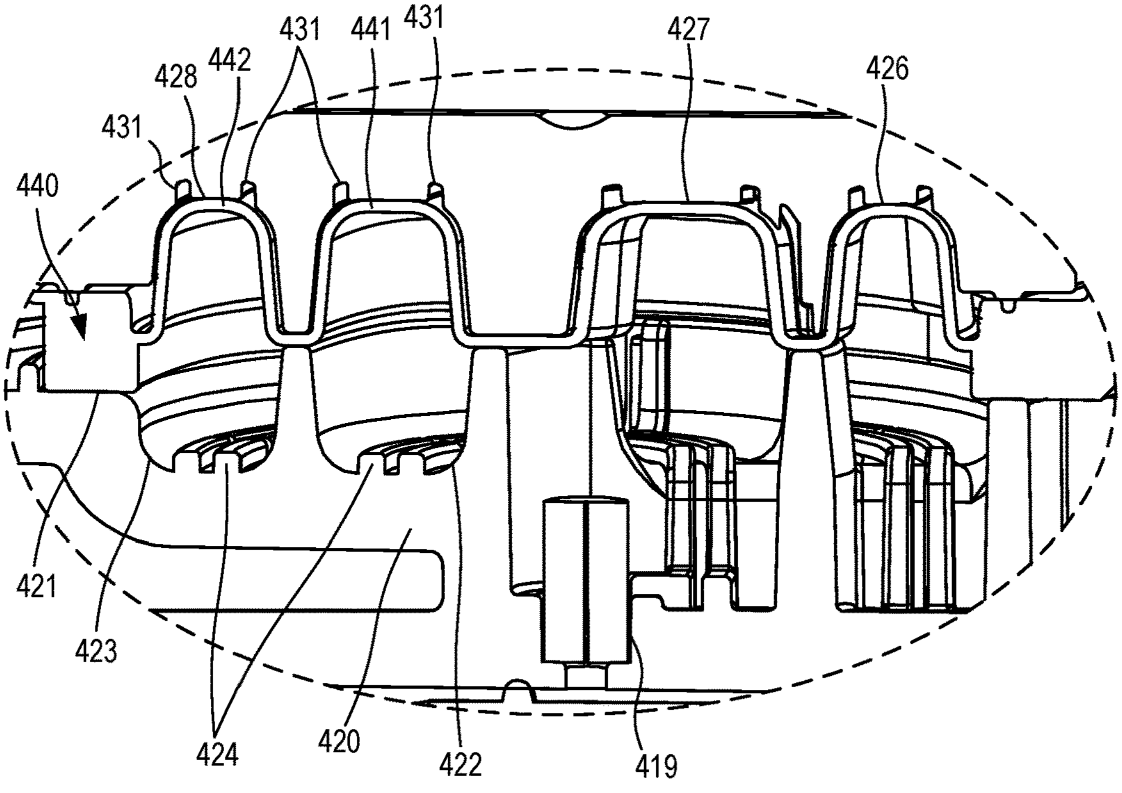
Figure 26:
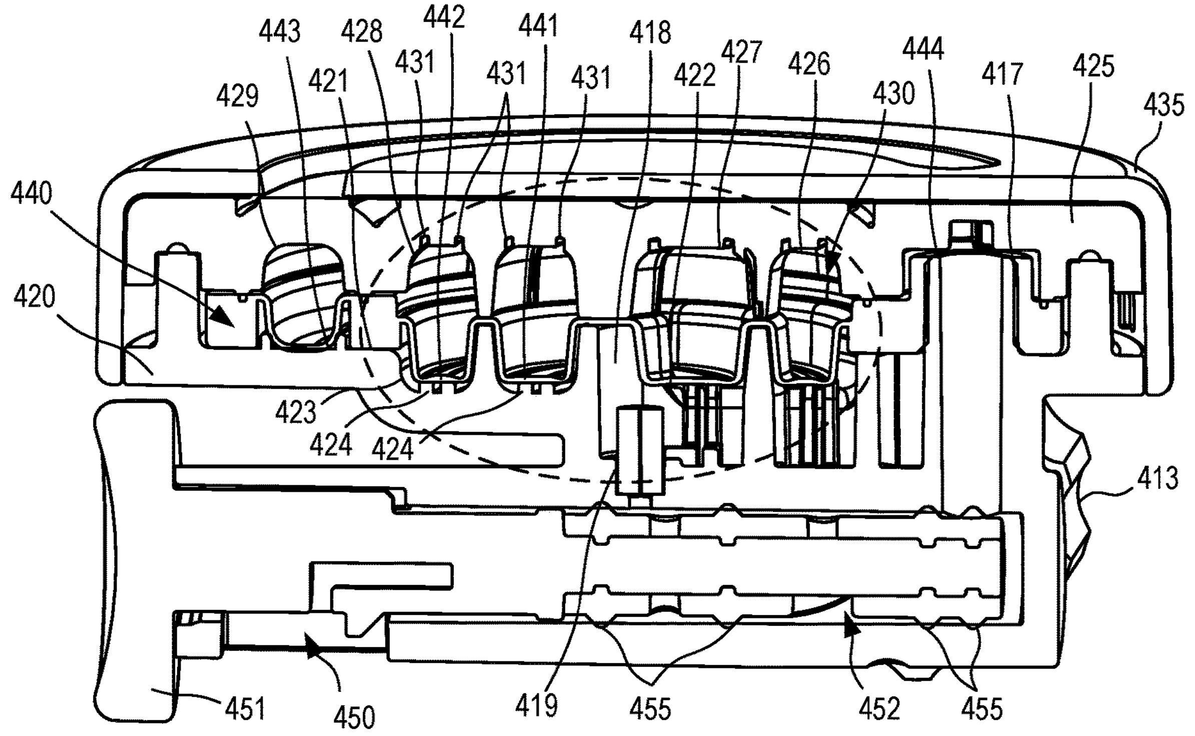
FIGS. 26 and 27 are each a cross-sectional view of the fluid control device of FIG. 22 taken along the line 24-24 and shown in a second state.
Figure 27:
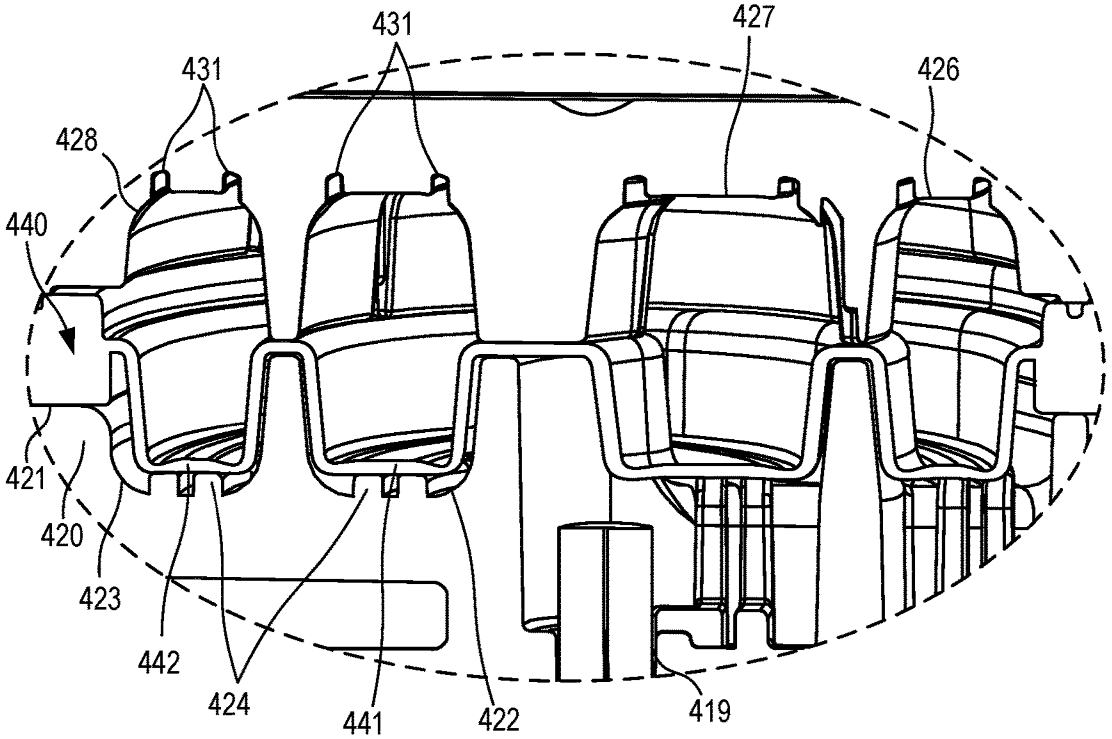

The first contoured surface 421 can be any suitable shape, curvature, and/or texture, and can, for example, be substantially similar to the first contoured surface 221 of the housing 220. For example, the first contoured surface 421 includes and/or forms at least a first recess 422 and a second recess 423. The first contour surface 421 can differ from the first contoured surface 221, however, by including any number of ventilation ridges 424, as shown in FIGS. 24-27. The distribution of the ventilation ridges 424 on the first contour surface 421 can include multiple arrangements. For example, the first contour surface 421 can have one ventilation ridge 424, multiple ventilation ridges 424, multiple concentric ventilation ridges 424, etc. disposed within and/or formed by the first recess 422 and/or one ventilation ridge 424, multiple ventilation ridges 424, or multiple concentric ventilation ridges 424 disposed within and/or formed by the second recess 423 of the first contour surface 421, as shown in FIGS. 25 and 27. In some implementations, the ventilation ridges 424 are configured to reduce and/or control the ability or the likelihood of the flow controller 440 or portions thereof forming a seal when placed in contact with the first contour surface 421 in response to a negative pressure applied and/or transmitted via the second port 418 (e.g., a negative pressure in a volume between the first contoured surface 421 and the flow controller 440). Said another way, the ventilation ridges 424 can form discontinuities along one or more portions of the first contoured surface 421 that, for example, can prevent air from being trapped in localized areas between the flow controller 440 and one or more portions of the first contour surface 421 by allowing air to flow freely between the flow controller 440 and one or more portions of the first contour surface 421, as described in further detail herein.

As shown in FIGS. 24-27, the sequestration portion 420 receives and/or is coupled to the contour member 425 such that the flow controller 440 is disposed therebetween. In some embodiments, the contour member 425 can be substantially similar in at least form and/or function to the contour member 225 described above with reference to the device 200. For example, the contoured member 425 includes and/or forms a second contoured surface 426. The second contour surface 426 can be any suitable shape, curvature, and/or texture, and can, for example, be substantially similar to the second contoured surface 226 of the housing 220. For example, the second contoured surface 426 includes and/or forms a first recess 427, a second recess 428, and a third recess 429. The second contour surface 426 can differ from the second contoured surface 226, however, by including any number of ventilation channels 431, as shown in FIGS. 24-27. The distribution of the ventilation channels 431 on the second contour surface 426 can include multiple arrangements. For example, the second contour surface 426 can be configured to have one ventilation channel 431, multiple ventilation channels 431, or multiple concentric ventilation channels 431 disposed within and/or formed by the first recess 427 and/or one ventilation channel 431, multiple ventilation channels 431, or multiple concentric ventilation channels 431 disposed within and/or formed by the second recess 428 of the second contour surface 426, as shown in FIGS. 25 and 27. The ventilation channels 431 are configured to reduce and/or control the ability or the likelihood of the flow controller 440 or portions thereof forming a seal when placed in contact with the second contour surface 426 in response to a positive pressure (e.g., in a volume between the first contoured surface 421 and the flow controller 440), as described above with reference to the ventilation ridges 424.

While the first contour surface 421 is described above as including the ventilation ridges 424 and the second contour surface 426 is described above as including the ventilation channels 431, it should be understood that the ventilation ridges 424 and the ventilation channels 431 have been presented by way of example only and not limitation. Various alternatives and/or combinations are contemplated. For example, in some embodiments, the first contour surface 421 can include ventilation channels while the second contour surface 426 can include ventilation ridges. In other embodiments, the first contour surface 421 and/or the second contour surface 426 can include a combination of ventilation channels and ventilation ridges. As such, the contour surfaces 421 and 426 can include one or more discontinuity having any suitable shape, size, and/or configuration that can allow for and/or otherwise ensure that air can flow between the flow controller 440 and the contour surfaces 421 and 426. Moreover, while each of the contour surfaces 421 and 426 is shown as including a ventilation feature or discontinuity, in other embodiments, the first contour surface 421 can include a ventilation feature or discontinuity while the second contour surface 426 does not, or vice versa.

The flow controller 440 disposed in the sequestration portion 420 of the housing 410 can be any suitable shape, size, and/or configuration. Similarly, the flow controller 440 can be formed of any suitable material (e.g., any suitable biocompatible material such as those described herein and/or any other suitable material). For example, the flow controller 440 can be a fluid impermeable bladder configured to be transitioned from a first state and/or configuration to a second state and/or configuration. In some embodiments, the flow controller 440 (e.g., bladder) can include any number of relatively thin and flexible portions configured to deform in response to a pressure differential across the flow controller 440. In some embodiments, the flow controller 440 can be substantially similar in at least form and/or function to the flow controller 240 described in detail above with reference to FIGS. 2-11. For example, in some embodiments, the flow controller 440 can be formed of or from any suitable material and/or can have any suitable durometer such as described the materials and/or durometers described above with reference to the flow controller 240. Similarly, the flow controller 440 can have a size, shape, surface finish, and/or material property(ies) configured to facilitate, encourage, and/or otherwise result in fluid flow with a desired set of flow characteristics, as described above with reference to the flow controller 240. Accordingly, portions of the flow controller 440 may not be described in further detail herein.

In the embodiment shown in FIG. 22-27, the flow controller 440 is a bladder formed of or from silicone having a durometer of about 30 Shore A. The flow controller 440 (e.g., bladder) includes a first deformable portion 441, a second deformable portion 442, and a third deformable portion 443. In addition, the flow controller 440 defines an opening 444 configured to receive at least a portion of the first port 417, as described above with reference to the flow controller 240. In some embodiments, the flow controller 440 can include one or more portions configured to form one or more seals with and/or between the flow controller 440 and each of the contoured surfaces 421 and 426. For example, as shown in FIGS. 24-27, the deformable portions 441, 442 and 443 of the flow controller 440 correspond to and/or have substantially the same general shape as at least a portion of the contoured surfaces 421 and/or 426. As such, the deformable portions 441, 442 and 443 and the corresponding portion(s) of the contoured surfaces 421 and/or 426 can collectively form and/or define one or more volumes, and/or the like, which in turn, can receive the initial volume of bodily fluid, as described in further detail herein.

As described above with reference to the flow controller 240, the flow controller 440 is configured to transition between a first state and a second state. For example, when the flow controller 440 is in its first state, the first deformable portion 441 can be disposed adjacent to and/or substantially in contact with a first recess 427 formed by the second contoured surface 426, the second deformable portion 442 can be disposed adjacent to and/or substantially in contact with a second recess 428, and the third deformable portion 443 can be disposed adjacent to and/or substantially in contact with a second recess 429 formed by the second contoured surface 426. As such, the first portion of the sequestration chamber 430 (e.g., the portion defined between the second contoured surface 426 and the first surface of the flow controller 440) can have a relatively small and/or relatively negligible volume. In contrast, when the flow controller 440 is transitioned from its first state to its second state (e.g., in response to a negative pressure applied and/or transmitted via the second port 418), at least the deformable portions 441, 442, and 443 are disposed adjacent to and/or substantially in contact with the first contoured surface 421. More specifically, the first deformable portion 421 can be disposed adjacent to and/or substantially in contact with a first recess 422 formed by the first contoured surface 421, the second deformable portion 442 can be disposed adjacent to and/or substantially in contact with a second recess 423 formed by the first contoured surface 421, and the third deformable portion 243 can be disposed adjacent to and/or substantially in contact with, for example, a non-recessed portion of the first contoured surface 421, as described above with reference to the flow controller 240.

The actuator 450 of the control device 400 can be any suitable shape, size, and/or configuration. At least a portion of the actuator 450 is disposed within the actuator portion 412 of the housing 410 and is configured to be transitioned between a first state, configuration, and/or position and a second state, configuration, and/or position. In the embodiment shown in FIGS. 22-27, the actuator 450 is configured as an actuator rod or plunger configured to be moved relative to the actuator portion 412 of the housing 410. The actuator 450 includes a set of seals 455 and defines a flow channel 452. The actuator 450 further includes an end portion 451 disposed outside of the housing 410 and configured to be engaged by a user to transition the actuator 450 between its first state, in which the fluid flow path 415 can establish fluid communication between the inlet 413 and the first port 417, and its second state, in which (1) the first port 417 (and thus, the sequestration chamber 430) are sequestered and/or fluidically isolated and (2) the inlet 413 and the outlet 414 are placed in fluid communication via at least a portion of the fluid flow paths 415 and 416 and/or the flow channel 452 of the actuator 450. As such, the actuator 450 is similar in form and/or function to the actuator 250 described above with reference to FIGS. 2-11. Thus, the actuator 450 is not described in further detail herein.

The device 400 can be used to procure a bodily fluid sample having reduced contamination (e.g., contamination from microbes such as, for example, dermally residing microbes, microbes external to the bodily fluid source, and/or the like) in a manner substantially similar to the manner described above with reference to the device 200. For example, prior to use, the device 400 can be in its first, initial, and/or storage state or operating mode, in which each of the flow controller 440 and the actuator 450 is in its respective first or initial state. With the device 400 in the first state, a user such as a doctor, physician, nurse, phlebotomist, technician, etc. can manipulate the device 400 to establish fluid communication between the inlet 413 and the bodily fluid source (e.g., a vein of a patient). Once the inlet 413 is placed in fluid communication with the bodily fluid source, the outlet 414 can be fluidically coupled to a fluid collection device (not shown in FIGS. 22-27). In the embodiment shown in FIGS. 22-27, for example, the fluid collection device can be an evacuated container, a culture bottle, a sample reservoir, a syringe, and/or any other suitable container or device configured to define or produce a negative pressure, suction force, vacuum, and/or energy potential.

When the actuator 450 is in the first position and/or configuration, the inlet 413 of the housing 410 is in fluid communication with, for example, the fluid flow path 415, which in turn, is in fluid communication with the first port 417. The outlet 414 of the of the housing 410 is in fluid communication with the fluid flow path 416, which in turn, is in fluid communication with the second port 418 (see e.g., FIG. 24). As described in detail above, when the control device 400 is in the first state or operating mode (e.g., when the actuator 450 and the flow controller 440 are each in their first state), fluidically coupling the fluid collection device to the outlet 414 generates and/or otherwise results in a negative pressure differential and/or suction force within at least a portion of the fluid flow path 416 and, in turn, within the portion of the sequestration chamber 430 defined between a surface of the flow controller 440 (e.g., a first surface) and the first contoured surface 421 of the housing 410.

The flow controller 440 is in the first state and/or configuration prior to the fluid collection device being coupled to the outlet 414. In the embodiment shown in FIGS. 22-27, the flow controller 440 is a fluid impermeable bladder and/or the like that can have a flipped, inverted, collapsed, and/or empty configuration (e.g., the first state and/or configuration) prior to coupling the fluid collection device to the outlet 414. For example, as shown in FIGS. 24 and 25, the flow controller 440 can be disposed adjacent to and/or in contact with the second contoured surface 426 when the flow controller 440 is in its first state and/or configuration.

As described above, the controller 440 is configured to transition from its first state and/or configuration to its second state and/or configuration in response to the negative pressure differential and/or suction force generated within the portion of the sequestration chamber 430 defined between the flow controller 440 and the first contoured surface 421. For example, the flow controller 440 can be disposed adjacent to and/or in contact with the second contoured surface 426 when the flow controller 440 is in its first state (FIGS. 24 and 25) and can be transitioned, moved, "flipped", placed, and/or otherwise reconfigured into its second state in which the flow controller 440 is disposed adjacent to and/or in contact with the first contoured surface 421 (FIGS. 26 and 27). Moreover, the ventilation channels 431 formed by the second contour surface 426 can allow air to flow between the second contoured surface 426 and the flow controller 440, which can, in some instances, reduce a likelihood of pockets of air being trapped between the second contoured surface 426 and the flow controller 440 if and/or when a positive pressure is applied in a volume between the flow controller 440 and the first contoured surface 421 via the port 418 (e.g., a positive pressure that drives and/or urges the flow controller 440 toward the second contoured surface 426 such as during manufacturing, testing, and/or use).

The control device 400 is placed in its second state and/or configuration when the actuator 450 is in its first state and the flow controller 440 is in its second state. The transitioning of the flow controller 440 results in an increase in an inner volume of the portion of the sequestration chamber 430 defined between a surface of the flow controller 440 (e.g., a second surface opposite the first surface) and the second contoured surface 426. As described in detail above with reference to the device 200, the increase in the inner volume can, in turn, result in a negative pressure differential between the portion of the sequestration chamber 430 (defined at least in part by the flow controller 440) and, for example, the inlet 413 that is operable in drawing at least a portion of an initial flow, amount, or volume of bodily fluid from the inlet 413, through the fluid flow path 415 and the first port 417, and into the portion of the sequestration chamber 430. In some instances, the initial volume and/or flow of bodily fluid can be transferred into the sequestration chamber 430 until, for example, the flow controller 440 is fully expanded, flipped, and/or transitioned, until the negative pressure differential is reduced and/or equalized, and/or until a desired volume of bodily fluid is disposed within the portion of the sequestration chamber 430. Moreover, the restrictor 419 can be configured to restrict, limit, control, and/or modulate a magnitude of the negative pressure differential and/or suction force generated within the sequestration chamber 430 and/or on a surface of the flow controller 440, which in turn, can modulate a suction force within one or more flow paths and/or within the bodily fluid source (e.g., the vein of the patient), as described above with reference to the device 200. In other embodiments, the second port 418 and/or any suitable portion of the device 400 can be configured to modulate a suction force within one or more portions of the sequestration chamber 30 in any suitable manner such as, for example, those described above with reference to the device 200.

In some embodiments, the shape, size, and/or arrangement of the sequestration chamber 430 and/or the flow controller 440, the ventilation channels 431 and/or the ventilation ridges 424, the magnitude of the negative pressure differential or suction force, and/or the way in which the negative pressure differential or suction force is exerted can dictate and/or control a rate and/or manner in which the flow controller 440 is transitioned from the first state to the second state. In some instances, controlling the rate, order and/or manner in which the flow controller 440 is transitioned can result in one or more desired flow characteristics associated with a flow of air, gas, and/or bodily fluid into and/or through at least a portion of the sequestration chamber. For example, the arrangement included in this embodiment can be such that a transitioning and/or flipping of the third deformable portion 443 of the flow controller 440 is completed prior to completion of the transitioning and/or flipping of the first and second deformable portions 441 and 442. Moreover, the arrangement of the ventilation ridges 424 along the first contoured surface 421 can increase a likelihood and/or can ensure that the flow controller 440 transitions and/or flips in a desired manner or sequence by preventing potential flow restrictions and/or seals that may otherwise prevent the negative pressure differential or suction force from transitioning and/or flipping a portion of the flow controller 440 disposed on an opposite side of the restriction or seal.

This arrangement can be such that a portion of the sequestration chamber 430 collectively defined by the first deformable portion 441 and the first recess 427 of the second contoured surface 426 (e.g., a first volume of the sequestration chamber 430) receives at least a portion of a volume of air that was within the fluid flow path between the bodily fluid source and the sequestration chamber 430 prior to the fluid flow path receiving and/or being filled with bodily fluid. Similarly, a portion of the sequestration chamber 430 collectively defined by the second deformable portion 442 and the second recess 428 of the second contoured surface 426 (e.g., a second volume of the sequestration chamber 430) can receive at least a portion of the volume of air that was within the fluid flow path. Alternative arrangements of the sequestration chamber 430 and/or the flow controller 440 can be similar in form and function to those described above with reference to the sequestration chamber 230 and/or the flow controller 240, and thus they are not described in further detail herein.

Having transferred the initial volume of bodily fluid into the sequestration chamber 430, a force can be exerted on the end portion 451 of the actuator 450 to transition and/or place the actuator 450 in its second position, state, operating mode, and/or configuration, as described in above. In some instances, prior to exerting the force on the end portion 451 of the actuator 450, the actuator 450 may be transitioned from a locked configuration or state to an unlocked configuration or state. In the embodiment shown in FIGS. 22-27, the transition of the actuator 450 can be achieved by and/or can otherwise result from user interaction and/or manipulation of the actuator 450. In other embodiments, however, the transition of the actuator 450 can occur automatically in response to negative pressure and/or associated flow dynamics within the device 400, and/or enacted by or in response to an external energy source that generates one or more dynamics or states that result in the transitioning of the actuator 450.

As shown in FIGS. 26 and 27, the control device 400 is placed in its third state when each of the flow controller 440 and the actuator 450 is in its second state. When the actuator 450 is transitioned to its second state, position, and/or configuration, the inlet 413 and the outlet 414 are placed in fluid communication (e.g., via the fluid flow path 416 and/or the flow channel 452) while the fluid flow path 415 and/or the first port 417 is/are sequestered, isolated, and/or otherwise not in fluid communication with the inlet 413 and/or the outlet 414. As such, the initial volume of bodily fluid is sequestered in the portion of the sequestration chamber 430. Moreover, in some instances, contaminants such as, for example, dermally residing microbes and/or any other contaminants can be entrained and/or included in the initial volume of the bodily fluid and thus, are sequestered in the sequestration chamber 430 when the initial volume is sequestered therein. As such, the negative pressure otherwise exerted on or through the fluid flow path 416 and through the second port 418 is now exerted on or through the outlet 414 and the inlet 413 via, for example, at least a portion of the fluid flow paths 415 and 416 and/or the flow channel 452 of the actuator 450. In response, bodily fluid can flow from the inlet 413, through the actuator portion 412 of the housing 410, through the outlet 414, and into the fluid collection device coupled to the outlet 414. Accordingly, the device 400 can function in a manner substantially similar to that of the devices 100 and/or 200 described in detail above.

Figure 28:
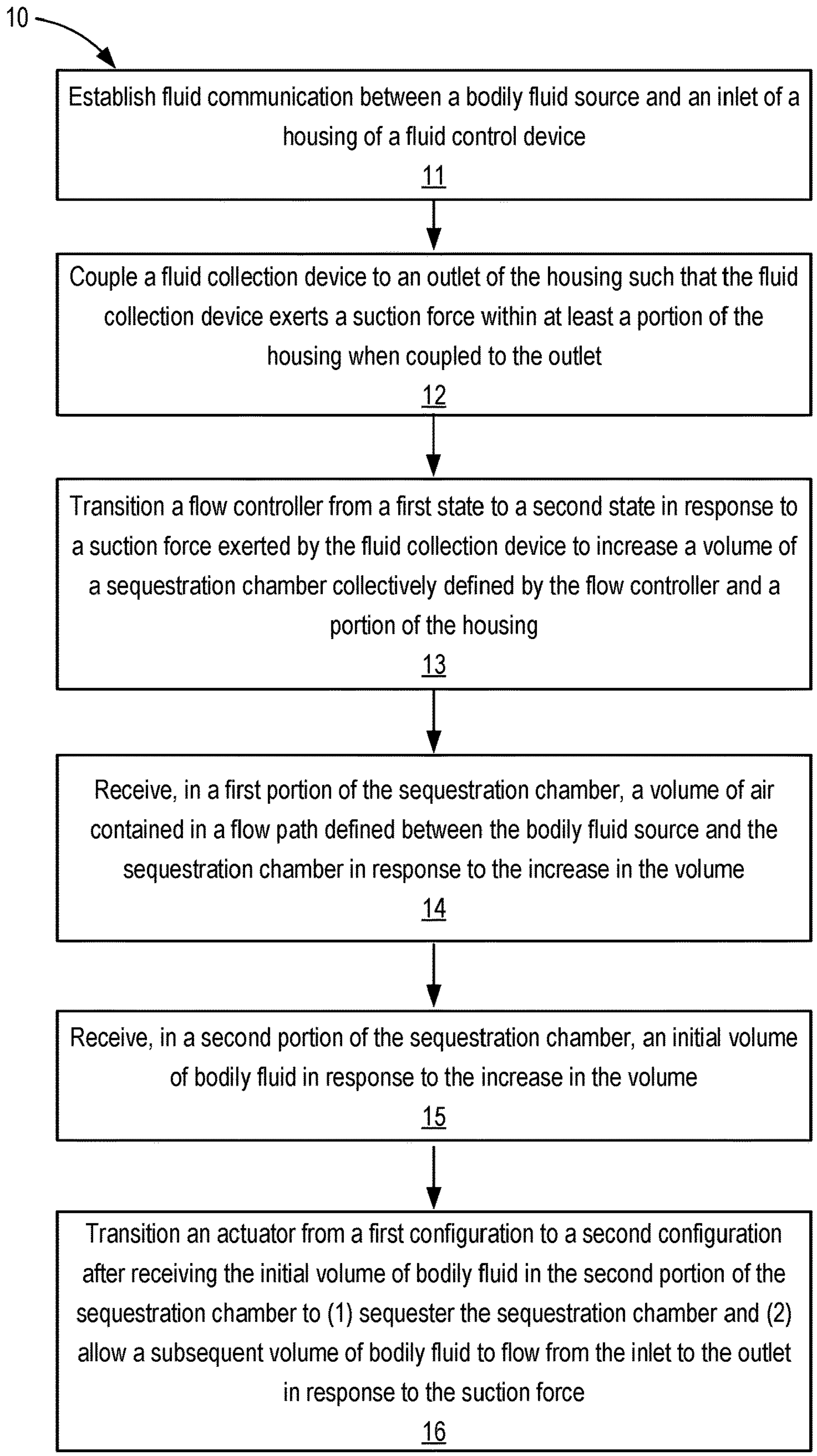
FIG. 28 is a flowchart illustrating a method of using a fluid control device according to an embodiment.

Referring now to FIG. 28, a flowchart is presented illustrating a method 10 of using a fluid control device to obtain a bodily fluid sample with reduced contamination according to an embodiment. The fluid control device can be similar to and/or substantially the same as any of the fluid control devices 100, 200, 300, and/or 400 described in detail above. Accordingly, the fluid control device (also referred to herein as "control device" or "device") can include a housing, a flow controller, and an actuator. The method 10 includes establishing fluid communication between a bodily fluid source and an inlet of the housing, at 11. For example, in some embodiments, a user can manipulate the fluid control device to physically and/or fluidically couple the inlet to a lumen-containing device (e.g., a needle, IV, PICC line, etc.), which in turn, is in fluid communication with a patient. In other embodiments, the bodily fluid source can be a source of bodily fluid other than a patient (e.g., a reservoir, container, etc.).

A fluid collection device is coupled to an outlet of the housing, at 12. The coupling of the fluid collection device to the outlet is configured to result in and/or otherwise generate a negative pressure differential within at least a portion of the fluid control device, as described in detail above with reference to the devices 100, 200, 300, and/or 400. In some embodiments, for example, the fluid collection device can be an evacuated container, a sample or culture bottle that defines a negative pressure, a syringe, and/or the like. The flow controller of the control device is transitioned from a first state to a second state in response to a suction force exerted by the fluid collection device to increase a volume of a sequestration chamber collectively defined by the flow controller and a portion of the housing, at 13. For example, in some embodiments, the flow controller can be a fluid impermeable bladder or the like—similar to the flow controllers 240, 340, and/or 440 described in detail above—that is disposed within the sequestration chamber.

The flow controller (e.g., bladder) can define any number of deformable portions configured to transition, deform, flip, and/or otherwise reconfigure in response to a suction force. In some embodiments, a first portion of the sequestration chamber can be associated with and/or at least partially defined by a first deformable portion of the flow controller and a second portion of the sequestration chamber can be associated with and/or at least partially defined by a second deformable portion of the flow controller. In some embodiments, the arrangement of the flow controller within the sequestration chamber can be such that the first portion and the second portion of the sequestration chamber are on a first side of the flow controller (e.g., fluid impermeable bladder) and a third portion of the sequestration chamber is on a second side of the flow controller opposite the first side. As described above with reference to at least the devices 200, 300, and/or 400, the arrangement of the housing, flow controller, and actuator can be such that when the actuator is in a first state and/or configuration, the inlet is in fluid communication with the first and/or second portions of the sequestration chamber (e.g., via a port similar to the first ports 217, 317, and/or 417 described above) and the outlet is in fluid communication with the third portion of the sequestration chamber (e.g., via a port similar to the second ports 217, 317, and/or 417 described above). As such, the third portion of the sequestration chamber can be exposed to at least a portion of the suction force generated by the fluid collection device, which in turn, is operable to transition the flow controller from its first state to its second state.

The first portion of the sequestration chamber receives a volume of air contained in a flow path defined between the bodily fluid source and the sequestration chamber in response to the increase in the volume of the sequestration chamber, at 14. For example, in some embodiments, the inlet of the housing can be fluidically coupled to a needle or lumen-containing device that is, in turn, inserted into a portion of the patient. As such, the flow path can be collectively defined by, for example, a lumen of the needle or lumen-containing device, a lumen of the inlet of the housing, and a lumen of one or more flow paths, channels, openings, ports, etc. of the defined by the housing. In other words, the control device can be configured to purge the flow path of air prior to transferring bodily fluid into the sequestration chamber.

In some embodiments, the first portion of the sequestration chamber can be, for example, a center or central portion of the sequestration chamber. In some embodiments, the first portion of the sequestration chamber can be collectively formed by any number of regions, volumes, and/or sections (e.g., similar to the sequestration chambers 230 and/or 430 described above). In other embodiments, the first portion of the sequestration chamber can be a single and/or continuous portion (e.g., similar to the sequestration chamber 330 described above). In still other embodiments, the first portion of the sequestration chamber and the second portion of the sequestration chamber can be "inline" such that the entire sequestration chamber or substantially the entire sequestration chamber is a single and/or continuous volume. For example, in some embodiments, the sequestration chamber can have a shape and/or arrangement similar to those described in detail in U.S. Patent Publication Serial No. 2019/0076074 entitled, "Fluid Control Devices and Methods of Using the Same," filed Sep. 12, 2018 (referred to herein as "the '074 Publication"), the disclosure of which is incorporated herein by reference in its entirety.

The second portion of the sequestration chamber receives an initial volume of bodily fluid in response to the increase in the volume of the sequestration chamber, at 15. More specifically, the second portion of the sequestration chamber can receive the initial volume of bodily fluid after the first portion of the sequestration chamber receives the volume of air. In some embodiments, the initial volume of bodily fluid can be a volume sufficient to substantially fill the second portion of the sequestration chamber. In other embodiments, the initial volume of bodily fluid can be a volume or amount of bodily fluid that flows into the second portion of the sequestration chamber while a negative pressure differential (e.g., resulting from the increase in volume) is below a threshold magnitude or amount. In other embodiments, bodily fluid can flow into the second portion of the sequestration chamber until pressures within the sequestration chamber and/or within the flow path between the bodily fluid source and the sequestration chamber are equalized. In still other embodiments, the initial volume can be any suitable amount or volume of bodily fluid such as any of the amounts or volumes described in detail herein. In some instances, the filling or substantial filling of the second portion of the sequestration chamber can be operable to sequester, retain, and/or fluidically lock the volume of air in the first portion of the sequestration chamber.

After receiving the initial volume of bodily fluid, the actuator of the device is transitioned from a first configuration to a second configuration to (1) sequester the sequestration chamber and (2) allow a subsequent volume of bodily fluid to flow from the inlet to the outlet in response to the suction force, at 16. In some embodiments, the actuator can transition from a first state to a second state to automatically sequester the initial volume of bodily fluid in the sequestration portion. In other embodiments, the actuator can transition from a first state to a second state in response to a force exerted by a user, as described above with reference to the actuators 250, 350, and/or 450. For example, in some embodiments, the actuator can be a rod or plunger that includes one or more seals or the like that can (1) fluidically isolate at least a portion of a flow path between the inlet and the sequestration chamber, (2) fluidically isolate at least a portion of a flow path between the outlet and the sequestration chamber, and (3) establish fluid communication between the inlet and the outlet to allow the subsequent volume of bodily fluid to flow therebetween.

With the fluid collection device fluidically coupled to the outlet of the housing, the subsequent volume of bodily fluid (e.g., one or more sample volumes) can be conveyed into the fluid collection device and used, for example, in any suitable testing such as those described herein. As described in detail above, in some instances, sequestering the initial volume of bodily fluid in the sequestration portion of the device can sequester any contaminants contained in the initial volume. Accordingly, contaminants in the subsequent volume of bodily fluid that may otherwise lead to false or inaccurate results in testing can be reduced or substantially eliminated.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features, concepts, and/or combinations of components, other embodiments are possible having any combination or sub-combination of any features, concepts, and/or components from any of the embodiments described herein.

In some embodiments, the specific configurations of the various components can also be varied. For example, the size and specific shape of the various components can be different from the embodiments shown, while still providing the functions as described herein. In some embodiments, varying the size and/or shape of such components may reduce an overall size of the device and/or may increase the ergonomics of the device without changing the function of the device. In some embodiments, the size and/or shape of the various components can be specifically selected for a desired or intended usage. For example, in some embodiments, a device such as those described herein can be configured for use with or on seemingly healthy adult patients. In such embodiments, the device can include a sequestration chamber that has a first volume (e.g., about 0.5 ml to about 5.0 ml). In other embodiments, a device such as those described herein can be configured for use with or on, for example, very sick patients and/or pediatric patients. In such embodiments, the device can include a sequestration chamber that has a second volume that is less than the first volume (e.g., less than about 0.5 ml). Thus, it should be understood that the size, shape, and/or arrangement of the embodiments and/or components thereof can be adapted for a given use unless the context explicitly states otherwise.

Any of the embodiments described herein can be used in conjunction with any suitable fluid transfer, fluid collection, and/or fluid storage device such as, for example, the fluid reservoirs described in the '420 patent. In some instances, any of the embodiments described herein can be used in conjunction with any suitable transfer adapter, fluid transfer device, fluid collection device, and/or fluid storage devices such as, for example, the devices described in the '783 Patent, the '510 Publication, the '074 Publication, and/or any of the devices described in U.S. Pat. No. 8,535,241 entitled, "Fluid Diversion Mechanism for Bodily-Fluid Sampling," filed Oct. 22, 2012; U.S. Pat. No. 9,060,724 entitled, "Fluid Diversion Mechanism for Bodily-Fluid Sampling," filed May 29, 2013; U.S. Pat. No. 9,155,495 entitled, "Syringe-Based Fluid Diversion Mechanism for Bodily-Fluid Sampling," filed Dec. 2, 2013; U.S. Patent Publication No. 2016/0361006 entitled, "Devices and Methods for Syringe Based Fluid Transfer for Bodily-Fluid Sampling," filed Jun. 23, 2016; U.S. Patent Publication No. 2018/0140240 entitled, "Systems and Methods for Sample Collection with Reduced Hemolysis," filed Nov. 20, 2017; and/or U.S. Pat. No. 9,950,084 entitled, "Apparatus and Methods for Maintaining Sterility of a Specimen Container," filed Sep. 6, 2016, the disclosures of which are incorporated herein by reference in their entireties.

While the control devices 100, 200, 300, and/or 400 are described as transferring a bodily fluid into the device as a result of a negative pressure within a fluid collection device, in other embodiments, the devices described herein can be used with any suitable device configured to establish a negative pressure differential, suction force, and/or the like such as, for example, a syringe or pump. In other embodiments, a control device can include a pre-charged sequestration chamber, a vented sequestration chamber, a manually activated device configured to produce a negative pressure, an energy source (e.g., a chemical energy source, a kinetic energy source, and/or the like), and/or any other suitable means of defining and/or forming a pressure differential within a portion of the control device. Moreover, a control device can be coupled to such a collection device by a user (e.g., doctor, nurse, technician, physician, etc.) or can be coupled or assembled during manufacturing. In some embodiments, pre-assembling a control device and a collection device (e.g., a sample container or syringe) can, for example, force compliance with a sample procurement protocol that calls for the sequestration of an initial amount of bodily fluid prior to collecting a sample volume of bodily fluid.

While some of the embodiments described above include a flow controller and/or an actuator having a particular configuration and/or arrangement, in other embodiments, a fluid control device can include any suitable flow controller and/or actuator configured to selectively control a flow of bodily fluid through one or more portions of the fluid control device. For example, while some embodiments include an actuator having one or more seals arranged as an o-ring or an elastomeric over-mold, which is/are moved with the actuator and relative to a portion of the device (e.g., an inner surface of a housing or the like), in other embodiments, a fluid control device can include one or more seals having any suitable configuration. For example, in some embodiments, a fluid control device can include one or more seals arranged as an elastomeric sheet or the like that is/are fixedly coupled to a portion of the control device. In such embodiments, a portion of an actuator such as a pin or rod can extend through an opening defined in the one or more elastomeric sheets, which in turn, form a substantially fluid tight seal with an outer surface of the pin or rod. As such, at least a portion of the actuator can move relative to the one or more elastomeric sheets, which in turn, remain in a substantially fixed position relative to the portion of the control device. In some embodiments, removal of the portion of the actuator from the opening defined by the one or more elastomeric sheets can allow a flow of fluid through the opening that was otherwise occluded by the portion of the actuator. Accordingly, the one or more elastomeric sheets can function in a similar manner as any of the seals described herein. Moreover, in some embodiments, such an arrangement may, for example, reduce an amount of friction associated with forming the desired fluid tight seals, which in turn, may obviate the use of a lubricant otherwise used to facilitate the movement of the seals within the control device.

In some embodiments, a device and/or a flow controller can include one or more vents, membranes, members, semi-permeable barriers, and/or the like configured to at least partially control a flow of fluid through the device, flow controller, and/or actuator. For example, while portions of the sequestration chamber 230 are described above as receiving and retaining a volume of air evacuated, vented, and/or purged from the fluid flow path between the bodily fluid source and the sequestration chamber 230, in other embodiments, a sequestration chamber 230 can include a vent or selectively permeable member configured to allow the air to exit the sequestration chamber 230. For example, in some embodiments, a bladder or diaphragm (or portion thereof) can be formed of or from a semi-permeable material that can allow air but not bodily fluid to flow therethrough. In other embodiments, a semi-permeable material can be disposed in or along a fluid flow path between the sequestration chamber and at least one of an outlet or an inlet to selectively allow air and/or bodily fluid to flow therebetween. In some embodiments, a fluid control device can include a semi-permeable member and/or membrane that can be similar in form and/or function to the semi-permeable members and/or membranes (e.g., flow controllers) described in the '074 Publication incorporated by reference hereinabove.

While the flow controller 240, 340, and 440 are described above as being bladders configured to transition, move, flip, and/or otherwise reconfigure in response to an amount of negative pressure exerted on a surface of the bladder exceeding a threshold amount of negative pressure, in other embodiments, a fluid control device can include any suitable flow controller, actuator, semi-permeable member (e.g., air permeable and liquid impermeable), and/or the like configured to transition, move, flip, and/or otherwise reconfigure in any suitable manner in response to being exposed to a desired and/or predetermined amount of negative pressure. In other embodiments, a control device can include a bladder (or flow controller) that is configured to "flip" (e.g., relatively quickly and/or substantially uniformly transition) or configured to gradually transition (e.g., unroll, unfold, unfurl, and/or otherwise reconfigure) from the first state to the second state in response to being exposed to a negative pressure differential. In some instances, controlling a rate at which a bladder (or flow controller) is transitioned may allow for a modulation and/or control of a negative pressure differential produced within the sequestration chamber, and in turn, a magnitude of a suction force exerted within a patient's vein and/or other suitable bodily fluid source.

While some of the embodiments described above include a flow controller and/or actuator that physically and/or mechanically sequesters one or more portions of a fluid control device, in other embodiments, a fluid control device need not physically and/or mechanically sequester one or more portions of the fluid control device. For example, in some embodiments, an actuator such as the actuator 250 can be transitioned from a first state in which an initial volume of bodily fluid can flow from an inlet to a sequestration chamber or portion, to a second state in which (1) the sequestration chamber or portion is physically and/or mechanically sequestered and (2) the inlet is in fluid communication with an outlet of the fluid control device. In other embodiments, however, an actuator and/or any other suitable portion of a fluid control device can transition from a first state in which an initial volume of bodily fluid can flow from an inlet to a sequestration chamber or portion, to a second state in which the inlet is placed in fluid communication with the outlet without physically and/or mechanically sequestering (or isolating) the sequestration chamber or portion. When such a control device is in the second state, one or more features and/or geometries of the control device can result in a preferential flow of bodily fluid from the inlet to the outlet and the initial volume of bodily fluid can be retained in the sequestration chamber or portion without physically and/or mechanically being sequestered or isolated.

While the restrictor 219 is described above as modulating and/or controlling a magnitude of negative pressure applied on or through at least a portion of the device 200 (e.g., within the sequestration chamber 230 and/or otherwise on the flow controller 240), in other embodiments, a control device can include any suitable feature, mechanism, and/or device configured to modulate, create, and/or otherwise control one or more pressure differentials through at least a portion of the control device. For example, in some embodiments, a user can transition and/or move an actuator to change (e.g., reduce or increase) the size of one or more portions of a fluid flow path or fluid flow interface within a portion of the control device to manually modulate and/or otherwise control an amount or magnitude of negative pressure within one or more portions of a control device.

Although not shown, any of the devices described herein can include an opening, port, coupler, septum, Luer-Lok, gasket, valve, threaded connecter, standard fluidic interface, etc. (referred to for simplicity as a "port") in fluid communication with the sequestration chamber. In some such embodiments, the port can be configured to couple to any suitable device, reservoir, pressure source, etc. For example, in some embodiments, the port can be configured to couple to a reservoir, which in turn, can allow a greater volume of bodily fluid to be diverted and/or transferred into the sequestration chamber. In other embodiments, the port can be coupled to a negative pressure source such as an evacuated container, a pump, a syringe, and/or the like to collect a portion or the full volume of the bodily fluid in the sequestration chamber, channel, reservoir, etc. and can use that volume of bodily fluid (e.g., the pre-sample volume) for additional clinical and/or in vitro diagnostic testing purposes. In other embodiments, the port can be configured to receive a probe, sampling tool, testing device, and/or the like that can be used to perform one or more tests (e.g., tests not sensitive to potential contamination) on the initial volume while the initial volume is disposed or sequestered in the sequestration chamber. In still other embodiments, the port can be coupled to any suitable pressure source or infusion device configured to infuse the initial volume of bodily fluid sequestered in the sequestration chamber back into the patient and/or bodily fluid source (e.g., in the case of pediatric patients, very sick patients, patients having a low blood volume, and/or the like). In other embodiments, the sequestration channel, chamber, and/or reservoir can be configured with the addition of other diagnostic testing components integrated into the chamber (e.g., a paper test) such that the initial bodily fluid is used for that test.

In still other embodiments, the sequestration chamber, channel, and/or reservoir can be designed, sized, and configured to be removable and compatible with testing equipment and/or specifically accessible for other types of bodily fluid tests commonly performed on patients with suspected conditions. By way of example, a patient with suspected sepsis commonly has blood samples collected for lactate testing, procalcitonin testing, and blood culture testing. All of the fluid control devices described herein can be configured such that the sequestration chamber, channel, reservoir, etc. can be removed (e.g., after receiving the initial volume of bodily fluid) and the bodily fluid contained therein can be used for these additional testing purposes before or after the subsequent sample is collected for microbial testing.

Although not shown, in some embodiments, a fluid control device can include one or more lumen, channels, flow paths, etc. configured to selectively allow for a "bypass" flow of bodily fluid, where an initial amount or volume of bodily fluid can flow from the inlet, through the lumen, cannel, flow path, etc. to bypass the sequestration chamber, and into the collection device. In some embodiments, the fluid control device can include an actuator having, for example, at least three states—a first in which bodily fluid can flow from the inlet to the sequestration chamber, a second in which bodily fluid can flow from the inlet to the outlet after the initial volume is sequestered in the sequestration chamber, and a third in which bodily fluid can flow from the inlet, through the bypass flow path, and to the outlet. In other embodiments, the control device can include a first actuator configured to transition the device between a first and second state, as described in detail above with reference to specific embodiments, and can include a second actuator configured to transition the device to a bypass configuration or the like. In still other embodiments, the control device can include any suitable device, feature, component, mechanism, actuator, controller, etc. configured to selectively place the fluid control device in a bypass configuration or state.

In some embodiments, a method of using a fluid control device such as those described herein can include the ordered steps of establishing fluid communication between a bodily fluid source (e.g., a vein of a patient or the like) and an inlet of a fluid control device. An outlet of the fluid control device is then placed in fluid communication with and/or otherwise engages a negative pressure source. Such a negative pressure source can be a sample reservoir, a syringe, an evacuated container, an intermediate transfer device, and/or the like. The fluid control device can be in a first state or operating mode when the outlet is coupled to the negative pressure source and, as such, a negative pressure differential is applied through the fluid control device that draws an initial volume of bodily fluid into a sequestration chamber of the fluid control device. For example, a negative pressure within a sample reservoir can be operable in drawing an initial volume of bodily fluid from a patient and into the sequestration chamber. Once the initial volume of bodily fluid is disposed in the sequestration chamber, the fluid control device is transitioned, either automatically or via user intervention, from the first state or operating mode to a second state or operating mode such that (1) the initial volume is sequestered in the sequestration chamber and (2) fluid communication is established between the inlet and the outlet. The sequestration of the initial volume can be such that contaminants entrained in the flow of the initial volume are likewise sequestered within the sequestration chamber. With the initial volume of bodily fluid sequestered in the sequestration chamber and with fluid communication established between the inlet and the outlet, subsequent volumes of bodily fluid that are substantially free of contamination can be collected in one or more sample reservoirs.

While the method of using the fluid control device is explicitly described as including the recited ordered steps, in other embodiments, the ordering of certain events and/or procedures in any of the methods or processes described herein may be modified and such modifications are in accordance with the variations of the invention. Additionally, certain events and/or procedures may be performed concurrently in a parallel process when possible, as well as performed sequentially as described above. Certain steps may be partially completed or may be omitted before proceeding to subsequent steps. For example, while the devices are described herein as transitioning from a first state to a second state in a discrete operation or the like, it should be understood that the devices described herein can be configured to automatically and/or passively transition from the first state to the second state and that such a transitioning may occur over a period of time. In other words, the transitioning from the first state to the second state may, in some instances, be relatively gradual such that as a last portion of the initial volume of bodily fluid is being transferred into the sequestration chamber, the housing begins to transition from the first state to the second state. In some instances, the rate of change when transitioning from the first state to the second state can be selectively controlled to achieve one or more desired characteristics associated with the transition. Moreover, in some such instances, the inflow of the last portion of the initial volume can limit and/or substantially prevent bodily fluid already disposed in the sequestration chamber from escaping therefrom. Accordingly, while the transitioning from the first state to the second state may occur over a given amount of time, the sequestration chamber can nonetheless sequester the volume of bodily fluid disposed therein.

What is claimed:

1. An apparatus for procuring bodily fluid samples with reduced contamination, the apparatus comprising:

a housing having a first portion and a second portion separate from the first portion, the first portion forming a sequestration chamber, the housing having an inlet configured to be fluidically coupled to a bodily fluid source and an outlet configured to be fluidically coupled to a fluid collection device;

a flow controller disposed in the sequestration chamber; and an actuator at least partially disposed in the second portion of the housing, the actuator having a first configuration in which the inlet is in fluid communication with a portion of the sequestration chamber and a second configuration in which the inlet is in fluid communication with the outlet, the actuator in the first configuration at least partially defining a a first fluid flow path between the inlet and a first side of the flow controller and at least partially defining a second fluid flow path between the outlet and a second side of the flow controller, the flow controller configured to transition from a first state to a second state in response to a suction force being exerted at the outlet and to produce a negative pressure differential between the portion of the sequestration chamber and the inlet operable to draw an initial volume of bodily fluid into the portion of the sequestration chamber, the actuator configured to be transitioned to the second configuration after the initial volume of bodily fluid is drawn into the portion of the sequestration chamber to fluidically couple a portion of the first fluid flow path to a portion of the second fluid flow path and allow a subsequent volume of bodily fluid to flow from the inlet to the outlet in response to the suction force.

2. The apparatus of claim 1, wherein the first side of the flow controller partially defines the portion of the sequestration chamber.

3. The apparatus of claim 2, wherein the flow controller is a diaphragm configured to deform in response to the suction force to transition from the first state to the second state.

4. The apparatus of claim 1, wherein the actuator includes at least one seal configured to form a substantially fluid tight seal with an inner surface of the housing to prevent bodily fluid from flowing past the at least one seal.

5. The apparatus of claim 4, wherein the actuator in the first configuration is such that the at least one seal is between the inlet and the outlet to prevent bodily fluid from flowing therebetween.

6. The apparatus of claim 1, wherein transitioning the actuator from the first configuration to the second configuration includes moving the actuator from a first position relative to the housing to a second position relative to the housing to fluidically couple the portion of the first fluid flow path to the portion of the second fluid flow path.

7. The apparatus of claim 1, wherein the actuator is configured to automatically transition between the first configuration and the second configuration.

8. The apparatus of claim 1, wherein a rate at which the flow controller transitions from the first state to the second state at least partially controls the negative pressure differential between the portion of the sequestration chamber and the inlet.

9. The apparatus of claim 1, wherein the portion of the sequestration chamber is a first portion of the sequestration chamber, the flow controller separating the first portion of the sequestration chamber on the first side of the flow controller from a second portion of the sequestration chamber on the second side of the flow controller.

10. The apparatus of claim 9, wherein the housing includes a first port and a second port, and the actuator in the first configuration being such that the first port places the inlet in fluid communication with the first portion of the sequestration chamber and the second port places the outlet in fluid communication with the second portion of the sequestration chamber.

11. The apparatus of claim 9, wherein the first portion of the sequestration chamber has a first volume when the flow controller is in the first state and a second volume when the flow controller is in the second state, the second volume being greater than the first volume.

12. The apparatus of claim 1, wherein fluidically coupling the fluid collection device is operable to generate the suction force at the outlet.

13. An apparatus for procuring bodily fluid samples with reduced contamination, the apparatus comprising:

a housing having a first portion and a second portion separate from the first portion, the first portion forming a sequestration chamber, the housing having an inlet configured to be fluidically coupled to a bodily fluid source and an outlet configured to be fluidically coupled to a fluid collection device;

an actuator at least partially disposed in the second portion of the housing, the actuator in a first configuration allowing fluid communication between the inlet and a first portion of the sequestration chamber via a first fluid flow path and allowing fluid communication between the outlet and a second portion of the sequestration chamber via a second fluid flow path, the actuator in a second configuration fluidically coupling a portion of the first fluid flow path and a portion of the second fluid flow path to place the inlet in fluid communication with the outlet; and a flow controller disposed in the sequestration chamber, the flow controller configured to transition from a first state to a second state in response to a suction force being exerted through the second fluid flow path and the second portion of the sequestration chamber when the outlet is fluidically coupled to the fluid collection device and to produce a negative pressure differential between the first portion of the sequestration chamber and the inlet operable to draw an initial volume of bodily fluid into the first portion of the sequestration chamber via the first fluid flow path, the actuator configured to transition from the first configuration to the second configuration after the initial volume of bodily fluid is in the first portion of the sequestration chamber to allow a subsequent volume of bodily fluid to flow from the inlet to the outlet in response to the suction force.

14. The apparatus of claim 13, wherein the housing includes a first port and a second port, and the actuator in the first configuration being such that the first port places the inlet in fluid communication with the first portion of the sequestration chamber and the second port places the outlet in fluid communication with the second portion of the sequestration chamber.

15. The apparatus of claim 14, wherein the actuator in the second configuration is such that the first port is sequestered from the inlet and the second port is sequestered from the outlet.

16. The apparatus of claim 13, wherein the flow controller is a diaphragm configured to deform in response to the suction force to transition from the first state to the second state.

17. The apparatus of claim 13, wherein a first side of the flow controller partially defines the first portion of the sequestration chamber and a second side of the flow controller partially defines the second portion of the sequestration chamber.

18. The apparatus of claim 17, wherein a volume of the first portion of the sequestration chamber is configured to increase as a result of the flow controller transitioning from the first state to the second state.

19. The apparatus of claim 18, wherein a volume of the second portion of the sequestration chamber is configured to decrease as a result of the flow controller transitioning from the first state to the second state.

20. The apparatus of claim 17, wherein the flow controller in the first state is such that the first portion of the sequestration chamber has a first volume and the second portion of the sequestration chamber has a second volume greater than the first volume, and the flow controller in the second state is such that the first portion of the sequestration chamber has a third volume and the second portion of the sequestration chamber has a fourth volume less than the third volume.

21. A system for procuring bodily fluid samples with reduced contamination, the system comprising:

a fluid control device, including:

a housing having a first portion and a second portion separate from the first portion, the first portion forming a sequestration chamber, the housing having an inlet configured to be fluidically coupled to a bodily fluid source and an outlet;

a flow controller disposed in the sequestration chamber; and an actuator at least partially disposed in the second portion of the housing, the actuator having a first configuration in which the inlet is in fluid communication with a portion of the sequestration chamber, and a second configuration in which the inlet is in fluid communication with the outlet, the actuator in the first configuration at least partially defining a first fluid flow path between the inlet and a first side of the flow controller and at least partially defining a second fluid flow path between the outlet and a second side of the flow controller; and a fluid collection device fluidically coupleable to the outlet of the fluid control device, the fluid collection device configured to exert a suction force through the second fluid flow path when fluidically coupled to the outlet, the flow controller configured to transition from a first state to a second state in response to the suction force being exerted through the second fluid flow path and to produce a negative pressure differential between the portion of the sequestration chamber and the inlet operable to draw an initial volume of bodily fluid into the portion of the sequestration chamber, the actuator configured to be transitioned to the second configuration after the initial volume of bodily fluid is drawn into the portion of the sequestration chamber to fluidically couple a portion of the first fluid flow path to a portion of the second fluid flow path and allow a subsequent volume of bodily fluid to flow from the inlet to the outlet in response to the suction force.

22. The system of claim 21, wherein the first side of the flow controller partially defines the portion of the sequestration chamber.

23. The system of claim 21, wherein the flow controller is a diaphragm configured to deform in response to the suction force to transition from the first state to the second state.

24. The system of claim 21, wherein the actuator includes at least one seal configured to form a substantially fluid tight seal with an inner surface of the housing, the actuator in the first configuration is such that the at least one seal separates the first fluid flow path from the second fluid flow path to prevent bodily fluid from flowing from the inlet to the outlet.

25. The system of claim 24, wherein the actuator in the second configuration is such that the at least one seal allows fluid communication between the portion of the first fluid flow path and the portion of the second fluid flow path.

26. The system of claim 21, wherein the actuator is configured to automatically transition between the first configuration and the second configuration.

27. The system of claim 21, wherein a rate at which the flow controller transitions from the first state to the second state at least partially controls the negative pressure differential between the portion of the sequestration chamber and the inlet.

28. The system of claim 21, wherein the portion of the sequestration chamber is a first portion of the sequestration chamber, the flow controller separates the first portion of the sequestration chamber on the first side of the flow controller from a second portion of the sequestration chamber on the second side of the flow controller.

29. The system of claim 28, wherein the first portion of the sequestration chamber has a first volume when the flow controller is in the first state and a second volume greater than the first volume when the flow controller is in the second state.

30. The system of claim 29, wherein the housing includes a first port and a second port, and the actuator in the first configuration being such that the first port places the inlet in fluid communication with the first portion of the sequestration chamber and the second port places the outlet in fluid communication with the second portion of the sequestration chamber.

* * * * *